(12) United States Patent
Andrews et al.

(10) Patent No.: US 7,795,416 B2
(45) Date of Patent: *Sep. 14, 2010

(54) TELOMERASE EXPRESSION REPRESSOR PROTEINS AND METHODS OF USING THE SAME

(75) Inventors: William H. Andrews, Reno, NV (US); Christopher A. Foster, Carmichael, CA (US); Stephanie Fraser, Sparks, NV (US); Hamid Mohammadpour, Reno, NV (US); Laura Briggs, Reno, NV (US)

(73) Assignee: Sierra Sciences Inc., Reno, NV (US)

( * ) Notice: Subject to any disclaimer, the term of this patent is extended or adjusted under 35 U.S.C. 154(b) by 583 days.

This patent is subject to a terminal disclaimer.

(21) Appl. No.: 11/726,388

(22) Filed: Mar. 20, 2007

(65) Prior Publication Data

US 2007/0238639 A1 Oct. 11, 2007

Related U.S. Application Data

(63) Continuation of application No. 10/177,744, filed on Jun. 21, 2002, now Pat. No. 7,211,435.

(60) Provisional application No. 60/300,115, filed on Jun. 21, 2001, provisional application No. 60/366,069, filed on Mar. 19, 2002.

(51) Int. Cl.
*C07H 21/04* (2006.01)
*C12N 15/85* (2006.01)

(52) U.S. Cl. .................. 536/24.1; 435/455

(58) Field of Classification Search ............ None
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 5,464,764 A | 11/1995 | Capecchi et al. | |
| 5,583,016 A | 12/1996 | Villeponteau et al. | |
| 5,627,052 A | 5/1997 | Schrader | |
| 5,658,570 A | 8/1997 | Newman et al. | |
| 5,681,722 A | 10/1997 | Newman et al. | |
| 5,693,780 A | 12/1997 | Newman et al. | |
| 5,750,105 A | 5/1998 | Newman et al. | |
| 5,756,096 A | 5/1998 | Newman et al. | |
| 5,837,857 A | 11/1998 | Villeponteau et al. | |
| 5,858,777 A | 1/1999 | Villeponteau et al. | |
| 5,876,979 A | 3/1999 | Andrews et al. | |
| 5,958,680 A | 9/1999 | Villeponteau et al. | |
| 6,007,989 A | 12/1999 | West et al. | |
| 6,013,468 A | 1/2000 | Andrews et al. | |
| 6,054,575 A | 4/2000 | Villeponteau et al. | |
| 6,093,809 A | 7/2000 | Cech et al. | |
| 6,686,159 B2 | 2/2004 | Andrews et al. | |

FOREIGN PATENT DOCUMENTS

| | | |
|---|---|---|
| WO | WO99/33998 A1 | 7/1999 |
| WO | WO99/35243 A2 | 7/1999 |
| WO | WO99/50279 A2 | 10/1999 |
| WO | WO00/46355 A2 | 8/2000 |

OTHER PUBLICATIONS

Jenks, Trends in Comparative Endocrinology and Neurobiology, 2009. Ann. N.Y. Acad. Sci. vol. 1163, pp. 17-30.*
Dickmeis, Briefings in Functional Genomics and Proteomics, 2005. vol. 3, No. 4, pp. 332-350).*
Wang et al. (Nucleic Acids Research, 2009. vol. 37, No. 8, pp. 2618-2629).*
Poole et al. (Gene, 2001. vol. 269, pp. 1-12).*
Masahiro Takakura et al. "Cloning of Human Telomerase Catalytic Subunit (hTERT) Gene Promoter and Identification of Proximal Core Promoter Sequences Essential for Transcriptional Activation in Immortalized and Cancer Cells" Cancer Research, vol. 59:551-557, Feb. 1, 1999.
Wick, M. et al. "Genomic organization and promoter characterization of the gene encoding the human telomerase reverse transcriptase (hTERT)" GENBANK accession No. AF128893.
Wu et al., "Direct activation of TERT transcription by c-MYC" Nature Genetics, 1999, pp. 220-224, vol. 21.
Wu et al., "Direct activation of TERT transcription by c-MYC" GENBANK accession No. AF114847.
Yu-Shen Cong et al. "The human telomerase catalytic subunit hTERT: organization of the gene and characterization of the promoter" Human Molecular Genetics, 1999, pp. 137-142, vol. 8, No. 1.

* cited by examiner

*Primary Examiner*—Celine X Qian
(74) *Attorney, Agent, or Firm*—Bret E. Field; Bozicevic, Field & Francis LLP

(57) ABSTRACT

Telomerase repressor proteins and nucleic acid compositions encoding the same are provided. The subject repressor proteins bind to a repressor site in the TERT minimal promoter, e.g., a Site C site, and thereby inhibit TERT expression. Also provided are methods of modulating, e.g., inhibiting or enhancing, TERT expression. The subject invention finds use in a variety of different applications, including therapeutic and therapeutic agent screening applications.

10 Claims, 22 Drawing Sheets

FIGURE 2 - Sheet 1

```
RESTRICTION SITES and REGIONS Map of DNA P87P2cDNA052601 (length
= 5724)
Restriction enzymes file: sites
Regions files: tempregcod
Ambiguous bases ARE NOT recognized.
Sequence is CIRCULAR.
Uncharacterized regions ARE identified.

********************************************
   1 CTACGATCCAGGCTGGAGTTGCGCTCGGCCGGTCTGAGCGCTGGCGCTGCCCGGACGCCG
     GATGCTAGGTCCGACCTCAACGCGAGCCGGCCAGACTCGCGACCGCGACGGGCCTGCGGC exo
     ************************************************************
  61 CGGGGTCCCCGCCAGCCCAGGGCACTCGGCGCGGGGATCTGCGCGCCTCGCTCTCCCTTC
     GCCCCAGGGGCGGTCGGGTCCCGTGAGCCGCGCCCCTAGACGCGCGGAGCGAGAGGGAAG n1
     ************************************************************
 121 CCGATGCCGCCGCCCGGCTGCTGATCGCCGCACCACCTTCCCTCATCGGCTTGGGTCCGT
     GGCTACGGCGGCGGGCCGACGACTAGCGGCGTGGTGGAAGGGAGTAGCCGAACCCAGGCA

+++++++++++++++++
                                             =================

*********************************************>
                                                    MetGluValAsnCysLe
 181 GGAGGTCCCTGCAGAGGCAGGAAGCCTCCTTAGGAAAGCAGGGATGGAGGTAAATTGTTT
     CCTCCAGGGACGTCTCCGTCCTTCGGAGGAATCCTTTCGTCCCTACCTCCATTTAACAAA

+++++++++++++++++++++++++++++++++++++++++++++++++++++++++++
                                exon2
     =========================================================== uThrLeuLysAspLeuIleSerProArgGlnProArgLeuAspPheAlaValGluAspGl
 241 AACACTAAAAGACCTGATCAGCCCCAGGCAGCCCAGACTAGATTTTGCAGTTGAAGATGG
     TTGTGATTTTCTGGACTAGTCGGGGTCCGTCGGGTCTGATCTAAAACGTCAACTTCTACC

+++++++++++++++++++++++++++++++++++++++++++++++++++++++++++
     ================>

********************************************
                       yGluAsnAlaGlnLysGluAsnIlePheValAspArgSerArgMetAlaProLysThrPr
 301 GGAAAATGCACAAAAGGAAAATATATTTGTTGATCGATCAAGGATGGCCCCGAAGACTCC
     CCTTTTACGTGTTTTCCTTTTATATAAACAACTAGCTAGTTCCTACCGGGGCTTCTGAGG

+++++++++++++++++++++++++++++++++++++++++++++++++++++++++++

************************************************************
     oIleLysAsnGluProIleAspLeuSerLysGlnLysLysPheThrProGluArgAsnPr
 361 AATAAAAAATGAACCAATTGATTTATCGAAGCAAAAAAAATTTACTCCAGAAAGAAATCC
     TTATTTTTTACTTGGTTAACTAAATAGCTTCGTTTTTTTTAAATGAGGTCTTTCTTTAGG

+++++++++++++++++++++++++++++++++++++++++++++++++++++++++++ exon3
     ************************************************************
     oIleThrProValLysLeuValAspArgGlnGlnAlaGluProTrpThrProThrAlaAs
```

FIGURE 2 - Sheet 2

```
421 CATTACTCCAGTTAAGCTTGTTGACAGACAGCAAGCGGAACCATGGACACCCACAGCTAA
    GTAATGAGGTCAATTCGAACAACTGTCTGTCGTTCGCCTTGGTACCTGTGGGTGTCGATT

++++++++++++++++++++++++++++++++++++++++++++++++++++++++++++

************************************************************
                          nLeuLysMetLeuIleSerAlaAlaSerProAspIleArgAspArgGluLysLysLysGl
481 CCTGAAGATGCTCATTAGTGCTGCCAGCCCAGATATAAGGGACCGGGAGAAGAAAAAGGG
    GGACTTCTACGAGTAATCACGACGGTCGGGTCTATATTCCCTGGCCCTCTTCTTTTTCCC

++++++++++++++++++++++++++++++++++++++++++++++++++++++++++++
                                                       ========

***********************************************************>
    yLeuPheArgProIleGluAsnLysAspAspAlaPheThrAspSerLeuGlnLeuAspVa
541 ACTATTCCGACCCATTGAAAACAAGGACGATGCATTTACAGATTCTCTACAGCTTGATGT
    TGATAAGGCTGGGTAACTTTTGTTCCTGCTACGTAAATGTCTAAGAGATGTCGAACTACA

++++++++++++++++++++++++++++++++++++++++++++++++++++++++++++
    ============================================================ lValGlyAspSerAlaValAspGluPheGluLysGlnArgProSerArgLysGlnLysSe
601 TGTTGGGGACAGTGCTGTGGACGAATTTGAAAAGCAAAGGCCAAGCAGAAAACAGAAAAG
    ACAACCCCTGTCACGACACCTGCTTAAACTTTTCGTTTCCGGTTCGTCTTTTGTCTTTTC

++++++++++++++++++++++++++++++++++++++++++++++++++++++++++++
            exon4
    ============================================================ rLeuGlyLeuLeuCysGlnLysPheLeuAlaArgTyrProSerTyrProLeuSerThrGl
661 TTTAGGACTCCTGTGCCAGAAGTTTCTAGCTCGCTATCCAAGTTATCCCTTGTCAACTGA
    AAATCCTGAGGACACGGTCTTCAAAGATCGAGCGATAGGTTCAATAGGGAACAGTTGACT

++++++++++++++++++++++++++++++++++++++++++++++++++++++++++++
    =================================>  ================
                                        ******************
    uLysThrThrIleSerLeuAspGluValAlaValSerLeuGlyValGluArgArgArgIl
721 GAAAACTACCATCTCCCTAGATGAAGTTGCTGTCAGTCTTGGTGTGGAAAGGAGACGCAT
    CTTTTGATGGTAGAGGGATCTACTTCAACGACAGTCAGAACCACACCTTTCCTCTGCGTA

++++++++++++++++++++++++++++++++++++++++++++++++++++++++++++
        E2FA
    ====================>

************************************************************
    eTyrAspIleValAsnValLeuGluSerLeuHisLeuValSerArgValAlaLysAsnGl
781 CTATGACATTGTAAATGTGCTGGAGTCGCTGCATCTGGTCAGCCGGGTGGCTAAGAATCA
    GATACTGTAACATTTACACGACCTCAGCGACGTAGACCAGTCGGCCCACCGATTCTTAGT

++++++++++++++++++++++++++++++++++++++++++++++++++++++++++++

************************************************************
    nTyrGlyTrpHisGlyArgHisSerLeuProLysThrLeuArgAsnLeuGlnArgLeuGl
841 GTATGGCTGGCATGGACGGCACAGCCTGCCAAAAACCCTGAGGAACCTCCAGAGACTAGG
    CATACCGACCGTACCTGCCGTGTCGGACGGTTTTTGGGACTCCTTGGAGGTCTCTGATCC
```

FIGURE 2 - Sheet 3

```
     ++++++++++++++++++++++++++++++++++++++++++++++++++++++++++++ exon5
         ***********************************************************
         yGluGluGlnLysTyrGluGluGlnMetAlaTyrLeuGlnGlnLysGluLeuAspLeuIl
 901     AGAGGAGCAGAAATATGAAGAGCAAATGGCCTACCTCCAACAGAAAGAGCTGGACCTGAT
         TCTCCTCGTCTTTATACTTCTCGTTTACCGGATGGAGGTTGTCTTTCTCGACCTGGACTA

++++++++++++++++++++++++++++++++++++++++++++++++++++++++++++

***********************************************************
         eAspTyrLysPheGlyGluArgLysLysAspGlyAspProAspSerGlnGluGlnGlnLe
 961     AGATTATAAATTTGGAGAACGTAAAAAAGATGGTGATCCAGATTCCCAGGAACAACAGTT
         TCTAATATTTAAACCTCTTGCATTTTTTCTACCACTAGGTCTAAGGGTCCTTGTTGTCAA

++++++++++++++++++++++++++++++++++++++++++++++++++++++++++++

================================

*****************************>
         uLeuAspPheSerGluProAspCysProSerSerSerAlaAsnSerArgLysAspLysSe
 1021    ACTGGATTTCTCTGAACCCGACTGTCCCTCTTCATCTGCAAACAGTAGAAAAGACAAGTC
         TGACCTAAAGAGACTTGGGCTGACAGGGAGAAGTAGACGTTTGTCATCTTTTCTGTTCAG

++++++++++++++++++++++++++++++++++++++++++++++++++++++++++++
                                                        exon6
         ============================================================= rLeuArgIleMetSerGlnLysPheValMetLeuPheLeuValSerLysThrLysIleVa
 1081    TCTGAGAATTATGAGCCAGAAGTTTGTCATGCTGTTCCTCGTCTCCAAAACCAAGATTGT
         AGACTCTTAATACTCGGTCTTCAAACAGTACGACAAGGAGCAGAGGTTTTGGTTCTAACA

++++++++++++++++++++++++++++++++++++++++++++++++++++++++++++

============================================================= lThrLeuAspValAlaAlaLysIleLeuIleGluGluSerGlnAspAlaProAspHisSe
 1141    CACTCTGGATGTGGCTGCCAAAATACTGATAGAAGAAAGCCAAGATGCCCCAGACCATAG
         GTGAGACCTACACCGACGGTTTTATGACTATCTTCTTTCGGTTCTACGGGGTCTGGTATC

++++++++++++++++++++++++++++++++++++++++++++++++++++++++++++
                                        E2FB
         ==========>   ==============================>

***********************************************************
         rLysPheLysThrLysValArgArgLeuTyrAspIleAlaAsnValLeuThrSerLeuAl
 1201    TAAATTTAAAACAAAGGTACGACGCCTCTATGACATAGCCAATGTTCTGACCAGCTTGGC
         ATTTAAATTTTGTTTCCATGCTGCGGAGATACTGTATCGGTTACAAGACTGGTCGAACCG

++++++++++++++++++++++++++++++++++++++++++++++++++++++++++++ exon7
         ***********************************************************
         aLeuIleLysLysValHisValThrGluGluArgGlyArgLysProAlaPheLysTrpIl
 1261    TCTGATAAAGAAAGTGCATGTAACAGAAGAGCGAGGTCGTAAACCAGCCTTCAAGTGGAT
         AGACTATTTCTTTCACGTACATTGTCTTCTCGCTCCAGCATTTGGTCGGAAGTTCACCTA

++++++++++++++++++++++++++++++++++++++++++++++++++++++++++++

===============================
```

FIGURE 2 - Sheet 4

```
                    **************************>
       eGlyProValAspPheSerSerSerAspGluGluLeuValAspValSerAlaSerValLe
 1321  CGGGCCTGTGGACTTCAGCTCAAGTGATGAAGAACTGGTGGATGTTTCTGCATCTGTCTT
       GCCCGGACACCTGAAGTCGAGTTCACTACTTCTTGACCACCTACAAAGACGTAGACAGAA

+++++++++++++++++++++++++++++++++++++++++++++++++++++++++++
                                                               exo
       =========================================================== uProGluLeuLysArgGluThrTyrGlyGlnIleGlnValCysAlaLysGlnLysLeuAl
 1381  ACCAGAATTGAAAAGAGAAACATATGGCCAGATTCAAGTCTGTGCAAAACAGAAGCTGGC
       TGGTCTTAACTTTTCTCTTTGTATACCGGTCTAAGTTCAGACACGTTTTGTCTTCGACCG

+++++++++++++++++++++++++++++++++++++++++++++++++++++++++++
       n8
       =========================================================== aArgHisGlySerPheAsnThrValGlnAlaSerGluArgIleGlnArgLysValAsnSe
 1441  TCGCCATGGTTCTTTTAACACAGTTCAGGCTTCTGAGAGGATCCAGAGGAAAGTGAACTC
       AGCGGTACCAAGAAAATTGTGTCAAGTCCGAAGACTCTCCTAGGTCTCCTTTCACTTGAG

+++++++++++++++++++++++++++++++++++++++++++++++++++++++++++

==============================>
                    **************************
       rGluProSerSerProTyrArgGluGluGlnGlySerGlyGlyTyrSerLeuGluIleGl
 1501  AGAACCGAGCAGCCCGTACAGAGAAGAACAAGGATCAGGTGGCTACTCTTTAGAAATTGG
       TCTTGGCTCGTCGGGCATGTCTCTTCTTGTTCCTAGTCCACCGATGAGAAATCTTTAACC
                                      ORF
       +++++++++++++++++++++++++++++++++++++++++++++++++++++++++++

=================
         exon9
       ******************************************>
       ySerLeuAlaAlaValTyrArgGlnLysIleGluAspAsnSerGlnGlyLysAlaPheAl
 1561  AAGCCTGGCAGCTGTCTATAGACAGAAAATAGAAGACAATTCACAGGGAAAAGCCTTTGC
       TTCGGACCGTCGACAGATATCTGTCTTTTATCTTCTGTTAAGTGTCCCTTTTCGGAAACG

+++++++++++++++++++++++++++++++++++++++++++++++++++++++++++

=========================================================== aSerLysArgValValProProSerSerSerLeuAspProValAlaProPheProValIe
 1621  CAGTAAGAGAGTGGTGCCTCCATCAAGCAGCTTGGACCCTGTTGCTCCTTTCCCTGTCCT
       GTCATTCTCTCACCACGGAGGTAGTTCGTCGAACCTGGGACAACGAGGAAAGGGACAGGA

+++++++++++++++++++++++++++++++++++++++++++++++++++++++++++

=========================================================== uSerValAspProGluTyrCysValAsnProLeuAlaHisProValPheSerValAlaGl
 1681  CTCTGTTGACCCAGAATATTGTGTTAATCCTTTAGCCCACCCAGTATTTTCTGTTGCTCA
       GAGACAACTGGGTCTTATAACACAATTAGGAAATCGGGTGGGTCATAAAAGACAACGAGT

+++++++++++++++++++++++++++++++++++++++++++++++++++++++++++

=========================================================== nThrAspLeuGlnAlaPheSerMetGlnAsnGlyLeuAsnGlyGlnValAspValSerLe
 1741  GACGGACCTGCAGGCATTCTCCATGCAGAACGGTCTGAATGGACAAGTGGATGTCTCACT
       CTGCCTGGACGTCCGTAAGAGGTACGTCTTGCCAGACTTACCTGTTCACCTACAGAGTGA
```

FIGURE 2 - Sheet 5

```
       ++++++++++++++++++++++++++++++++++++++++++++++++++++++++++++
                                                             exon10
       ============================================================ uAlaSerAlaAlaSerAlaValGluSerLeuLysProAlaLeuLeuAlaGlyGlnProLe
 1801  TGCTTCTGCAGCCTCTGCTGTGGAGAGCCTGAAGCCAGCACTCCTTGCTGGCCAGCCTCT
       ACGAAGACGTCGGAGACGACACCTCTCGGACTTCGGTCGTGAGGAACGACCGGTCGGAGA

++++++++++++++++++++++++++++++++++++++++++++++++++++++++++++
       ============================================================ uValTyrValProSerAlaSerLeuPheMetLeuTyrGlySerLeuGlnGluGlyProAl
 1861  AGTGTATGTGCCCTCTGCCTCACTGTTCATGCTGTATGGAAGTCTGCAGGAGGGACCAGC
       TCACATACACGGGAGACGGAGTGACAAGTACGACATACCTTCAGACGTCCTCCCTGGTCG

++++++++++++++++++++++++++++++++++++++++++++++++++++++++++++
       ============================================================ aSerGlySerGlySerGluArgAspAspArgSerSerGluAlaProAlaThrValGluLe
 1921  GTCAGGGTCAGGGTCAGAGAGGGATGACAGAAGCTCAGAAGCCCCAGCCACAGTAGAGCT
       CAGTCCCAGTCCCAGTCTCTCCCTACTGTCTTCGAGTCTTCGGGGTCGGTGTCATCTCGA

++++++++++++++++++++++++++++++++++++++++++++++++++++++++++++
       ============================================================ uSerSerAlaProSerAlaGlnLysArgLeuCysGluGluArgLysProGlnGluGluAs
 1981  GTCATCTGCACCCTCAGCTCAGAAGCGCCTCTGTGAGGAGAGGAAACCTCAGGAGGAGGA
       CAGTAGACGTGGGAGTCGAGTCTTCGCGGAGACACTCCTCTCCTTTGGAGTCCTCCTCCT

++++++++++++++++++++++++++++++++++++++++++++++++++++++++++++
       ============================================================ pGluProAlaThrLysArgGlnSerArgGluTyrGluAspGlyProLeuSerLeuValMe
 2041  TGAGCCAGCCACTAAAAGGCAAAGTAGGGAATATGAAGACGGCCCGCTGTCGCTTGTCAT
       ACTCGGTCGGTGATTTTCCGTTTCATCCCTTATACTTCTGCCGGGCGACAGCGAACAGTA

++++++++++++++++++++++++++++++++++++++++++++++++++++++++++++
       =====>
                 ************************************************
       tProLysLysProSerAspSerThrAspLeuAlaSerProLysThrMetGlyAsnArgAl
 2101  GCCCAAGAAACCCTCAGATTCCACAGACCTTGCCTCTCCCAAGACTATGGGTAACAGGGC
       CGGGTTCTTTGGGAGTCTAAGGTGTCTGGAACGGAGAGGGTTCTGATACCCATTGTCCCG

++++++++++++++++++++++++++++++++++++++++++++++++++++++++++++

************************************************************
       aSerIleProLeuLysAspIleHisValAsnGlyGlnLeuProAlaAlaGluGluIleSe
 2161  ATCTATACCCCTCAAAGACATTCATGTGAATGGCCAACTCCCTGCTGCAGAAGAGATTTC
       TAGATATGGGGAGTTTCTGTAAGTACACTTACCGGTTGAGGGACGACGTCTTCTCTAAAG

++++++++++++++++++++++++++++++++++++++++++++++++++++++++++++
```

FIGURE 2 - Sheet 6

```
                    exon11
         *******************************************************
         rGlyLysAlaThrAlaAsnSerLeuValSerSerGluTrpGlyAsnProSerArgAsnTh
    2221 AGGAAAGGCAACAGCAAACTCTCTTGTTTCTTCTGAGTGGGGAAATCCTTCAAGAAATAC
         TCCTTTCCGTTGTCGTTTGAGAGAACAAAGAAGACTCACCCCTTTAGGAAGTTCTTTATG

+++++++++++++++++++++++++++++++++++++++++++++++++++++++++++

*******************************************************
         rAspValGluLysProSerLysGluAsnGluSerThrLysGluProSerLeuLeuGlnTy
    2281 AGATGTTGAAAAGCCTTCAAAAGAAAATGAAAGCACCAAAGAGCCTTCTTTGCTACAATA
         TCTACAACTTTTCGGAAGTTTTCTTTTACTTTCGTGGTTTCTCGGAAGAAACGATGTTAT

+++++++++++++++++++++++++++++++++++++++++++++++++++++++++++
         ============================================================

*********************>
         rLeuCysValGlnSerProAlaGlyLeuAsnGlyPheAsnValLeuLeuSerGlySerGl
    2341 TCTTTGTGTGCAGTCTCCTGCAGGATTAAATGGTTTCAATGTACTTTTATCTGGCAGTCA
         AGAAACACACGTCAGAGGACGTCCTAATTTACCAAAGTTACATGAAAATAGACCGTCAGT

+++++++++++++++++++++++++++++++++++++++++++++++++++++++++++
         ============================================================ nThrProProThrValGlyProSerSerGlyGlnLeuProSerPheSerValProCysMe
    2401 AACCCCCCCTACTGTGGGCCCGTCCTCAGGTCAGCTGCCGTCTTTCAGTGTCCCTTGCAT
         TTGGGGGGGATGACACCCGGGCAGGAGTCCAGTCGACGGCAGAAAGTCACAGGGAACGTA

+++++++++++++++++++++++++++++++++++++++++++++++++++++++++++
         ============================================================ tValLeuProSerProProLeuGlyProPheProValLeuTyrSerProAlaMetProGl
    2461 GGTCTTACCATCTCCACCTCTGGGCCCTTTTCCTGTTCTCTATTCTCCTGCAATGCCGGG
         CCAGAATGGTAGAGGTGGAGACCCGGGAAAAGGACAAGAGATAAGAGGACGTTACGGCCC

+++++++++++++++++++++++++++++++++++++++++++++++++++++++++++
                                                              exon12
         ============================================================ yProValSerSerThrLeuGlyAlaLeuProAsnThrGlyProValAsnPheSerLeuPr
    2521 CCCGGTTTCTTCCACTCTTGGTGCTCTCCCAAACACAGGACCTGTGAATTTCAGCTTGCC
         GGGCCAAAGAAGGTGAGAACCACGAGAGGGTTTGTGTCCTGGACACTTAAAGTCGAACGG

+++++++++++++++++++++++++++++++++++++++++++++++++++++++++++
         ============================================================ oGlyLeuGlySerIleAlaGlnLeuLeuValGlyProThrAlaValValAsnProLysSe
    2581 TGGCCTTGGATCAATAGCCCAGCTTCTCGTCGGCCCCACAGCTGTGGTTAATCCAAAGTC
         ACCGGAACCTAGTTATCGGGTCGAAGAGCAGCCGGGGTGTCGACACCAATTAGGTTTCAG

+++++++++++++++++++++++++++++++++++++++++++++++++++++++++++
         ============================================================ rSerThrLeuProSerAlaAspProGlnLeuGlnSerGlnProSerLeuAsnLeuSerPr
```

FIGURE 2 - Sheet 7

```
2641 GTCCACACTCCCTTCTGCAGACCCTCAGCTTCAGAGTCAGCCCTCACTAAACCTAAGTCC
     CAGGTGTGAGGGAAGACGTCTGGGAGTCGAAGTCTCAGTCGGGAGTGATTTGGATTCAGG

++++++++++++++++++++++++++++++++++++++++++++++++++++++++++++

============================================================ oValMetSerArgSerHisSerValValGlnGlnProGluSerProValTyrValGlyHi
2701 AGTGATGTCAAGGTCACACAGTGTCGTCCAACAACCTGAGTCCCCCGTTTACGTGGGACA
     TCACTACAGTTCCAGTGTGTCACAGCAGGTTGTTGGACTCAGGGGGCAAATGCACCCTGT

++++++++++++++++++++++++++++++++++++++++++++++++++++++++++++

=========================>

******************************
     sProValSerValValLysLeuGlnGlnSerProValProValThrProLysSerIleGl
2761 TCCAGTCTCAGTAGTAAAATTACAACAGTCACCAGTTCCAGTGACCCCCAAGAGCATCCA
     AGGTCAGAGTCATCATTTTAATGTTGTCAGTGGTCAAGGTCACTGGGGGTTCTCGTAGGT

++++++++++++++++++++++++++++++++++++++++++++++++++++++++++++

************************************************************
     nArgThrHisArgGluThrPhePheLysThrProGlySerLeuGlyAspProValLeuLy
2821 ACGCACACATCGTGAGACGTTTTTCAAGACACCCGGCAGCCTTGGAGACCCTGTCCTGAA
     TGCGTGTGTAGCACTCTGCAAAAAGTTCTGTGGGCCGTCGGAACCTCTGGGACAGGACTT

++++++++++++++++++++++++++++++++++++++++++++++++++++++++++++

************************************************************
     sArgArgGluArgAsnGlnSerArgAsnThrSerSerAlaGlnArgArgLeuGluIlePr
2881 GAGAAGAGAAAGGAACCAGTCACGAAACACCAGCTCGGCCCAGAGGAGACTAGAAATCCC
     CTCTTCTCTTTCCTTGGTCAGTGCTTTGTGGTCGAGCCGGGTCTCCTCTGATCTTTAGGG

+++++++++++++++>

************************************************************
     oSerGlyGlyAlaAsp---                                              (SEQ ID NO:09)
2941 CAGCGGCGGCGCTGACTAACCTGCCGCTTTGCCAGGTGGGGGTGGGATCAAACGCCCTGA
     GTCGCCGCCGCGACTGATTGGACGGCGAAACGGTCCACCCCCACCCTAGTTTGCGGGACT

************************************************************
3001 GAGTCCCGGATGTCCGAGGCGGGATGCAAACCATCCCGTCCTGAGCACGGGTCCTTCCTC
     CTCAGGGCCTACAGGCTCCGCCCTACGTTTGGTAGGGCAGGACTCGTGCCCAGGAAGGAG

************************************************************
3061 TCTCTTTCATCCACACTTCTGTTAACTTCCCACCACCATCAATCATCTGATTTCCTGAAA
     AGAGAAAGTAGGTGTGAAGACAATTGAAGGGTGGTGGTAGTTAGTAGACTAAAGGACTTT

************************************************************
3121 GTAATTAATTGTGCATTTAATACCAGTTAGAGTTCCGACTCTGCATGGTGTCACAGTGAA
     CATTAATTAACACGTAAATTATGGTCAATCTCAAGGCTGAGACGTACCACAGTGTCACTT

************************************************************
3181 AGCGCCGACTGACTTATGGTTTTGATTCAAGAATCGTCTTATTGCTGGAAGTAGATCTGA
     TCGCGGCTGACTGAATACCAAAACTAAGTTCTTAGCAGAATAACGACCTTCATCTAGACT
```

FIGURE 2 - Sheet 8

```
3241 ATAGGCTACCGGAGCCTTGTTTTTCTAAAGGGGGCGCTGTCTAGCACTTAACTAGGGTA
     TATCCGATGGCCTCGGAACAAAAAGATTTCCCCCCGCGACAGATCGTGAATTGATCCCAT

3301 AGCATTCTTAACATGTATTTCCACTTGCCCTGAGTAAATCTGTGGTGAGAGAAGCTTCCT
     TCGTAAGAATTGTACATAAAGGTGAACGGGACTCATTTAGACACCACTCTCTTCGAAGGA

3361 TTCTGCAGTTTAAAAAAGCTACTGCTTCCTTAGGCTTCATCAGGAAGCCACCTTCAGTTG
     AAGACGTCAAATTTTTTCGATGACGAAGGAATCCGAAGTAGTCCTTCGGTGGAAGTCAAC

3421 TGAATCCTATGGTGTTATTTATTTTGTTCCTGAAATGGGATTTAGTGCAAAAAGTTTACA
     ACTTAGGATACCACAATAAATAAAACAAGGACTTTACCCTAAATCACGTTTTTCAAATGT

3481 ACTACAGTCTTTAACACATTTTTTTCAGGGTATGACGACTTGAATGTTTATACTTTTATT
     TGATGTCAGAAATTGTGTAAAAAAAGTCCCATACTGCTGAACTTACAAATATGAAAATAA

3541 CTATAATTTGCCCTGCACTTATTTTACAACCTAGTAATAATGTGGATAAATGTATCTACA
     GATATTAAACGGGACGTGAATAAAATGTTGGATCATTATTACACCTATTTACATAGATGT

3601 TGACACATGTCAAGACCAAAATAACTGTGAATGACACACCTTGCTGTAAATGAACTGTGC
     ACTGTGTACAGTTCTGGTTTTATTGACACTTACTGTGTGGAACGACATTTACTTGACACG

3661 TAACCCTGACTGTGGGCTTGAGAACAAAGATGAACTCTAGAACTCTAGCAGCCTAACTGC
     ATTGGGACTGACACCCGAACTCTTGTTTCTACTTGAGATCTTGAGATCGTCGGATTGACG

3721 TGCTTCTCAAATAACTGTGTGAACAGTGAGATATTACTGTTTGTTTCTAAAAATCCTACT
     ACGAAGAGTTTATTGACACACTTGTCACTCTATAATGACAAACAAAGATTTTTAGGATGA

3781 GTGCCCAGTTTCCTTCACTACATGCCCTGCATTTTTTATTTAAATATTTAGCTGTAGCGC
     CACGGGTCAAAGGAAGTGATGTACGGGACGTAAAAAATAAATTTATAAATCGACATCGCG

3841 CATCAGATATGGATGCCTTCTAACAATTGCTGTTTGTAAAATAAATCAGGATGGTAGAAA
     GTAGTCTATACCTACGGAAGATTGTTAACGACAAACATTTTATTTAGTCCTACCATCTTT

3901 GTGATTATATGGAAAATTGGAACCTGGATGAGACCTTTTCGTTGAATTCTGAAGAGTAAT
     CACTAATATACCTTTTAACCTTGGACCTACTCTGGAAAAGCAACTTAAGACTTCTCATTA

3961 GATGTGAAAATTGATACAGGGCAAGAGATGATTCTTTTGTTTTTCTTCTACTTCATGTCC
     CTACACTTTTAACTATGTCCCGTTCTCTACTAAGAAAACAAAAAGAAGATGAAGTACAGG

4021 AGAAGAGTAAGAGGGAAAATGGACATATGTTTCATATCCAAGGGTATTCAAACTGTAGTT
     TCTTCTCATTCTCCCTTTTACCTGTATACAAAGTATAGGTTCCCATAAGTTTGACATCAA

4081 AGTTGGTACCTCTGAAAAATGAGAATGGTGAGCGCACGGGTTGGTTGTTCTAGCATGAAT
     TCAACCATGGAGACTTTTTACTCTTACCACTCGCGTGCCCAACCAACAAGATCGTACTTA
```

FIGURE 2 - Sheet 9

```
     **************************************************************
4141 ACAATTCTGGAAACTGTTATGCAATTTCCCTTTTTTAACCCACACATTACTTTAGGGGTGCA
     TGTTAAGACCTTTGACAATACGTTAAAGGGAAAAAATTGGGTGTAATGAAATCCCCACGT exon13
     **************************************************************
4201 TTAAGTCGCCAAACTATACTAGTTCTTTGTATTCCTAGACTTGCTGATATTTACCTCTCT
     AATTCAGCGGTTTGATATGATCAAGAAACATAAGGATCTGAACGACTATAAATGGAGAGA

**************************************************************
4261 CTTGTCTCTTCAGAGTAAATGGTTCCCTTCTTTCCTTCCTACTTTCCTTCATTCTCTCTT
     GAACAGAGAAGTCTCATTTACCAAGGGAAGAAAGGAAGGATGAAAGGAAGTAAGAGAGAA

**************************************************************
4321 CCTTCCCTCCTTCCTACTTCTTTTCTTCCTTCCTCTTCCTCTCTTAAAACTATCTTAGAT
     GGAAGGGAGGAAGGATGAAGAAAAGAAGGAAGGAGAAGGAGAGAATTTTGATAGAATCTA

**************************************************************
4381 GTAGAATCCTGGTGTAGGGTTTTATTTTATTTTTATTTTTTGACCCAATAAAATGTTATA
     CATCTTAGGACCACATCCCAAAATAAATAAAAATAAAAAACTGGGTTATTTTACAATAT

**************************************************************
4441 TGAAAGAATGAAAATATTAATTTAAGAGACTCTGGGAGTCTGAATAAAGTAGCTTTATAT
     ACTTTCTTACTTTTATAATTAAATTCTCTGAGACCCTCAGACTTATTTCATCGAAATATA

**************************************************************
4501 TAACTACAGGATAATATTAGCCTTATTACCCCCACAAGATTTTTTAAAACTTGAGGTAGG
     ATTGATGTCCTATTATAATCGGAATAATGGGGGTGTTCTAAAAAATTTTGAACTCCATCC

**************************************************************
4561 TAGCTACATTAAATAAATTTGCTACTTATATAAAAATTTTTATCAACACTAAACTTTTAA
     ATCGATGTAATTTATTTAAACGATGAATATATTTTTAAAAATAGTTGTGATTTGAAAATT

**************************************************************
4621 AGTTTACAAGTTTTTTTTTCTTTTTTACAGTCTTCTATAGAGTTAGGTTAAAAATGTGG
     TCAAATGTTCAAAAAAAAAGAAAAAATGTCAGAAGATATCTCAATCCAATTTTTACACC

**************************************************************
4681 TTCTAACCATCAACAATTGCATGGTTAAATGACCCTGAACTAAAACTGATGGGTTCCCTA
     AAGATTGGTAGTTGTTAACGTACCAATTTACTGGGACTTGATTTTGACTACCCAAGGGAT

**************************************************************
4741 TCAAAACAAATAAAAATATACCTTTTTCAGGTTTCAATCTGTGCAGGGTATATGCATGTT
     AGTTTTGTTTATTTTTATATGGAAAAAGTCCAAAGTTAGACACGTCCCATATACGTACAA

**************************************************************
4801 AATTCTACCATGCTTAAGAACTTCCACAAAATATTTCATGGAGAGGTCTGCATTTAGACG
     TTAAGATGGTACGAATTCTTGAAGGTGTTTTATAAAGTACCTCTCCAGACGTAAATCTGC

**************************************************************
4861 GAAACAGAAATTGCTTTTCCCCTCACTGTTCCTGAATGCTCTATACTTGTTTTAACATTT
     CTTTGTCTTTAACGAAAAGGGGAGTGACAAGGACTTACGAGATATGAACAAAATTGTAAA

**************************************************************
4921 TTGCTATCTTTTTTTATTATTCTGATCATGATATGACCATTTAACCTCAGAATTCATAAT
     AACGATAGAAAAAAATAATAAGACTAGTACTATACTGGTAAATTGGAGTCTTAAGTATTA

**************************************************************
4981 TCCTGAGGGGTGTTAAGAAGCAGTCCCATTGGTGAGGATATTATGACTTGGTGACCATTC
     AGGACTCCCCACAATTCTTCGTCAGGGTAACCACTCCTATAATACTGAACCACTGGTAAG
```

FIGURE 2 - Sheet 10

```
     ************************************************************
5041 TTAGGAGTAGAAAACCAAGGACAATTGCTTCTGTATTCAGTATCCACTTCTTAATGTGGC
     AATCCTCATCTTTTGGTTCCTGTTAACGAAGACATAAGTCATAGGTGAAGAATTACACCG

************************************************************
5101 TTTATATGTAAAAATAATAATGCAGTGGTTGTTTCTGTCAGGAAAATAAATCTTACAGAA
     AAATATACATTTTTATTATTACGTCACCAACAAAGACAGTCCTTTTATTTAGAATGTCTT

************************************************************
5161 CAACTGGTGGAATTGAAGCTGCTGCGCTAGACTTGGATATTTTGGGTAGTGAAGAAGCAA
     GTTGACCACCTTAACTTCGACGACGCGATCTGAACCTATAAAACCCATCACTTCTTCGTT

************************************************************
5221 TGGCAATCTTGAGTCTATTATTGTATAATTTAGTAAAAGAAAAAAATAATCGTTGGTGGT
     ACCGTTAGAACTCAGATAATAACATATTAAATCATTTTCTTTTTTATTAGCAACCACCA

************************************************************
5281 CCTACTAAGAGAATGCAGCTTTTTTGAGTTGTCACAGAGGCTGTGTGTGCCCTACACTGA
     GGATGATTCTCTTACGTCGAAAAAACTCAACAGTGTCTCCGACACACACGGGATGTGACT

************************************************************
5341 CCAGGGTTTGTAAAACCCTTTCATTCTGGTACAAGAGTCGGGGGTATAACTTTTATACTT
     GGTCCCAAACATTTTGGGAAAGTAAGACCATGTTCTCAGCCCCCATATTGAAAATATGAA

************************************************************
5401 GAATCTACCTACCAAGTTTACATTTCTCAATTCCTTTTTGTAAGGTGCTATTTCTGTATT
     CTTAGATGGATGGTTCAAATGTAAAGAGTTAAGGAAAAACATTCCACGATAAAGACATAA

************************************************************
5461 TAAATAACTTTCTTTTAACGTAAAGCTGCTTTCTGCTTATCTTATTGCACTGCTAGTTGT
     ATTTATTGAAAGAAAATTGCATTTCGACGAAAGACGAATAGAATAACGTGACGATCAACA

************************************************************
5521 ATGTAGGTATTAATTTTATTGCTGCTTACTGCTTTTGTTTTCTTATTATTTAGCTCTGCT
     TACATCCATAATTAAAATAACGACGAATGACGAAAACAAAAGAATAATAAATCGAGACGA

************************************************************
5581 CTTTTTCCTAATGGCTATATTATCTATAGCTATTTACTTGTAACTGTACTACATGTAAAC
     GAAAAAGGATTACCGATATAATAGATATCGATAAATGAACATTGACATGATGTACATTTG

************************************************************
5641 TGATTTTTTGTTCTGATTTTTTTTCTAATATTTTTAGGAAAATATTAAGCTTTATAAAAT
     ACTAAAAAACAAGACTAAAAAAAAGATTATAAAAATCCTTTTATAATTCGAAATATTTTA
                            (SEQ ID NO:09)
     *********************>
5701 AGCAATAAAAAATAATTCATTTAA (SEQ ID NO:08)
     TCGTTATTTTTTATTAAGTAAATT
```

Figure 3

Amino Acid Sequence of F13H (SEQ ID NO:11)

MENEKEN LFCEP HKRGLMKT PLKESTT ANIVLAEI QPDFGPLTTPTK PKEGSQGEPWTPT
ANLKMLI SAVSP EIRNRDQKRGLFDNR SGLPEAKDCI HEHLSGDEFE KSQPSRKEKS LGL
LCHKFLA RYPNY PNPAVNND ICLDEVA EELNV ERRRI YDI VNVLESL HMVSR LAKNR YTW
HGRHNLN KTLGT LKS IGEEN KYAEQ IMMI KKK EYEQE FDF IKSYS IED HII KSNTGPNGH
PDMCFVE LPGVE FRAAS VNS RKDKSLR VMSQK FVMLFLVSTPQI VSL EVAAK ILIGE DHV
EDLDKSK FKTKI RRLYD IAN VLSSLDL IKKVH VTEERGRK PAFKWTG PEISPNTSGS SPV
IHFTPSD LEVRR SSKEN CAKNLFSTRG KPNFT RHPSLI KLVKSI ESD RRKINSAPSS PIK
TNKAESS QNSAP FPSKMAQLAA ICKMQ LEEQS SESRQKVRVQLARSG PCKPVAPLDP PVN
AEMELTA PSLIQ PLGMV PLI PS PLSSA VPLIL PQAPSGPS YAIYLQP TQAHQ SVTPPQGL
SPTVCTT HSSKATGSKD STDATTEKAANDTSKASA STRPGSLLPAPE RQGAKSRTRE PAG
ERGSKRA SMLED SGSKKKFKEDLKGLENVSATLFPSGYLI PLTQCSS LGAES ILSGKENS
SALSPNH RIYSS PIAGV IPVTS SELTA VNFPS FHVTPLKLMVSPTSV AAVPVGNSPALAS
SHPVPIQNPSSA IVNFT LQHLGLI SPNVQLSASPGSGI VPVSPRIES VNVAPENAGTQQG
RATNYDS PVPGQ SQPNGQSVAVTGAQQ PVPVT PKGSQLVAESFFRTPGGPTKPTSSS CMD
FEGANKT SLGTL FVPQR KLEVSTEDVH

Figure 4 cDNA sequence of F13H (SEQ ID NO:10)

```
attgggcaaatacagccttccaaggtggagtctaacgccgtggtgtgaactggccacccgaacagggag
taaatagtgctttgtatctttaaggaagccctttttaaatttaaaaaaaagtcttaattataagact
ctttaaatgcccaactgcatacttggagctttgggactgaatttggaactttcctgtcaagcgacctcc
cacgacttactgctgagcctgtgcacgtgtgtgtaaggggagaaatccaggcatctagatgcagactt
gtacccagttacttggggtcgcgtgcgctcagctgggacctgggctcgtgcgcttagtccggagccctg
atctgcgaacaggatattaaaacttttagtacaattgattggactacttgaaccatcgggatttgggga
ggaactccagattttttcattttttaaactctaaatgtatgaggaatttacagaatggagaacgaaaagga
aaatctcttttgtgagccacataaaaggggactaatgaaaacacctctgaaagaatccaccacagcaaa
tatcgtgttggcagagatccagcctgactttggcccttaaccacacctaccaagcccaaggaaggctc
tcagggagagccgtggacaccgacagccaacctgaaaatgctcatcagtgctgtgagccctgagatccg
caacagagatcagaaaggggtttgtttgacaacagaagtggattacctgaggccaaagactgtataca
cgaacacttatctggagatgaatttgagaaatcccaaccaagtcgaaagagaaaagtttaggattatt
gtgtcataagttcttagcacgatatcctaattatcccaaccctgctgtgaataatgacatctgccttga
cgaagtggcagaggaacttaatgttgaacgtcgacgcatttacgatatcgtgaacgtcctagagagtt
acatatggtgagccgcctcgccaaaaacaggtacacttggcacgggcgacacaatctcaacaaaaccct
tggcaccttgaagagcatcggggaggagaataagtacgccgagcagattatgatgatcaaaagaaaga
atatgagcaagagtttgactttattaagagttacagtatagaggatcatatcatcaaatcaaacactgg
cccaaatggacacccagacatgtgttttgtggaactccctggagtggaatttcgggcagcttctgtaaa
cagccgcaaagacaagtctttaagggtaatgagccagaaatttgtgatgctgttttttggtgtcaacgcc
tcagatagtaagcctagaagttgctgccaagatttttaattggggaggaccatgtggaagatttggataa
aagcaagtttaaaacaaaaattaggaggttgtatgatatagctaatgttctgagtagcctggatcttat
caagaaagttcatgttacagaggaaagaggccgaaaaccagctttcaaatggaccggcccagaaatcag
tccaaataccagtggctccagcccagtcattcattttactccctctgatttggaggtgagacggtcttc
aaaagagaactgtgccaaaaacctcttttccacacgtgggaaaccaaacttttactcgacacccatctct
tatcaaattggtaaagagtatagaaagtgatcggagaaagataaattctgcgcccagtagccctatcaa
gaccaacaaagctgagagttctcagaattctgcaccccttcccaagtaaaatggctcagctcgcagctat
ttgtaaaatgcagttagaagagcaatcaagtgaatccagacagaaagtgaaagtacagctggcaagatc
tggaccctgcaaaccagtagcccctctggaccccccagtgaatgctgagatggagctgacagcaccgtc
cctcatccagccctgggaatggttcccctgatccccagcccccttgtcatcagcagtgccctgatcct
acctcaggcccttcaggcccatcctatgccatctacctgcagcccactcaagcccaccaaagtgtgac
gccaccccaaggcctgagcccaacggtgtgcaccaccccactcttctaaagctactggctcaaaagactc
cacagatgccaccactgagaaggcagccaatgatacctcaaaggccagtgcctctaccaggcctggaag
cttgctgccagcaccagagaggcaaggggcaaagagccgaaccagggagccagctggagaaagaggctc
aaagagggcaagcatgctcgaggacagtggttccaaaaagaaatttaaagaggacctaaaaggacttga
aaatgtctccgcaaccttgttcccatcaggatacctaatccctctcacgcagtgctcatccctggggc
agagtccattttgtctggtaaagaaaactcaagtgctctttccccaaaccacaggatttacagctcccc
aattgcaggtgttattccagtgacatcatctgaactcactgctgttaattttccctcttttcatgtaac
accgttgaagctaatggtctcaccaacttccgtggcagccgtacctgtcgggaacagcccggctctcgc
ttcaagccaccctgttcccatccagaacccaagctcagccattgtaaacttcaccctgcagcacctggg
actcatctcacccaatgtgcagttgtctgccagccctgggtctggaatcgttcctgtgtctccaagaat
agagtctgttaatgtcgcaccagaaaatgcaggcactcagcaaggaagggccaccaactatgactcacc
agtcccaggccagagccagccaaatggacaatcagttgctgtgacaggggcacaacagcctgttcctgt
gacacccaaagggtcacaattagtggccgaaagtttcttccgtacccaggtggacccaccaagccaac
cagctcatcctgcatggattttgagggtgctaataaaacctccttaggaactctcttttgtcccacagcg
aaaactggaagtctcaacagaggatgtccattaatcaacagatgttgrcttagtttaayttttctaaaga
gttgtttaatagagaaaatgtacacagactgatttggagaacacattctctgaaaatactgtaaatacg
ttggggatttgttcaatgtgaaatcagatagttgttttcatacatatatatataayacacacacacacac
acacacacacacayatatatttgtataaagctaagtttagctttcaatcctacaaaataaaagtaaaat
gttgaactctaagatatattaacttctaggggggaaaaatccattatttagctatgcctatactattat
gcaaagtaactgtattaaagtttacttccctctaagcaaatatgcttgacatgcctaacacagcattcc
cttaaacattttgcacaaagaaaatgctgtgtgatgtataatgttgtatttttaaatagggtatagct
atattttttgtaattctttaatctgtgttgcagtgtatcttttgtaaagtttgcaacaatcctcaa
tcaagtctatggaaaaattatttataaaatgtattttaatcataagttgttcaaattaaaactttttct
```

Figure 5-Sheet 1

F13H genomic sequence (SEQ ID NO:12):

```
ggtaactgtc actcagacat ctgcagcatg aatggccctg tagatcacag atttgaacga
attagtcact atctctgaac acaggtgcat gaggcagact gcttctaaag aactttaaaa
gggatttatg gcccacagga ctccggggct gtaataactt cgggtacatt aggcatagct
gaatctatgc actcttggga gcgctgacca ttcaggcggt tgggggagat gacaatctgg
ccaacagcta gtggctaaag cagaagcacc aactccccac tttttgttga tacatttaga
acccagtctt gctccaaaaa aggggtacct gggcttagta agaaccagcc gctcagtgct
agcaacggtg aaccctata tagtgacctc tgctttattt caaatctgcg agccacaggc
agtggcccct ctgcacagta cctgaaaggc ctgctttcag gtcgaagcgc cttcttgagc
aagacctgca cctcagctgg cgacgaaagg gggacaggga cacgacggcg ccaacattcc
agggcggcca caccgcaagc ctgcggtcgc gttccgcggg gagatgagcc ttcgctcgcc
acggagaccc ctggccctat ggccggcagc tgctgcgctg cgacccagc ctcaatatca
tagcatcccc gccctcatcg cgtttcgcag aaaataaaaa tgcctcgccc tgctagtcag
caatgggaga gtcactgatc cccaagttag cggtgggagt gggaagtgt ggccccgggc
cctgctggag cctaaagaca cgcgattaca gaggaggacg agccaaaccg agtccagatc
gagagaccgg cgcccagatc tcggcgcggt tgggcaacac tcagcaccag tccgcagaaa
agtctaaggc agaggagagc aagggagcc aacgcgggcg caaatgatcc aggtgcagcc
gaggcagcgc cgccgccccg ggcctcggtg tcccgttctg caaagtgagg acgaaggatc
gaagtgtctc cccgaccctg ctagggctct acagggaacc aggctaaagc tgcctgaggc
tcggagaccg gaaaagagg gaaagacaac agggaagaga aagggaggag tgggtgggag
accctgagga aagacggcga ggacagggtt ggagggtttt ccgccttcct cctcttcctc
ctacacctga gttctcaccg ctgggccaag gcccagagcc cacggagctt aggcaccagt
agccaagctt ctccctcctc gcgccagttt ctgcgaggca cggggcagac ggtgggcagc
acaatcatgc atgccagggg tgcaaggggg agaggtccgg ctggagtccg agggcaggtg
agccggcctg ggctgggca ggggtgagat agccccaagc ggggaatcgc agggcgcctg
cggcccagcc cgcgagcccc ggacgggcca aattttattc cccaactttg agcaagggga
gggggtgtat gcaaaaaaaa aaaaaaagga aaaaaaagtt gctgaacttt tcccccaact
ctgccgtaga ggcgggagtg gagggcggtg cctgcaccga ttcgccggcg ctacggtcg
ggaggctcgg attggcgctc ggggccgggg gccggggcga gcgggcgtgg gggaggggag
cggccctccc cgcccgcggt atcggctcgc gccgggagcg ggttaatttc aaatcggggg
cttggctgct cctggacggt cacgctccct ctgcccgcca gccggcccgc cagtcccggt
cccggcgtct ctctccggca cccacctcgg cgctgcggaa agactgactg ccaggtacgc
gggctcccgg gcctgagagg ggcagcggtg ctgacgagtc ccggctcagc ccccgccggc
tcccgccgtg aggtggactg acaggtcagc gggacgcaga ggggcgcggc gcccgggcga
cacggcaccg ggagagggct cgggagggtg gcggcggcgg cggcggcggc cgtttcccgc
ctcccgcttc gccgggggcc gtgagggagg agctgagctc ccgcgcagag gggcggggggc
gaacgagggg gaggggcggg gttgccgtgg ttccgggcgc gggtttgccc gcgctcaggc
cccgcgcagc taaggggagg cgccggccac ggtccgactt ccgcgccaa attttaaat
cgaaggcgga aggtccggcc ccgcccctgg cgccgtcggc caatcgcagg cccgcttccg
gccctctgat tggtcgggaa ttgttgtcct ggaaccacg atgatgctgt ccgggaactg
tcgggactgc ggcggcgga cagggcctgg gggaggggcc tttggccgaa agttggggga
agtgcactga gcgagtggcg gccgggggac agtacctgct tgccttattg ggcaaataca
gccttccaag gtggagtcta acgccgtggt gtgaactggc cacccgaaca gggagtaaat
agtgctttgt atctttaagg aagcccttt ttaaatttaa aaaaaagtc ttaattataa
gactctttaa atgcccaact gcatacttgg agctttggga ctgaatttgg aactttcctg
tcaagcgacc tcccacgact ttactgctga gcctgtgcac gtgtgtgtaa ggggagaaat
ccaggcatct agatgcagac ttgtacccag ttacttgggg tcgcgtgcgc tcagctggga
cctgggctcg tgcgcttagt ccggagccct gatctgcgaa caggtgggtg cttcctaaag
tattcgctgg ggtccggaga atggctcgcc ttttctacag atgggagagg gctgtcacta
gaaattccgt gggttgcttg aagtcttagg accgccgatc cgtttgctga aggaatttac
tggcatttgt tggcgttctc cgctcagtgg ggcgatctct ggtcgagaat aaaatgtaaa
tctagtttgt catttttcgt taggctttgt ttccgtagcc tcttgtccgt gaaggaattt
tcaacagatc ttttggttct tgttttttctc taactttttc tatttccttt tttctttaag
gatattaaaa cttttagtac aattgattgg actacttgaa ccatcgggat ttggggagga
```

Figure 5-Sheet 2

```
actccagatt tttcattttt aaactctaaa tgtatgagga atttacagaa tggagaacga
aaaggtactt tataacttca gtattcatca ttgcaatttt aaattcagta tcatcctgat
ttaactccat aattttccc tatccaatgt gtttcttaa tgccacaacc ttggttagcc
tctgtaaaga cctggaaaaa atgaaccta tcttatagtt tcaaaaatat atagtttaaa
atatatacta atttaattaa tatagtttaa aaaatgaaaa ttatcttaaa aagaaattca
gtctccaatc atgtcaaatg cccttctga attccagttg ttcaagaatc ctcagaaatg
ttgtaatgaa actaacaaat tttattattc ttaaaaatac cttttctctc tttatgtctg
agacagctac caaatcatta aaaactagaa agagtgtaaa gggcaaacc tacccctctt
caaaaattcg ttagtttcat tacaacattt ctgaggattc ttgaacaact tggaattcag
aaagggcatt tgacatgttt ggagactgaa tttctttta agataatttt ttaccaaatt
ggcagcttat ttatggggtc tgcaaaatgc tctgtttagg gggcaaacat tttgtaaaat
tacaaaagaa ttgtctgtgg ggggtgtcca actactaata ggtttaaaaa agtgaactta
catgcatatt tcctaatagt tttagatgtt agtcaaataa gagaattact attgcttctg
ataatctgag gcaaagaaaa agcctattgt cagatcagta catctcagat gcacacactg
gcaaggagct cctgttgggt ccaccatact gacttccatg taagaagagc accatacttg
gagtgaaaat atctgtgttc cactcctacg tgacctctct cagcctgcat cttctcttct
gcgagctaag aatgcaggat tccatgaaca tacaaacgga aatgcacttg ataaacccaa
gatgtcacaa catgtccat ttgtccatgt tcttaaagtt atttggtctg cctattattt
tacttattgc tgttccaagc attttcttta aaatagataa agatgggagt agtgtgtgaa
gtccctggtg tccaaaactg gaaggaacat agtctccatt agccttattt atgaactgct
gttaatttac cctttgtct cagtggctat cctgcttctg ccaggatcta gctttgtggt
cttaggtagc tgttaggttg atgcaaacat aattgctgtt tttgccatta ctttcagtag
caaaagccac aattactttt gcaccaacct aatcatttta cttctctggg ccccattttc
tctatctgta aaatgaggga gtggatgttc aaagagcaga cttttctggt cagaaatcct
gctgttggac actctagatt tccctgataa atctgaccat atgctatccc tcactcttgt
ctccttgtct ctctgactct tcagtggtat tttatttagc acccactgca tgcagccatt
atgctaggtg gataagaatt tctgccctgt aggcctttac ttattacagt gccatgagta
aacaaaagtc atttctagaa gtttgatcat ttaacattgt cagtccaatt aggggaagct
gagtgaaggg catttgggaa ctctatactg tctttgcttc tcttctctaa atctaaaact
atttcaaaat acaattaaaa ttataagtcc taactaaagt tgtttttca gtggttgaaa
cataaggtga aaacatttat ggcttattgc aaaattaaaa atgggaaatg taattattag
aattgacaat acacatcaca tgaccattag aatacagtta ttaatttcct caactctaca
atctcattag acatttttc cttggcatga ttctattcgt tatgcaattt ctagaatcca
agctgtctga taaatcctgt tttaccatgg atttaattat ttacatttt taaaccagga
aaatctcttt tgtgagccac ataaaagggg actaatgaaa acacctctga aagaatccac
cacagcaaat atcgtgttgg cagagatcca gcctgacttt ggccctttaa ccacacctac
caagcccaag gaaggctctc agggagagcc gtggacaccg acagccaacc tgaaaatgct
catcagtgct gtgagcctg agatccgcaa cagagatcag aaaaggggtt tgtttgacaa
cagaagtgga ttacctgagg ccaaagactg tatacacgta ggtttcaga ggactggttg
gaggctgggg aattgttgg ggggagggg gaggttgtag ctattagaga agtgccagca
atttaaagca tcaccacccg aaggctgtta ttaacttcct tcggagcacc agaaaggttt
ggaccccaag aaatatagct ctgggaattc tgaacctttg cgttattttc gtttcaggct
ttcctttcag gtttgccaag catttgtac tggccccct aaccttttct cccatccaga
ctttgcagct gttgaagcta agcgtgtgta agttggtgtc agtcatcgag cacagatgcc
cctaataaat ctgtcagact ttattttaga ataagacatt gtttaccttt tcctttgtag
gaacacttat ctggagatga atttgagaaa tcccaaccaa gtcgaaaaga gaaagttta
ggattattgt gtcataagtt cttagcacga tatcctaatt atcccaaccc tgctgtgaat
aatgacatct gccttgacga agtggcagag gaacttagta agtatgcaaa gaactcactg
aaagaattaa taattaaagt ggctttatgg acttaactcc ttcagacccc cgctcatcta
gccagtgttt gtaaatgaca caaataagcc ggcatggaaa ttttctatct ctaaagccct
cttctaatat aagaatgaag gtaagtagtt gcaaatttca gcaaatcttg gaggcagaaa
agtcacaatg gaggttgctt ctgactacag ttgtctctga agctttaaag aaaggcaata
ttgtctcatg acttgtttca caaagttaca actgtgaact ttgcttcat tgctctccct
tgctgttctt gaagaatcag gctgataaat ggttatcttc ctagttgacg ctgaggatca
gcttctgtga gtgggaacag gacctgtgca ctcctggacc ttcagcacta ttctgaggac
tagttttctg aatgttttgt gttgggcaca agttattcct cctgccctt tttactctgt
tcaaagacct gaatctattt ggagctaaaa aggggcccgt ggtgaatttg gggtaccttt
```

Figure 5-Sheet 3

```
ggagtcatgt gggtatctta atttaaacct gtgaagtgat gtgctgtgca agataataca
ttttaataca aagcaatcac cccgtgaaga aaagttgccc ttctaataca tgtttgtaaa
tatcaacttt atttcacatt ttaagaatat accgtttaga ttcatctact tttcatatat
gcttaatggt agctgggtag gatattcagc aaatatctat taatcttcta ctactatgtg
tcaggcaatg ttgtaggagc ctgggataca tccgtaaaca aaaagggcaa aatctcttct
ctcttagaac ctatattcta gtggggcaat agatactgag taaaggatat aggaagtaag
taaggataat acatgctaga aggtaacatg catagtggaa aaaataaatt gtagatcagg
atcaagggat caggagtgct ggggaggtgc tttgccataa gtggtcagat caggcttcgt
tgagaaggtg acatctgggc aaggacttga aagaagcaag gtagggagct gtaaggacat
cagggagaag ggttccaggc agaaggaaca gccggtacaa agcaagtgca tatctggcag
gttccaggga cagcaagagg tcggtaggat gcaccttat taaaatagtg ttttattgat
cactttttca gaaaggctga tctcatcaaa tatttaaatt gaaattaagt ttcttgaacg
aagagaattc taacattaca gaatattgaa aacccaattt aaatagatag agtcacagaa
ttactaatat catattgtta atgatagcta gaaagtaagc aaaattagac caaaaaggc
atattttatt tttatgtaag tttttaaaaa ctacatcatg gtttttgtac ttttctgaaa
tctcagcatt ttgtttctat cttatgatca ttacagatgg gcgtgtgtgt acgtgtttgt
attggaagcg gttggaaggt gtgagatgta gagttttaaa gacttggttt gctacttgct
agctcttttg gggtgagcta cttagctggt ctgagcctct gttttctcat cgttttttttt
ttttgtttgt ttgtttgttt ttgagacgga gtctcgctct ttcgcccagg ctggagtgct
gtggcgcgat ctaggctcac tgcaagctcc gcctcccggg ttcacaccat tctcctgcct
cagcctcctg agtagctggg actacaggca cccgccacca cacccggcta atttttttgt
atttttagta gagactgggt ttcaccatgt tagccaggat ggtctccatc tcctgacctc
gtgatccgcc ctcctcggcc tcccaaggtg ctgggattac aggtgtgagc caccgcaccc
ggcctttctc atccttttta aagtgcagat cataatacct acttcacaag tttagggtga
aaacttccta aagctgtgta gcacaactta ggccctcatt aaatgttgcc tttctaattc
atatgatttg tgcccttgga aagcaagcac atgtctttct caccttcaca gtatttgttg
agtatgttca cttacagtta ggaaagtgat attatccaag acctactgac taataaacca
atggaagaaa aagctattca attctaaaca cgttacaaaa atctgtaaca cacaattgca
cattctttgt agatgttgaa cgtcgacgca tttacgatat cgtgaacgtc ctagagagtt
tacatatggt gagccgcctc gccaaaaaca ggtacacttg gcacgggcga cacaatctca
acaaaaccct tgcaccttg aagagcatcg ggaggagaa taagtacgcc gagcagatta
tgatgatcaa aaagaaagaa tatgagcaag agtttgactt tattaagagt tacagtatag
aggatcatat catcaaatca aacactggcc caaatggaca cccagacatg tgttttgtgg
aactccctgg agtggaatt cgggcaggtg agagatggta gtgaaaactc caggcggcat
ggcatttgtc ctctgtctaa ggaaaaggtt ctgtggagaa cacagctcta aagctactgc
tgccttaat gttcagatgc cacagttgtc agctgtatga tcaggtggta gtattttag
ccttgttact ttagaagtca cttgtccctt tatgaatttt aattctctaa tcctcatcct
tctctaaagc ttctgtaaac agccgcaaag acaagtcttt aagggtaatg agccagaaat
ttgtgatgct gttttggtg tcaacgcctc agatagtaag cctagaagtt gctgccaaga
ttttaattgg ggaggaccat gtggaagatt tggataaaag caagtttaaa agtaagtgtc
atgactgcca tggattttg aacctattct taaacaataa aatctcagtc gtaaactcat
ttccaaatta ggaaacatag gtgcataaac agatcttctc taattatgtt tttatatctt
ctccccagaa gccatgataa tattgattta gctaacttgt tatgatacat aagtatcact
actctttttt ttttttttt ttttagacg gagtctagct cttttgctag gctggagtgc
agtggcgaga tctaggctca ctgcaacatc tgcctcccgg gttccagcaa ttctcctgcc
tcagtctccg gagtagctgg gattacagtt gcgcgccacc acacccggct aattttttata
ttttagtgg agacggggtt tcaccatgtt ggccaggagg atctcgatct cttgacctcg
tgatccaccc acctcggcct cccaaatttt ggaggcctc ccaaaattac aggcctgagc
cactgcgcct ggccaagtat cactactctt atttgacaca ttgcttcatt tgatattgta
acattgttct caaaagtaaa cacggccagg cgcggtggct gaagcctgta atctcagcac
tttgggaggc cgaggagggc ggatcatgag gtcaggagat ccagaccaac ctggctaaca
cagtgaaacc ccgtctctac taaaaataca aaaaattag ccgggcgtgg tggcgtgcac
ctgtagtccc agttactcag gaggctgagg caggagaatg gcgtgaacct gggaggcggc
gcttgcagtg agccgagatc gcgccactgc actccagcct ggggacaga gcaagactct
gtctcaaaaa aaaggaaaca ctagaagaat ctgttctgtg tgagctctaa atgagagtaa
attgtaaagt gggtctgcac cctggtctcc ttccactgat gctgattaca gagggtttat
aaatgactca taaaattgtc cccagaagtg acctgcagca caggtagtct gccatttga
```

Figure 5-Sheet 4

```
aagaatggtt ttagctagat tacctgctca aaattgggaa gggactgtag attggattcc
taacaaaaga gctatgccct caccattaca ccagactttg caggaagggt gtggaaagaa
gtgctcagcg gatgggagg agcacttggc tcgggagatc gggagatctg caatttcaga
aaacacgtcc tgatactact gaggggttac ttgcctttg tgagtcaccg gatagttttc
atctttgttt cactggttag tcatagcctt gaaaactatt ccaggaactg cagaggtgta
agttactgaa tccccaggga attcagaacc ttctgatatg gctaggaagg agactcgatt
tgtaattgt actatcaaga tggcagtaaa aaacagactt tttgtaacaa aactctttaa
gatatgtgag gtttgtcaag ttcacagatc tatgttttgc atgttacata gacagtatta
aaaaattaca catgttgatg gagtacagaa ttttccatgc tgccatagta aataaatttt
gttataagct attacaagca gaaaagcaag acatttatca cagatacttt tacttctctg
ctcataaaat tcttctgaat cctcattaga agatacccag gaatggtgac tttattttg
aaacagtctg taacatagtt tcagataggg tgatctcatc aagtcgtttt tcctttgtca
acgtatgcta ttgtcatttc aacattgagt actagcagta attgagtctt taaatattt
aaaacttttt tatcttaatt aaagttgtat caccagaaga acttaaaagg aggcagatgt
ttctctgtct gacattgatg gttaagacag ctcttagaat atacatgaag tccttctgaa
ggaaaattct ttgatctttt cattattcca ttaagtggta tatatacttt ttttcccagc
aaaaattagg aggttgtatg atatagctaa tgttctgagt agcctggatc ttatcaagaa
agttcatgtt acagaggaaa gaggccgaaa accagctttc aaatggaccg gcccagaaat
cagtccaaat accagtggta tgtatttttt tcttcaccc tctgctttat tatttgtgtg
tgtgttttc taattttaa tttccagtgt gtgttgttcc cctccctgtg tccatgtgtt
ctcattgttc aactcccact tacgagtgag aacatgcagt gtttgatttt ctattcctat
gttagtttgc tgaggatgat ggcttccagc tccatccgtg tcccacagag gacatgatct
catttctttt tatggctgca tagtattcca tggtgtatat gtaccacatt ttctttatcc
tgctttatta ttttgaatta atgcacattg ggagatattt tcccttcccc ttcctactca
ccgccccaca tggaaaagat atatatgatt gaaaagatga ttcaagatga atggcaatat
agaaagtttg gctactggct ccatcagcta accaagatcc ataacaacct cccaccctgt
gttcaagaag tacaatctgt atgtgaaagc attcggaaag ttgaaagcac cacaaagcat
aaaacactat tgctgctatg cggcacagtg accacaacag aacctgtgcc cattgagaat
atgaaatgag ttcactctgg tatcaaagta gatatttcta gccttcatct taactctgcg
atgctgacat tttgcattct accaaagatc cccacccaga atcattgaaa atgacaagaa
cgtgggccat gaagacagag ggaaacttag gttccattcc aagccctgcc actctggctt
tgcggcctga gacaagctac ttcttcgagg attagttttc tccttggtga atgggaaga
acaatggcac ctcagtggag ttactgtgat tttggtataa tctcagagag aggtcctttc
gtgcaggaat ttggagtgaa aattccgggg ccatattgac caggttcata tcccaggccc
acatgctccc agttgagaga ccttgagcca gtaggttaat gtctgtgtgg gtcagagctc
tcatctccga cacagggctg catttcttga ggaacagtta cctcatgag ctgtgaggat
cacccatatt tcatcagatc taagacttca ctgattgtaa gatgcacaat tctttctata
tcactaagaa agaaaaatca ctaataacta cactctagca caccactggt tataagatat
agtgcagttt cagaaatgct aatgtaggaa atattgtgtc tcagaatcca tttaataaga
taaacaaggc tttctctgta aagcccttag aacagtgaca ggcacatggt cggtgctctg
taacttgcca cttttattcc taaaattgtt ttatttcata tcccaaaagc caactgagcc
atccaggttt taatacacag acgtttctg tttcaggctc cagcccagtc attcatttta
ctccctctga tttggaggtg agacggtctt caaagagaa ctgtgccaaa aacctctttt
ccacacgtgg gaaaccaaac tttactcgac acccatctct tatcaaattg gtaaagagta
tagaaagtga tcggagaaag ataattctg cgcccagtag ccctatcaag accaacaaag
gtatgttttc aggaatgtca gggatctgct aggaagaatt ccctttatc tcatttttc
agcttacttg atccttgcaa tagttgtcag agaattattt caatatctat atacccaaac
cctcttgaag cctaactaat gtataaattt aaaaagtcat ttgtggggtt tattgtttaa
tgctatgca actttgaggg gaggtgcaca ctttctgttc tctgacttc agtgaggttt
catctgtgtg aacatttgtt ctttagcttt gaccggtgct ctcttccttt ctattttacc
agctgagagt tctcagaatt ctgcaccctt cccaagtaaa atggctcagc tgcagctat
ttgtaaaatg cagttagaag agcaatcaag gtaggttggc aatcctcttt aataacagga
tgaattactt ttacattaca ttgttaggat tacttatttt atgtgagaag aagccctagc
cttgaactgg agagctaatc ttttctgtat ctcatactca ctcattacag aaattatctg
catgttccat aaaagcgtgg cttcaatatg aggcttaaag cggtagaaca gttcagaaaa
aatgtatatc catcatgtcg tgtattaaat cttgtctttc agtgaatcca gacagaaagt
gaaagtacag ctggcaagat ctggaccctg caaaccagta gcccctctgg accccccagt
```

Figure 5-Sheet 5

```
gaatgctgag atggagctga cagcaccgtc cctcatccag ccc ctgggaa tggttcccct
gatccccagc cccttgtcat cagcagtgcc cctgatccta cct caggccc cttcaggccc
atcctatgcc atctacctgc agcccactca agcccaccaa agtgtgacgc caccccaagg
cctgagccca acggtgtgca ccacccactc ttctaaagct actggctcaa aagactccac
agatgccacc actgagaagg cagccaatga tacctcaaag gccagtgcct ctaccaggcc
tggaagcttg ctgccagcac cagagaggca aggggcaaag agccgaacca gggagccagc
tggagaaaga ggctcaaaga gggcaagcat gctcgaggac agtggttcca aaaagaaatt
taaagaggac ctaaaaggac ttgaaaatgt ctccgcagta agtacagcct tgaactgcac
aaagctttag gaattcccta gtctattaca ggaagattgg tggcttgtga aatttaccga
agagcattct ctcagaagac aaggaactgt tccttagcat cccataatcc aagtgaggcc
ctcaacagct aatccctgg ctgggatgaa ggcagggaca tttttaacct tggaggaag
ggattatttg ctgtctttt aaagtaccat gggtggttgt cct taagtcc atttctccat
cacacactgg aatgcaaaca gctgtcatga aagtcttaaa taattacaa gcagacgtaa
ccccaaatga acgtgtggat gcatagggtt cctgtaactc ctgctttctg agtcattacc
taatgtttgt ttgttgtcat gtaactggca tctgttgcct agaagataaa ttgctccccg
ttttttacttt ctacctaaaa tttaaatcaa aatttctatt tcatgtaaat agaaaaatca
aactgatctt ggcaaattgt agatatagtt catgtattgg tttctagaga ttttgacatg
ctagacaaat ttttttccta agtggagatt agttccggag ggaattaata tttattggat
gcctacccac atatagcaga cataatagat attagtcact tttacataca gtatctcatt
ttcctcccct aggacaatta tatatgagag acattactgt atcatccgat aaataccact
aaatgtgcaa gtaaaagtta atctctcatt ttgcccctgc tcttaataca agctatttta
cttctctctg tcttattttt ccgcatcggt aaagaattta ttccaccagt ttttcctcat
cacctactgg atataaagca ctgtgctctg gatcaaatct aacccagcac ctgcctttgg
tgcaattgc ttttgggtac ttgcctgtgg gcatatgata gttttttgtgg ggttaagtga
atttattcca tgatgataca cataaaaggg tttgatcctt ttaagacgtg ttataagctg
aaaggtatta tctgttacgt tgttattaaa gaggaagctt agagtttgtc aaatcttccc
tgaggatggc ctcatggtaa ccattcaaaa catctattat cttacatagt atcctttgt
atttaatgta tatgccaagt gggaaatcat aaggtttcaa tattctggaa ggtccataac
ttcttttggc caatgggtat gatttaataa tggtctcctg ttgcttacat agttattcag
gattaggatt ttcagtggat agatttttcca tatactcctg cttcttttt atatctctgc
aactctaacc atttcttttt tcttttgaga cagggtctta ctctgtcacc cagaatggag
tgcagtggca tgattttagc tcactgcagc ctcgacctcc aaggcttaag tgatcctccc
acctcagtct cccaagtaac ttagactaca ggtgtgctgc catgcccggc taattttttta
tttttttgtgg agacgggggtt tcaccatgtt gctcagcctg gtctcgaact cctgagctca
agcagtctgc ctgccttggc ttcccaaagt gctgagatca caggcatttg ccgtcatgcc
cagcccactt taaccatttc gttttagtat ggcctgagca aaacaaagac aatgagagag
tcatgtgtta attcattcaa caaatttta ctgagaattt atacttctag gggtggaaag
aagataagta tgcaagtaaa cacaaacata tcaggtagtg aatgatagga atgaagatga
catgatagga ggaaggggtg gaagggctac tgtaggctag aagagttcaa gttcaaatat
gtcagattca ttcggcaatt taatagttct aattatttta taaaaaggg aattggcata
ggttaaaaga ttctataatg aatatagttt gttggaaatt taaaaattat tattctatta
ttgtgggttt tactgaagac ttgaaagagt taaaccagca gtcagaataa tttgtaccat
gagagaatat aactaaagct aatagagcgc aggtcttcat aaagcaccta aatttgcccc
ttaaaaattc tctcttcctg cagttttcaa ggcacctact agtagagatt tgagtggga
ccaagtactt aagaaacaaa attaaaagct tgtagtatac ttttagcttt gtggattctg
aatttcctgg ttcccaagga aaagacctat taacaactag attaaacttg ttttgacaat
ggagagaaga aaggtctgaa ggaagaaaaa aggaggtccc tagtttataa gagcggtttt
tagcttttgc cagtcccgct catggtaagg ctaaagcaga cttttcatgc agttcaggca
cccgtgtaaa cttttctgt ttgggaaagt acagtgatct aataggcatg ttgggaggta
catgcaaccc taccttggg cctttttctag ttgcaatata act ttattgc ctaaagcttt
tgctcaatgg catgtgcgtc tctaatatga attaatcagt tctcttattt gtaattttt
taactctggt gtactttgcg tattttaaga ctgcttgtta tcattagagc aagcagtact
agaaagaaat ctttacttat ataatttctg ttttaaatca ggggccagca aacgttcttt
aaagggccag atagtagaca ttttttgggt ttaaggcca tatgggctct gttgcaccta
gtcaactctg ccattgtagc aggaaagttg ctataggcag tacataaatg aatgagtatg
attgtgttcc aatgaaactt tatttataaa aacaggcagg gagtgggaat tggcacatgg
ccaatagttt agcccccttt ctctaaatca atgtcattta aagtgtttcc ttagaatact
```

Figure 5-Sheet 6

```
agtcctcctt aattgcctac tgaaaatata gttgccaaat agtttgggaa atgctacctg
ctgtgtgccc cacttggaga attttaaggc atgccaccat taaaatctct tggaaattct
ctaataaaga caccatttga cttttgtttaa ttcagtattt tccaattata tttgaccaag
aatcaggtaa tgcctgtttg caacccatgg acctcaggtc cctcagaatg ccctttggga
aataccgttc tacataattc aagaacaatc aattactact acatcatacc aaggagtcca
gtagcaagag ttaagttatc agtttaagag tggtgtgctg gatgaatcct tacccctaag
cagggtcagt gccatcatcc aaaggtgtcc taagaccaca ggtggcattt aagaaacatg
ttctgcatta ttcgggcaa gcattgggaa gggtgggagg gtattctcct ctaggagcca
ggtgaccagc ctgcctgcag cccactccgc tggaggcttt ggtccaatga ggcaaccacc
aagggatatt agtcctgaaa gaggcacgtg gccattttc ttcctgtatt tgtgtgtaaa
ataaaccctt cctccttgtt ttctagacct tgttcccatc aggataccta atccctctca
cgcagtgctc atccctgggg gcagagtcca ttttgtctgg taaagaaaac tcaagtgctc
tttccccaaa ccacaggatt tacagctccc caattgcagg tgagtgcaca taaaacacta
accagatgtg ggccggtctc aagttcactt aagccttgtc aacttcttgg ataaatgcct
gtgcttttaa gatatcttcc ccctttcct tccaggtgtt attccagtga catcatctga
actcactgct gttaattttc cctctttca tgtaacaccg ttgaagctaa tggtctcacc
aacttccgtg gcagccgtac ctgtcgggaa cagcccggct ctcgcttcaa gccaccctgt
tcccatccag aacccaagct cagccattgt aaacttcacc ctgcagcacc tgggactcat
ctcacccaat gtgcagttgt ctgccagccc tgggtctgga atcgttcctg tgtctccaag
aatagagtct gttaatgtcg caccagaaaa tgcaggcact cagcaaggaa gggccaccaa
ctatgactca ccagtcccag gccagagcca gccaaatgga caatcagttg ctgtgacagg
ggcacaacag gtgagaggct ttctacttaa tttaattttt cctggaatta ctaagcccca
agtatctgtg tcataagaga ttggcttttg cttttcctct tggagaggg aaaggatggg
aaagtcagga gattgaaggc ctatgtttct tccagaaccc aggaagagtg tccaaggcat
ccatattgtt gggttatcat gagattttg tctctcccct aacaaaaata attgagaatg
taaaactcac caaagcttcc ctcgccaatt tcaagatacg ccagtttccc atgtgcaat
acattcatcc agcccaatct tccaagtctg gtaagactat gtacctgtgt gtggttgact
tcttttgtcc attcttctct ttccaatcag cctgttcctg tgacacccaa agggtcacaa
ttagtggccg aaagtttctt ccgtacccca ggtggaccca ccaagccaac cagctcatcc
tgcatggatt ttgagggtgc taataaaacc tccttaggaa ctctctttgt cccacagcga
aaactggaag tctcaacaga ggatgtccat taatcaacag atgttggctt agtttaattt
tctaaagagt tgtttaatag agaaatgta cacagactga tttggagaac acattctctg
aaaatactgt aaatacgttg gggattgtt caatgtgaaa tcagatagtt gttttcatac
atatatatat atacacacac acacacacac acacacacac atatatttgt ataaagctaa
gtttagcttt caatcctaca aaataaaagt aaaatgttga actctaagat atattaactt
ctagggggaa aaatccatta ttttagctat gcctatacta ttatgcaaag taactgtatt
aaagtttact tccctctaag caaatatgct tgacatgcct aacacagcat tcccttaaac
attttgcaca aagaaaatgc tgtgtgatgt ataatgttgt attttaaat aggggtatag
ctatatttt tgtaatttct ttaatctgtt gttgcagtgt atcttttgt aaagtttgca
acaatcctca atcaagtcta tggaaaatt atttataaaa tgtatttta atcataagtt
gttcaaatta aaactttct aaaatatagt tagcattttc atttcgccgg ttagggcact
gttgggagaa aattaaaatt tacctaatca cagaggcaaa ttcttagtaa agagtatcca
tgctgggttc cattagatat gcaaagttta tagaatgttt ctacattctg tccccattt
tgacccttga gattgctcca cttttgcaga agtaaaattg gctttggaga ggttgttgct
tggccaagaa cacctagcta agtcccatgt gcttcctacc acactccacg agattagaaa
tgaaaggtag gcgcctaggg gccctggtgt gaccagcatc tgtcccacgc ttcctgctct
actcagaggt gggtctgtac cagctctctt aacatacttc ttggatggcc cagctccagg
gacaggaaaa cggcagtaag gattctaatg tcctccacac ctggagaacc cccaggagct
ccaagagaag ggacaagttc cagtgtgtta agtgtgcatc tctttgaccc gtttgttatg
ggaagaactg caccttgaga attgacaagt gctttccctg gttagggtct taaggagca
tcatagtatc tatttcctac atgtttacta tatgtagaca gggttatacg ttttaaatgt
atcatatctg tgagctacaa ctgaggctca cagggattaa agcaacaagt ccatggtcac
actgctagtg tatgcaagtc tcagctcatg tctattggac ctcattatcc attgcccatt
tacttctaga gacatgccta gcagctctag taggaatcaa gcacattgat tcagggtaat
```

F13 aligned with F13H

```
F13    1   MEVNCLTLKDLISPRQPRLDFAVEDGENAQKENIFVD-RSRMAPKTPIKNEPIDLSKQKK
           ME N                                +KEN+F + R  KTP+K       +
F13H   1   ME-N-------------------EKENLFCEPHKRGLMKTPLKESTTANIVLAE

F13   60   FTPERNPIT-PVKLVDRQQAEPWTPTANLKMLISAASPDIRDREKKKGLFRPIENKDDAF
           P+    P+T P K  + Q EPWTPTANLKMLISA SP+IR+R++K+GLF         +A
F13H  35   IQPDFGPLTTPTKPKEGSQGEPWTPTANLKMLISAVSPEIRNRDQKRGLFDNRSGLPEA-

F13  119   TDSLQLDVVGDSAVDEFEKQRPSRKQKSLGLLCQKFLARYPSYPLSTEKTTISLDEVAVS
           D +   + GD    EFEK +PSRK+KSLGLLC KFLARYP+YP       I LDEVA
F13H  94   KDCIHEHLSGD----EFEKSQPSRKEKSLGLLCHKFLARYPNYPNPAVNNDICLDEVAEE

E2FA
                  **************
F13  179   LGVERRRIYDIVNVLESLHLVSRVAKNQYGWHGRHSLPKTLRNLQRLGEEQKYEEQMAYL
           L VERRRIYDIVNVLESLH+VSR+AKN+Y WHGRH+L KTL   L+ +GEE KY EQ+  +
F13H 150   LNVERRRIYDIVNVLESLHMVSRLAKNRYTWHGRHNLNKTLGTLKSIGEENKYAEQIMMI

F13  239   QQKELD-----LIDYKFGE---RKKDGDPDSQEQQLLDFSEPDCPSSSANSRKDKSLRIM
           ++KE +     + Y +   +   G   ++     +   ++S NSRKDKSLR+M
F13H 210   KKKEYEQEFDFIKSYSIEDHIIKSNTGPNGHPDMCFVELPGVEFRAASVNSRKDKSLRVM

E2FB
                                             **********
F13  291   SQKFVMLFLVSKTKIVTLDVAAKILI-EESQDAPDHSKFKTKVRRLYDIANVLTSLALIK
           SQKFVMLFLVS +IV+L+VAAKILI E+  + D SKFKTK+RRLYDIANVL+SL LIK
F13H 270   SQKFVMLFLVSTPQIVSLEVAAKILIGEDHVEDLDKSKFKTKIRRLYDIANVLSSLDLIK

F13  350   KVHVTEERGRKPAFKWIGP-----------VDFSSSDEELVDVSASVLPELKRETYGQI
           KVHVTEERGRKPAFKW GP              + F+ SD E+     S      +  T G
F13H 330   KVHVTEERGRKPAFKWTGPEISPNTSGSSPVIHFTPSDLEVRRSSKENCAKNLFSTRG--

F13  398   QVCAKQKLARHGS-FNTVQASERIQRKVNSEPSSPYR-----EEQGSGGYSLEIGSLAAV
               K   RH S  +NT V++ E +RK+NS PSSP +       Q S   +   ++  LAA+
F13H 388   ----KPNFTRHPSLIKLVKSIESDRRKINSAPSSPIKTNKAESSQNSAPFPSKMAQLAAI

F13  452   YRQKIEDNSQGKAFASKRVVPPSSSLDPVAPF-PVLSVDPEYCVNPLAHPVFSVAQTDLQ
           + ++E+ S       +   +   S     PVAP  P ++ + E       L P+
F13H 444   CKMQLEEQSSESRQKVRVQLARSGPCKPVAPLDPPVNAEMELTAPSLIQPL---------

F13  511   AFSMQNGLNGQVDVSLASAASAVESLKPALLAG-------QPL----VYVPSASLFMLYG
                      G V +  + +SAV + P +G       QP       P L
F13H 495   ---------GMVPLIPSPLSSAVPLILPQAPSGPSYAIYLQPTQAHQSVTPPQGLSPTVC
```

Figure 6

```
F13    560  SLQEGPASGSGSERD--------DRSSEAPATVELSSAPSAQKRLCEERKPQEEDEPATK
              +    A+GS    D         D S   + +T   S  P+ +++   + R  + E +K
F13H   546  TTHSSKATGSKDSTDATTEKAANDTSKASASTRPGSLLPAPERQGAKSRTREPAGERGSK

F13    612  RQSREYEDGPLSLVMPKKPSDSTDLASPKTMGNRASIPLKDIHVNGQLPAAEEISGKATA
            R S       + G S     K+    + S    +      IPL       G         A
F13H   606  RASMLEDSG--SKKKPKEDLKGLENVSATLFPSGYLIPLTQCSSLG-------------A

F13    672  NSLVSSEWGNPSRNTDVEKPSKENESTKEPSLLQYLCVQSPAGLNGFNVLLSGSQTPPTV
             S++S                KEN S    P+    Y   SP  + G  + S    T
F13H   651  ESILS--------------GKENSSALSPNHRIY---SSP--IAGVIPVTSSELT----

F13    732  GPSSGQLPSFSV-PCMVLPSP------PLGPFPVLYSPAMPGPVSSTLGALPNTGPVNFS
                + PSF V P ++ SP       P+G  P L S + P P+ +     P++  VNF+
F13H   687  ---AVNFPSFHVTPLKLMVSPTSVAAVPVGNSPALAS-SHPVPIQN-----PSSAIVNFT

F13    785  LPGLGSIA---QLLVGPTAVVNPKSSTLPSAD--PQ----LQSQPSLNLSPVMSRSHSVV
            L  LG I+   QL   P + + P S  + S  + P+       Q + +   SPV  +S
F13H   738  LQHLGLISPNVQLSASPGSGIVPVSPRIESVNVAPENAGTQQGRATNYDSPVPGQS----

F13    836  QQPESPVYVGHPVSVVKLQQSPVPVTPKSIQRTHRETFFKTPGSLGDPVLKRRERNQSRN
            QP      G V+V   QQ PVPVTPK  Q   E+FF+TPG    P           + N
F13H   793  -QPN-----GQSVAVTGAQQ-PVPVTPKGSQLV-AESFFRTPGGPTKPTSSSCMDFEGAN

F13    896  TSS------AQRRLEIPSGGAD 911
            +S       QR+LE+ +
F13H   846  KTSLGTLFVPQRKLEVSTEDVH 861
```

Figure 6 (Cont.)

Figure 7
F13 - 911 amino acids - Chromosome 12q21.1
F13H - 867 amino acids - Chromosome 11p15.1

SEQUENCE LISTING

```
<160> NUMBER OF SEQ ID NOS: 12

<210> SEQ ID NO 1
<211> LENGTH: 12
<212> TYPE: DNA
<213> ORGANISM: homo sapiens

<400> SEQUENCE: 1
ggcgcgagtt tc                                                         12
```

<210> SEQ ID NO 2
<211> LENGTH: 78
<212> TYPE: DNA
<213> ORGANISM: homo sapiens

<400> SEQUENCE: 2
ctcctcgcgg cgcgagtttc aggcagcgct gcgtcctgct gcgcacgtgg gaagccctgg    60
ccccggccac ccccgcga                                                  78

<210> SEQ ID NO 3
<211> LENGTH: 11
<212> TYPE: DNA
<213> ORGANISM: homo sapiens

<400> SEQUENCE: 3
ggcgcgagtt t                                                         11

<210> SEQ ID NO 4
<211> LENGTH: 71
<212> TYPE: DNA
<213> ORGANISM: homo sapiens

<400> SEQUENCE: 4
aattcggcgc gagtttaggg cgcgagttta gggcgcgagt ttagggcgcg agtttagggc    60
gcgagtttag t                                                         71

<210> SEQ ID NO 5
<211> LENGTH: 76
<212> TYPE: DNA
<213> ORGANISM: homo sapiens

<400> SEQUENCE: 5
aattcggcgc gagtttcctg cgcgagtttc ctggcgcga gtttcctggc gcgagtttcc    60
tggcgcgagt ttcctt                                                    76

<210> SEQ ID NO 6
<211> LENGTH: 531
<212> TYPE: DNA
<213> ORGANISM: homo sapiens

<400> SEQUENCE: 6
atttgttgat cgatcaagga tggccccgaa gactccaata aaaatgaac caattgattt    60 atcgaagcaa aaaaattta ctccagaaag aaatcccatt actccagtta agcttgttga   120
cagacagcaa gcggaaccat ggacacccac agctaacctg aagatgctca ttagtgctgc   180
cagcccagat ataagggacc gggagaagaa aaagggacta ttccgaccca ttgaaaacaa   240
ggacgatgca tttacagatt ctctacagct tgatgttgtt ggggacagtg ctgtggacga   300
atttgaaaag caaggccaa gcagaaaaca gaaaagttta ggactcctgt gccagaagtt   360
tctagctcgc tatccaagtt atcccttgtc aactgagaaa actaccatct ccctagatga   420
agttgctgtc agtcttggtg tggaaaggag acgcatctat gacattgtaa atgtgctgga   480
gtcgctgcat ctggtcagcc gggtggctaa gaatcagtat ggctggcatg g            531

<210> SEQ ID NO 7
<211> LENGTH: 583
<212> TYPE: DNA
<213> ORGANISM: homo sapiens

<400> SEQUENCE: 7

-continued

```
gaattcataa ttcctgaggg gtgttaagaa gcagtcccat tggtgaggat attatgactt      60
ggtgaccatt cttaggagta gaaaaccaag gacaattgct tctgtattca gtatccactt     120
cttaatgtgg ctttatatgt aaaaataata atgcagtggt tgtttctgtc aggaaaataa     180
atcttacaga caactggtg gaattgaagc tgctgcgcta gacttggata tttttgggtag     240 tgaagaagca atggcaatct tgagtctatt attgtataat ttagtaaaag aaaaaaataa     300
tcgttggtgg tcctactaag agaatgcagc ttttttgagt tgtcacagag gctgtgtgtg     360
ccctacactg accagggttt gtaaaaccct ttcattctgg tacaagagtc gggggtataa     420
cttttatact tgaatctacc taccaagttt acatttctca attcctttt gtaaggtgct      480 atttctgtat ttaaataact ttcttttaac cgtaaagctg ctttctgctt atcttattgc     540
actgctagtt gtatgtaggt attaatttta ttgctgctta ctg                      583

<210> SEQ ID NO 8
<211> LENGTH: 5724
<212> TYPE: DNA
<213> ORGANISM: homo sapiens

<400> SEQUENCE: 8
ctacgatcca ggctggagtt gcgctcggcc ggtctgagcg ctggcgctgc ccggacgccg      60
cggggtcccc gccagcccag ggcactcggc gcggggatct gcgcgcctcg ctctcccttc     120
ccgatgccgc cgcccggctg ctgatcgccg caccaccttc cctcatcggc ttgggtccgt     180
ggaggtccct gcagaggcag gaagcctcct taggaaagca gggatggagg taaattgttt     240
aacactaaaa gacctgatca gccccaggca gcccagacta gattttgcag ttgaagatgg     300
ggaaaatgca caaaggaaa atatatttgt tgatcgatca aggatggccc cgaagactcc      360
aataaaaaat gaaccaattg atttatcgaa gcaaaaaaa tttactccag aaagaaatcc      420
cattactcca gttaagcttg ttgacagaca gcaagcggaa ccatggacac ccacagctaa     480
cctgaagatg ctcattagtg ctgccagccc agatataagg gaccgggaga agaaaaaggg     540
actattccga cccattgaaa acaaggacga tgcatttaca gattctctac agcttgatgt     600
tgttggggac agtgctgtgg acgaatttga aaagcaaagg ccaagcagaa aacagaaaag     660
tttaggactc ctgtgccaga agtttctagc tcgctatcca agttatccct tgtcaactga     720
gaaaactacc atctccctag atgaagttgc tgtcagtctt ggtgtggaaa ggagacgcat     780
ctatgacatt gtaaatgtgc tggagtcgct gcatctggtc agccgggtgg ctaagaatca     840
gtatggctgg catggacggc acagcctgcc aaaaaccctg aggaacctcc agagactagg     900
agaggagcag aaatatgaag agcaaatggc ctacctccaa cagaaagagc tggacctgat     960
agattataaa tttggagaac gtaaaaaga tggtgatcca gattcccagg aacaacagtt    1020
actggatttc tctgaacccg actgtccctc ttcatctgca aacagtagaa aagacaagtc    1080
tctgagaatt atgagccaga gtttgtcat gctgttcctc gtctccaaaa ccaagattgt    1140
cactctggat gtggctgcca aaatactgat agaagaaagc caagatgccc agaccatag    1200 taaatttaaa acaaaggtac gacgcctcta tgacatagcc aatgttctga ccagcttggc    1260
tctgataaag aaagtgcatg taacagaaga gcgaggtcgt aaaccagcct tcaagtggat    1320
cgggcctgtg gacttcagct caagtgatga agaactggtg gatgtttctg catctgtctt    1380
accagaattg aaaagagaaa catatggcca gattcaagtc tgtgcaaaac agaagctggc    1440
tcgccatggt tcttttaaca cagttcaggc ttctgagagg atccagagga agtgaactc     1500 agaaccgagc agcccgtaca gagaagaaca aggatcaggt ggctactctt tagaaattgg    1560
```

-continued

```
aagcctggca gctgtctata gacagaaaat agaagacaat tcacagggaa aagcctttgc    1620
cagtaagaga gtggtgcctc catcaagcag cttggaccct gttgctcctt tccctgtcct    1680
ctctgttgac ccagaatatt gtgttaatcc tttagcccac ccagtatttt ctgttgctca    1740
gacggacctg caggcattct ccatgcagaa cggtctgaat ggacaagtgg atgtctcact    1800
tgcttctgca gcctctgctg tggagagcct gaagccagca ctccttgctg ccagcctct    1860 agtgtatgtg ccctctgcct cactgttcat gctgtatgga agtctgcagg agggaccagc    1920
gtcagggtca gggtcagaga gggatgacag aagctcagaa gccccagcca cagtagagct    1980
gtcatctgca ccctcagctc agaagcgcct ctgtgaggag aggaaacctc aggaggagga    2040
tgagccagcc actaaaaggc aaagtaggga atatgaagac ggcccgctgt cgcttgtcat    2100
gcccaagaaa ccctcagatt ccacagacct tgcctctccc aagactatgg gtaacagggc    2160
atctataccc ctcaaagaca ttcatgtgaa tggccaactc cctgctgcag aagagatttc    2220
aggaaaggca acagcaaact ctcttgtttc ttctgagtgg ggaaatcctt caagaaatac    2280
agatgttgaa aagccttcaa aagaaaatga agcaccaaa gagccttctt tgctacaata    2340
tctttgtgtg cagtctcctg caggattaaa tggtttcaat gtactttat ctggcagtca    2400 aaccccccct actgtgggcc cgtcctcagg tcagctgccg tctttcagtg tcccttgcat    2460
ggtcttacca tctccacctc tgggcccttt tcctgttctc tattctcctg caatgccggg    2520
cccggtttct tccactcttg gtgctctccc aaacacagga cctgtgaatt tcagcttgcc    2580
tggccttgga tcaatagccc agcttctcgt cggcccaca gctgtggtta atccaaagtc    2640
gtccacactc ccttctgcag accctcagct tcagagtcag ccctcactaa acctaagtcc    2700
agtgatgtca aggtcacaca gtgtcgtcca acaacctgag tcccccgttt acgtgggaca    2760
tccagtctca gtagtaaaat tacaacagtc accagttcca gtgacccca agagcatcca    2820 acgcacacat cgtgagacgt ttttcaagac acccggcagc cttggagacc ctgtcctgaa    2880
gagaagagaa aggaaccagt cacgaaacac cagctcggcc cagaggagac tagaaatccc    2940
cagcggcggc gctgactaac ctgccgcttt gccaggtggg ggtgggatca aacgccctga    3000
gagtcccgga tgtccgaggc gggatgcaaa ccatcccgtc ctgagcacgg gtccttcctc    3060
tctctttcat ccacacttct gttaacttcc caccaccatc aatcatctga tttcctgaaa    3120
gtaattaatt gtgcatttaa taccagttag agttccgact ctgcatggtg tcacagtgaa    3180
agcgccgact gacttatggt tttgattcaa gaatcgtctt attgctggaa gtagatctga    3240
ataggctacc ggagccttgt ttttctaaag gggggcgctg tctagcactt aactagggta    3300
agcattctta acatgtattt ccacttgccc tgagtaaatc tgtggtgaga gaagcttcct    3360
ttctgcagtt taaaaaagct actgcttcct taggcttcat caggaagcca ccttcagttg    3420
tgaatcctat ggtgttattt attttgttcc tgaaatggga tttagtgcaa aaagtttaca    3480
actacagtct ttaacacatt ttttcaggg tatgacgact tgaatgttta acttttatt    3540 ctataatttg ccctgcactt attttacaac ctagtaataa tgtggataaa tgtatctaca    3600
tgacacatgt caagaccaaa ataactgtga atgacacacc ttgctgtaaa tgaactgtgc    3660
taaccctgac tgtgggcttg agaacaaaga tgaactctag aactctagca gcctaactgc    3720
tgcttctcaa ataactgtgt gaacagtgag atattactgt ttgtttctaa aaatcctact    3780
gtgcccagtt tccttcacta catgcccctgc attttttatt taaatattta gctgtagcgc    3840
catcagatat ggatgccttc taacaattgc tgtttgtaaa ataaatcagg atggtagaaa    3900
```

```
gtgattatat ggaaaattgg aacctggatg agaccttttc gttgaattct gaagagtaat  3960
gatgtgaaaa ttgatacagg gcaagagatg attcttttgt ttttcttcta cttcatgtcc  4020
agaagagtaa gagggaaaat ggacatatgt ttcatatcca agggtattca aactgtagtt  4080
agttggtacc tctgaaaaat gagaatggtg agcgcacggg ttggttgttc tagcatgaat  4140
acaattctgg aaactgttat gcaatttccc tttttttaacc cacattactt taggggtgca  4200
ttaagtcgcc aaactatact agttctttgt attcctagac ttgctgatat ttacctctct  4260
cttgtctctt cagagtaaat ggttcccttc tttccttcct actttccttc attctctctt  4320
ccttccctcc ttcctacttc ttttcttcct tcctcttcct ctcttaaaac tatcttagat  4380
gtagaatcct ggtgtagggt tttattttat ttttattttt tgacccaata aaatgttata  4440
tgaaagaatg aaaatattaa tttaagagac tctgggagtc tgaataaagt agctttatat  4500
taactacagg ataatattag ccttattacc cccacaagat ttttttaaaac ttgaggtagg  4560 tagctacatt aaataaattt gctacttata taaaattttt tatcaacact aaacttttaa  4620
agtttacaag ttttttttttt cttttttaca gtcttctata gagttaggtt aaaaatgtgg  4680
ttctaaccat caacaattgc atggttaaat gaccctgaac taaaactgat gggttcccta  4740
tcaaaacaaa taaaaatata ccttttttcag gtttcaatct gtgcagggta tatgcatgtt  4800
aattctacca tgcttaagaa cttccacaaa atatttcatg gagaggtctg catttagacg  4860
gaaacagaaa ttgcttttcc cctcactgtt cctgaatgct ctatacttgt tttaacattt  4920
ttgctatctt ttttttattat tctgatcatg atatgaccat ttaacctcag aattcataat  4980
tcctgagggg tgttaagaag cagtcccatt ggtgaggata ttatgacttg gtgaccattc  5040
ttaggagtag aaaaccaagg acaattgctt ctgtattcag tatccacttc ttaatgtggc  5100
tttatatgta aaaataataa tgcagtggtt gtttctgtca ggaaaataaa tcttacagaa  5160
caactggtgg aattgaagct gctgcgctag acttggatat tttgggtagt gaagaagcaa  5220
tggcaatctt gagtctatta ttgtataatt tagtaaaaga aaaaaataat cgttggtggt  5280
cctactaaga gaatgcagct tttttgagtt gtcacagagg ctgtgtgtgc cctacactga  5340
ccagggtttg taaacccctt tcattctggt acaagagtcg ggggtataac ttttatactt  5400
gaatctacct accaagttta catttctcaa ttcctttttg taaggtgcta tttctgtatt  5460
taaataactt tcttttaacg taaagctgct ttctgcttat cttattgcac tgctagttgt  5520
atgtaggtat taattttatt gctgcttact gcttttgttt tcttattatt tagctctgct  5580 cttttttccta atggctatat tatctatagc tatttacttg taactgtact acatgtaaac  5640 tgatttttg ttctgatttt ttttctaata ttttttaggaa aatattaagc tttataaaat  5700
agcaataaaa aataattcat ttaa                                         5724
```

<210> SEQ ID NO 9  
<211> LENGTH: 911  
<212> TYPE: PRT  
<213> ORGANISM: homo sapiens

<400> SEQUENCE: 9

Met Glu Val Asn Cys Leu Thr Leu Lys Asp Leu Ile Ser Pro Arg Gln  
1               5                   10                  15

Pro Arg Leu Asp Phe Ala Val Glu Asp Gly Glu Asn Ala Gln Lys Glu  
            20                  25                  30

Asn Ile Phe Val Asp Arg Ser Arg Met Ala Pro Lys Thr Pro Ile Lys  
        35                  40                  45

```
Asn Glu Pro Ile Asp Leu Ser Lys Gln Lys Phe Thr Pro Glu Arg
 50                  55                  60

Asn Pro Ile Thr Pro Val Lys Leu Val Asp Arg Gln Gln Ala Glu Pro
 65                  70                  75                  80

Trp Thr Pro Thr Ala Asn Leu Lys Met Leu Ile Ser Ala Ala Ser Pro
                 85                  90                  95

Asp Ile Arg Asp Arg Glu Lys Lys Lys Gly Leu Phe Arg Pro Ile Glu
            100                 105                 110

Asn Lys Asp Asp Ala Phe Thr Asp Ser Leu Gln Leu Asp Val Val Gly
        115                 120                 125

Asp Ser Ala Val Asp Glu Phe Glu Lys Gln Arg Pro Ser Arg Lys Gln
    130                 135                 140

Lys Ser Leu Gly Leu Leu Cys Gln Lys Phe Leu Ala Arg Tyr Pro Ser
145                 150                 155                 160

Tyr Pro Leu Ser Thr Glu Lys Thr Thr Ile Ser Leu Asp Glu Val Ala
                165                 170                 175

Val Ser Leu Gly Val Glu Arg Arg Ile Tyr Asp Ile Val Asn Val
            180                 185                 190

Leu Glu Ser Leu His Leu Val Ser Arg Val Ala Lys Asn Gln Tyr Gly
    195                 200                 205

Trp His Gly Arg His Ser Leu Pro Lys Thr Leu Arg Asn Leu Gln Arg
210                 215                 220

Leu Gly Glu Glu Gln Lys Tyr Glu Glu Gln Met Ala Tyr Leu Gln Gln
225                 230                 235                 240

Lys Glu Leu Asp Leu Ile Asp Tyr Lys Phe Gly Glu Arg Lys Lys Asp
                245                 250                 255

Gly Asp Pro Asp Ser Gln Glu Gln Gln Leu Leu Asp Phe Ser Glu Pro
            260                 265                 270

Asp Cys Pro Ser Ser Ser Ala Asn Ser Arg Lys Asp Lys Ser Leu Arg
        275                 280                 285

Ile Met Ser Gln Lys Phe Val Met Leu Phe Leu Val Ser Lys Thr Lys
    290                 295                 300

Ile Val Thr Leu Asp Val Ala Ala Lys Ile Leu Ile Glu Glu Ser Gln
305                 310                 315                 320

Asp Ala Pro Asp His Ser Lys Phe Lys Thr Lys Val Arg Arg Leu Tyr
                325                 330                 335

Asp Ile Ala Asn Val Leu Thr Ser Leu Ala Leu Ile Lys Lys Val His
            340                 345                 350

Val Thr Glu Glu Arg Gly Arg Lys Pro Ala Phe Lys Trp Ile Gly Pro
        355                 360                 365

Val Asp Phe Ser Ser Asp Glu Glu Leu Val Asp Val Ser Ala Ser
    370                 375                 380

Val Leu Pro Glu Leu Lys Arg Glu Thr Tyr Gly Gln Ile Gln Val Cys
385                 390                 395                 400

Ala Lys Gln Lys Leu Ala Arg His Gly Ser Phe Asn Thr Val Gln Ala
                405                 410                 415

Ser Glu Arg Ile Gln Arg Lys Val Asn Ser Glu Pro Ser Ser Pro Tyr
            420                 425                 430

Arg Glu Glu Gln Gly Ser Gly Gly Tyr Ser Leu Glu Ile Gly Ser Leu
        435                 440                 445

Ala Ala Val Tyr Arg Gln Lys Ile Glu Asp Asn Ser Gln Gly Lys Ala
    450                 455                 460

Phe Ala Ser Lys Arg Val Val Pro Pro Ser Ser Ser Leu Asp Pro Val
```

-continued

```
            465                 470                 475                 480
        Ala Pro Phe Pro Val Leu Ser Val Asp Pro Glu Tyr Cys Val Asn Pro
                        485                 490                 495
        Leu Ala His Pro Val Phe Ser Val Ala Gln Thr Asp Leu Gln Ala Phe
                        500                 505                 510
        Ser Met Gln Asn Gly Leu Asn Gly Gln Val Asp Val Ser Leu Ala Ser
                        515                 520                 525
        Ala Ala Ser Ala Val Glu Ser Leu Lys Pro Ala Leu Leu Ala Gly Gln
                        530                 535                 540
        Pro Leu Val Tyr Val Pro Ser Ala Ser Leu Phe Met Leu Tyr Gly Ser
        545                 550                 555                 560
        Leu Gln Glu Gly Pro Ala Ser Gly Ser Gly Ser Glu Arg Asp Asp Arg
                        565                 570                 575
        Ser Ser Glu Ala Pro Ala Thr Val Glu Leu Ser Ser Ala Pro Ser Ala
                        580                 585                 590
        Gln Lys Arg Leu Cys Glu Glu Arg Lys Pro Gln Glu Glu Asp Glu Pro
                        595                 600                 605
        Ala Thr Lys Arg Gln Ser Arg Glu Tyr Glu Asp Gly Pro Leu Ser Leu
                        610                 615                 620
        Val Met Pro Lys Lys Pro Ser Asp Ser Thr Asp Leu Ala Ser Pro Lys
        625                 630                 635                 640
        Thr Met Gly Asn Arg Ala Ser Ile Pro Leu Lys Asp Ile His Val Asn
                        645                 650                 655
        Gly Gln Leu Pro Ala Ala Glu Glu Ile Ser Gly Lys Ala Thr Ala Asn
                        660                 665                 670
        Ser Leu Val Ser Ser Glu Trp Gly Asn Pro Ser Arg Asn Thr Asp Val
                        675                 680                 685
        Glu Lys Pro Ser Lys Glu Asn Glu Ser Thr Lys Glu Pro Ser Leu Leu
                        690                 695                 700
        Gln Tyr Leu Cys Val Gln Ser Pro Ala Gly Leu Asn Gly Phe Asn Val
        705                 710                 715                 720
        Leu Leu Ser Gly Ser Gln Thr Pro Pro Thr Val Gly Pro Ser Ser Gly
                        725                 730                 735
        Gln Leu Pro Ser Phe Ser Val Pro Cys Met Val Leu Pro Ser Pro Pro
                        740                 745                 750
        Leu Gly Pro Phe Pro Val Leu Tyr Ser Pro Ala Met Pro Gly Pro Val
                        755                 760                 765
        Ser Ser Thr Leu Gly Ala Leu Pro Asn Thr Gly Pro Val Asn Phe Ser
        770                 775                 780
        Leu Pro Gly Leu Gly Ser Ile Ala Gln Leu Leu Val Gly Pro Thr Ala
                        785                 790                 795                 800
        Val Val Asn Pro Lys Ser Ser Thr Leu Pro Ser Ala Asp Pro Gln Leu
                        805                 810                 815
        Gln Ser Gln Pro Ser Leu Asn Leu Ser Pro Val Met Ser Arg Ser His
                        820                 825                 830
        Ser Val Val Gln Gln Pro Glu Ser Pro Val Tyr Val Gly His Pro Val
                        835                 840                 845
        Ser Val Val Lys Leu Gln Gln Ser Pro Val Pro Val Thr Pro Lys Ser
                        850                 855                 860
        Ile Gln Arg Thr His Arg Glu Thr Phe Phe Lys Thr Pro Gly Ser Leu
        865                 870                 875                 880
        Gly Asp Pro Val Leu Lys Arg Arg Glu Arg Asn Gln Ser Arg Asn Thr
                        885                 890                 895
```

Ser Ser Ala Gln Arg Arg Leu Glu Ile Pro Ser Gly Gly Ala Asp
              900                 905                 910

<210> SEQ ID NO 10
<211> LENGTH: 3657
<212> TYPE: DNA
<213> ORGANISM: homo sapiens

<400> SEQUENCE: 10

| | | | | | |
|---|---|---|---|---|---|
| attgggcaaa | tacagccttc | caaggtggag | tctaacgccg | tggtgtgaac | tggccacccg | 60 |
| aacagggagt | aaatagtgct | ttgtatcttt | aaggaagccc | ttttttaaat | ttaaaaaaaa | 120 |
| agtcttaatt | ataagactct | ttaaatgccc | aactgcatac | ttggagcttt | gggactgaat | 180 |
| ttggaacttt | cctgtcaagc | gacctcccac | gactttactg | ctgagcctgt | gcacgtgtgt | 240 |
| gtaaggggag | aaatccaggc | atctagatgc | agacttgtac | ccagttactt | ggggtcgcgt | 300 |
| gcgctcagct | gggacctggg | ctcgtgcgct | tagtccggag | ccctgatctg | cgaacaggat | 360 |
| attaaaactt | ttagtacaat | tgattggact | acttgaacca | tcgggatttg | gggaggaact | 420 |
| ccagattttt | cattttaaa | ctctaaatgt | atgaggaatt | tacagaatgg | agaacgaaaa | 480 |
| ggaaaatctc | ttttgtgagc | cacataaaag | gggactaatg | aaaacacctc | tgaaagaatc | 540 |
| caccacagca | aatatcgtgt | tggcagagat | ccagcctgac | tttggccctt | taaccacacc | 600 |
| taccaagccc | aaggaaggct | ctcagggaga | gccgtggaca | ccgacagcca | acctgaaaat | 660 |
| gctcatcagt | gctgtgagcc | ctgagatccg | caacagagat | cagaaaaggg | gtttgtttga | 720 |
| caacagaagt | ggattacctg | aggccaaaga | ctgtatacac | gaacacttat | ctggagatga | 780 |
| atttgagaaa | tcccaaccaa | gtcgaaaaga | gaaaagttta | ggattattgt | gtcataagtt | 840 |
| cttagcacga | tatcctaatt | atcccaaccc | tgctgtgaat | aatgacatct | gccttgacga | 900 |
| agtggcagag | gaacttaatg | ttgaacgtcg | acgcatttac | gatatcgtga | acgtcctaga | 960 |
| gagtttacat | atggtgagcc | gcctcgccaa | aaacaggtac | acttggcacg | ggcgacacaa | 1020 |
| tctcaacaaa | acccttggca | ccttgaagag | catcggggag | gagaataagt | acgccgagca | 1080 |
| gattatgatg | atcaaaaaga | aagaatatga | gcaagagttt | gactttatta | agagttacag | 1140 |
| tatagaggat | catatcatca | aatcaaacac | tggcccaaat | ggacacccag | acatgtgttt | 1200 |
| tgtggaactc | cctggagtgg | aatttcgggc | agcttctgta | aacagccgca | aagacaagtc | 1260 |
| tttaagggta | tgagccaga | aatttgtgat | gctgttttg | gtgtcaacgc | ctcagatagt | 1320 |
| aagcctagaa | gttgctgcca | agattttaat | tggggaggac | catgtggaag | atttggataa | 1380 |
| aagcaagttt | aaaacaaaaa | ttaggaggtt | gtatgatata | gctaatgttc | tgagtagcct | 1440 |
| ggatcttatc | aagaaagttc | atgttacaga | ggaaagaggc | cgaaaccag | ctttcaaatg | 1500 |
| gaccggccca | gaaatcagtc | caaataccag | tggctccagc | ccagtcattc | attttactcc | 1560 |
| ctctgatttg | gaggtgagac | ggtcttcaaa | agagaactgt | gccaaaaacc | tcttttccac | 1620 |
| acgtgggaaa | ccaaacttta | ctcgacaccc | atctcttatc | aaattggtaa | agagtataga | 1680 |
| aagtgatcgg | agaaagataa | attctgcgcc | cagtagccct | atcaagacca | acaaagctga | 1740 |
| gagttctcag | aattctgcac | ccttcccaag | taaaatggct | cagctcgcag | ctatttgtaa | 1800 |
| aatgcagtta | gaagagcaat | caagtgaatc | cagacagaaa | gtgaaagtac | agctggcaag | 1860 |
| atctggaccc | tgcaaaccag | tagcccctct | ggaccccca | gtgaatgctg | agatggagct | 1920 |
| gacagcaccg | tccctcatcc | agcccctggg | aatggttccc | ctgatcccca | gcccttgtc | 1980 |
| atcagcagtg | cccctgatcc | tacctcaggc | cccttcaggc | ccatcctatg | ccatctacct | 2040 |

```
gcagcccact caagcccacc aaagtgtgac gccaccccaa ggcctgagcc caacggtgtg    2100
caccacccac tcttctaaag ctactggctc aaaagactcc acagatgcca ccactgagaa    2160
ggcagccaat gatacctcaa aggccagtgc ctctaccagg cctggaagct tgctgccagc    2220
accagagagg caaggggcaa agagccgaac cagggagcca gctggagaaa gaggctcaaa    2280
gagggcaagc atgctcgagg acagtggttc caaaagaaa tttaaagagg acctaaaagg    2340
acttgaaaat gtctccgcaa ccttgttccc atcaggatac ctaatccctc tcacgcagtg    2400
ctcatccctg ggggcagagt ccattttgtc tggtaaagaa aactcaagtg ctcttttcccc    2460 aaaccacagg atttacagct ccccaattgc aggtgttatt ccagtgacat catctgaact    2520
cactgctgtt aattttccct cttttcatgt aacaccgttg aagctaatgg tctcaccaac    2580
ttccgtggca gccgtacctg tcgggaacag cccggctctc gcttcaagcc accctgttcc    2640
catccagaac caagctcag ccattgtaaa cttcaccctg cagcacctgg gactcatctc    2700
acccaatgtg cagttgtctg ccagccctgg gtctggaatc gttcctgtgt ctccaagaat    2760
agagtctgtt aatgtcgcac cagaaaaatg aggcactcag caaggaaggg ccaccaacta    2820
tgactcacca gtcccaggcc agagccagcc aaatggacaa tcagttgctg tgacaggggc    2880
acaacagcct gttcctgtga cacccaaagg gtcacaatta gtggccgaaa gtttcttccg    2940
taccccaggt ggacccacca agccaaccag ctcatcctgc atggattttg agggtgctaa    3000
taaaacctcc ttaggaactc tctttgtccc acagcgaaaa ctggaagtct caacagagga    3060
tgtccattaa tcaacagatg ttgrcttagt ttaaytttct aaagagttgt ttaatagaga    3120
aaatgtacac agactgattt ggagaacaca ttctctgaaa atactgtaaa tacgttgggg    3180
atttgttcaa tgtgaaatca gatagttgtt ttcatacata tatataya cacacacaca    3240 cacacacaca cacacayata tatttgtata aagctaagtt tagctttcaa tcctacaaaa    3300
taaaagtaaa atgttgaact ctaagatata ttaacttcta gggggaaaaa tccattattt    3360
tagctatgcc tatactatta tgcaaagtaa ctgtattaaa gtttacttcc ctctaagcaa    3420
atatgcttga catgcctaac acagcattcc cttaaacatt ttgcacaaag aaaatgctgt    3480
gtgatgtata atgttgtatt tttaaatagg ggtatagcta tatttttgt aatttctta    3540 atctgttgtt gcagtgtatc ttttttgtaaa gtttgcaaca atcctcaatc aagtctatgg    3600
aaaaattatt tataaaatgt attttaatc ataagttgtt caaattaaaa cttttct    3657
```

<210> SEQ ID NO 11
<211> LENGTH: 867
<212> TYPE: PRT
<213> ORGANISM: homo sapiens

<400> SEQUENCE: 11

```
Met Glu Asn Glu Lys Glu Asn Leu Phe Cys Glu Pro His Lys Arg Gly
1               5                   10                  15

Leu Met Lys Thr Pro Leu Lys Glu Ser Thr Thr Ala Asn Ile Val Leu
            20                  25                  30

Ala Glu Ile Gln Pro Asp Phe Gly Pro Leu Thr Thr Pro Thr Lys Pro
        35                  40                  45

Lys Glu Gly Ser Gln Gly Glu Pro Trp Thr Pro Thr Ala Asn Leu Lys
    50                  55                  60

Met Leu Ile Ser Ala Val Ser Pro Glu Ile Arg Asn Arg Asp Gln Lys
65                  70                  75                  80

Arg Gly Leu Phe Asp Asn Arg Ser Gly Leu Pro Glu Ala Lys Asp Cys
```

-continued

```
                85                  90                  95
Ile His Glu His Leu Ser Gly Asp Glu Phe Glu Lys Ser Gln Pro Ser
            100                 105                 110

Arg Lys Glu Lys Ser Leu Gly Leu Leu Cys His Lys Phe Leu Ala Arg
            115                 120                 125

Tyr Pro Asn Tyr Pro Asn Pro Ala Val Asn Asn Asp Ile Cys Leu Asp
            130                 135                 140

Glu Val Ala Glu Glu Leu Asn Val Glu Arg Arg Ile Tyr Asp Ile
145                 150                 155                 160

Val Asn Val Leu Glu Ser Leu His Met Val Ser Arg Leu Ala Lys Asn
            165                 170                 175

Arg Tyr Thr Trp His Gly Arg His Asn Leu Asn Lys Thr Leu Gly Thr
            180                 185                 190

Leu Lys Ser Ile Gly Glu Glu Asn Lys Tyr Ala Glu Gln Ile Met Met
            195                 200                 205

Ile Lys Lys Lys Glu Tyr Glu Gln Glu Phe Asp Phe Ile Lys Ser Tyr
            210                 215                 220

Ser Ile Glu Asp His Ile Ile Lys Ser Asn Thr Gly Pro Asn Gly His
225                 230                 235                 240

Pro Asp Met Cys Phe Val Glu Leu Pro Gly Val Glu Phe Arg Ala Ala
            245                 250                 255

Ser Val Asn Ser Arg Lys Asp Lys Ser Leu Arg Val Met Ser Gln Lys
            260                 265                 270

Phe Val Met Leu Phe Leu Val Ser Thr Pro Gln Ile Val Ser Leu Glu
            275                 280                 285

Val Ala Ala Lys Ile Leu Ile Gly Glu Asp His Val Glu Asp Leu Asp
            290                 295                 300

Lys Ser Lys Phe Lys Thr Lys Ile Arg Arg Leu Tyr Asp Ile Ala Asn
305                 310                 315                 320

Val Leu Ser Ser Leu Asp Leu Ile Lys Lys Val His Val Thr Glu Glu
            325                 330                 335

Arg Gly Arg Lys Pro Ala Phe Lys Trp Thr Gly Pro Glu Ile Ser Pro
            340                 345                 350

Asn Thr Ser Gly Ser Ser Pro Val Ile His Phe Thr Pro Ser Asp Leu
            355                 360                 365

Glu Val Arg Arg Ser Ser Lys Glu Asn Cys Ala Lys Asn Leu Phe Ser
370                 375                 380

Thr Arg Gly Lys Pro Asn Phe Thr Arg His Pro Ser Leu Ile Lys Leu
385                 390                 395                 400

Val Lys Ser Ile Glu Ser Asp Arg Arg Lys Ile Asn Ser Ala Pro Ser
            405                 410                 415

Ser Pro Ile Lys Thr Asn Lys Ala Glu Ser Ser Gln Asn Ser Ala Pro
            420                 425                 430

Phe Pro Ser Lys Met Ala Gln Leu Ala Ala Ile Cys Lys Met Gln Leu
            435                 440                 445

Glu Glu Gln Ser Ser Glu Ser Arg Gln Lys Val Arg Val Gln Leu Ala
            450                 455                 460

Arg Ser Gly Pro Cys Lys Pro Val Ala Pro Leu Asp Pro Val Asn
465                 470                 475                 480

Ala Glu Met Glu Leu Thr Ala Pro Ser Leu Ile Gln Pro Leu Gly Met
            485                 490                 495

Val Pro Leu Ile Pro Ser Pro Leu Ser Ser Ala Val Pro Leu Ile Leu
            500                 505                 510
```

Pro Gln Ala Pro Ser Gly Pro Ser Tyr Ala Ile Tyr Leu Gln Pro Thr
    515                 520                 525

Gln Ala His Gln Ser Val Thr Pro Pro Gln Gly Leu Ser Pro Thr Val
    530                 535                 540

Cys Thr Thr His Ser Ser Lys Ala Thr Gly Ser Lys Asp Ser Thr Asp
545                 550                 555                 560

Ala Thr Thr Glu Lys Ala Ala Asn Asp Thr Ser Lys Ala Ser Ala Ser
                565                 570                 575

Thr Arg Pro Gly Ser Leu Leu Pro Ala Pro Glu Arg Gln Gly Ala Lys
            580                 585                 590

Ser Arg Thr Arg Glu Pro Ala Gly Glu Arg Gly Ser Lys Arg Ala Ser
    595                 600                 605

Met Leu Glu Asp Ser Gly Ser Lys Lys Lys Phe Lys Glu Asp Leu Lys
    610                 615                 620

Gly Leu Glu Asn Val Ser Ala Thr Leu Phe Pro Ser Gly Tyr Leu Ile
625                 630                 635                 640

Pro Leu Thr Gln Cys Ser Ser Leu Gly Ala Glu Ser Ile Leu Ser Gly
                645                 650                 655

Lys Glu Asn Ser Ser Ala Leu Ser Pro Asn His Arg Ile Tyr Ser Ser
            660                 665                 670

Pro Ile Ala Gly Val Ile Pro Val Thr Ser Ser Glu Leu Thr Ala Val
    675                 680                 685

Asn Phe Pro Ser Phe His Val Thr Pro Leu Lys Leu Met Val Ser Pro
    690                 695                 700

Thr Ser Val Ala Ala Val Pro Val Gly Asn Ser Pro Ala Leu Ala Ser
705                 710                 715                 720

Ser His Pro Val Pro Ile Gln Asn Pro Ser Ala Ile Val Asn Phe
                725                 730                 735

Thr Leu Gln His Leu Gly Leu Ile Ser Pro Asn Val Gln Leu Ser Ala
            740                 745                 750

Ser Pro Gly Ser Gly Ile Val Pro Val Ser Pro Arg Ile Glu Ser Val
    755                 760                 765

Asn Val Ala Pro Glu Asn Ala Gly Thr Gln Gln Gly Arg Ala Thr Asn
    770                 775                 780

Tyr Asp Ser Pro Val Pro Gly Gln Ser Gln Pro Asn Gly Gln Ser Val
785                 790                 795                 800

Ala Val Thr Gly Ala Gln Gln Pro Val Pro Thr Pro Lys Gly Ser
                805                 810                 815

Gln Leu Val Ala Glu Ser Phe Phe Arg Thr Pro Gly Gly Pro Thr Lys
            820                 825                 830

Pro Thr Ser Ser Ser Cys Met Asp Phe Glu Gly Ala Asn Lys Thr Ser
    835                 840                 845

Leu Gly Thr Leu Phe Val Pro Gln Arg Lys Leu Glu Val Ser Thr Glu
    850                 855                 860

Asp Val His
865

<210> SEQ ID NO 12
<211> LENGTH: 20099
<212> TYPE: DNA
<213> ORGANISM: homo sapiens

<400> SEQUENCE: 12
ggtaactgtc actcagacat ctgcagcatg aatggccctg tagatcacag atttgaacga      60

-continued

```
attagtcact atctctgaac acaggtgcat gaggcagact gcttctaaag aactttaaaa    120
gggatttatg gcccacagga ctccggggct gtaataactt cgggtacatt aggcatagct    180
gaatctatgc actcttggga gcgctgacca ttcaggggt tggggagat gacaatctgg     240
ccaacagcta gtggctaaag cagaagcacc aactcccac tttttgttga tacatttaga    300
acccagtctt gctccaaaaa aggggtacct gggcttagta agaaccagcc gctcagtgct    360
agcaacggtg gaaccctata tagtgacctc tgctttattt caaatctgcg agccacaggc    420
agtggcccct ctgcacagta cctgaaaggc ctgctttcag gtcgaagcgc cttcttgagc    480
aagacctgca cctcagctgg cgacgaaagg gggacaggga cacgacggcg ccaacattcc    540
agggcggcca caccgcaagc ctgcggtcgc gttccgcggg gagatgagcc ttcgctcgcc    600
acggagaccc ctggccctat ggccggcagc tgctgcgctg cgaccccagc ctcaatatca    660
tagcatcccc gccctcatcg cgtttcgcag aaaataaaaa tgcctcgccc tgctagtcag    720
caatgggaga gtcactgatc cccaagttag cggtgggagt ggggaagtgt ggccccgggc    780
cctgctggag cctaaagaca cgcgattaca gaggaggacg agccaaaccg agtccagatc    840
gagagaccgg cgcccagatc tcggcgcggt tgggcaacac tcagcaccag tccgcagaaa    900
agtctaaggc agaggagagc aaagggagcc aacgcgggcg caaatgatcc aggtgcagcc    960
gaggcagcgc cgccgccccg ggcctcggtg tcccgttctg caaagtgagg acgaaggatc   1020
gaagtgtctc cccgaccctg ctagggctct acagggaacc aggctaaagc tgcctgaggc   1080
tcggagaccg gaaaaagagg gaaagacaac agggaagaga aagggaggag tgggtgggag   1140
accctgagga aagacggcga ggacagggtt ggagggtttt ccgccttcct cctcttcctc   1200
ctacacctga gttctcaccg ctgggccaag gcccagagcc cacggagctt aggcaccagt   1260
agccaagctt ctccctcctc gcgccagttt ctgcgaggca cggggcagac ggtgggcagc   1320
acaatcatgc atgccagggg tgcaagggg agaggtccgg ctggagtccg agggcaggtg    1380
agccggcctg gggctgggca ggggtgagat agccccaagc ggggaatcgc agggcgcctg   1440
cggcccagcc cgccgagcccc ggacgggcca aattttattc cccaactttg agcaagggga   1500
gggggtgtat gcaaaaaaaa aaaaaaagga aaaaaagtt gctgaacttt tcccccaact   1560
ctgccgtaga ggcgggagtg gagggcggtg cctgcaccga ttcgccggcg gctacggtcg   1620
ggaggctcgg attggcgctc gggggccggg gccggggcga gcgggcgtgg gggaggggag   1680
cggccctccc cgcccgcggt atcggctcgc gccgggagcg ggttaatttc aaatcggggg   1740
cttggctgct cctggacggt cacgctccct ctgcccgcca gccggcccgc cagtcccggt   1800
cccggcgtct ctctccggca cccacctcgg cgctgcggaa agactgactg ccaggtacgc   1860
gggctcccgg gcctgagagg ggcagcggtg ctgacgagtc ccggctcagc cccgccggc   1920
tcccgccgtg aggtggactg acaggtcagc gggacgcaga ggggcgcggc gcccgggcga   1980
cacggcaccg ggagagggct cgggagggtg gcggcggcgg cggcggcggc cgtttcccgc   2040
ctcccgcttc gccgggggcc gtgagggagg agctgagctc ccgcgcagag gggcggggc    2100
gaacgagggg gaggggcggg gttgccgtgg ttccgggcgc gggtttgccc gcgctcaggc   2160
cccgcgcagc taaggggagg cgccggccac ggtccgactt tccgcgccaa attttttaaat   2220
cgaaggcgga aggtccggcc ccgcccctgg cgccgtcggc caatcgcagg cccgcttccg   2280
gccctctgat tggtcgggaa ttgttgtcct ggaaaccacg atgatgctgt ccgggaactg   2340
tcgggactgc ggcgggcgga cagggcctgg gggaggggcc tttggccgaa agttggggga   2400
```

```
agtgcactga gcgagtggcg gccgggggac agtacctgct tgccttattg ggcaaataca    2460
gccttccaag gtggagtcta acgccgtggt gtgaactggc cacccgaaca gggagtaaat    2520
agtgctttgt atctttaagg aagcccctttt ttaaatttaa aaaaaaagtc ttaattataa    2580
gactctttaa atgcccaact gcatacttgg agctttggga ctgaatttgg aactttcctg    2640
tcaagcgacc tcccacgact ttactgctga gcctgtgcac gtgtgtgtaa ggggagaaat    2700
ccaggcatct agatgcagac ttgtacccag ttacttgggg tcgcgtgcgc tcagctggga    2760
cctgggctcg tgcgcttagt ccggagccct gatctgcgaa caggtgggtg cttcctaaag    2820
tattcgctgg ggtccggaga atggctcgcc ttttctacag atgggagagg ctgtcacta    2880 gaaattccgt gggttgcttg aagtcttagg accgccgatc cgtttgctga aggaatttac    2940
tggcatttgt tggcgttctc cgctcagtgg ggcgatctct ggtcgagaat aaaatgtaaa    3000
tctagtttgt catttttcgt taggctttgt ttccgtagcc tcttgtccgt gaaggaattt    3060
tcaacagatc ttttggttct tgttttctc taacttttc tatttccttt tttcttaag    3120 gatattaaaa cttttagtac aattgattgg actacttgaa ccatcgggat ttggggagga    3180
actccagatt tttcattttt aaactctaaa tgtatgagga atttacagaa tggagaacga    3240
aaaggtactt tataacttca gtattcatca ttgcaatttt aaattcagta tcatcctgat    3300
ttaactccat aatttttccc tatccaatgt gttttcttaa tgccacaacc ttggttagcc    3360
tctgtaaaga cctggaaaaa atgaacctta tcttatagtt tcaaaaatat atagtttaaa    3420
atatatacta atttaattaa tatagtttaa aaaatgaaaa ttatcttaaa aagaaattca    3480
gtctccaatc atgtcaaatg ccctttctga attccagttg ttcaagaatc ctcagaaatg    3540
ttgtaatgaa actaacaaat tttattattc ttaaaaatac cttttctctc tttatgtctg    3600
agacagctac caaatcatta aaaactagaa agagtgtaaa ggggcaaacc taccccctctt    3660 caaaaattcg ttagtttcat tacaacattt ctgaggattc ttgaacaact tggaattcag    3720
aaagggcatt tgacatgttt ggagactgaa tttcttttta agataatttt ttaccaaatt    3780
ggcagcttat ttatggggtc tgcaaaatgc tctgttttagg gggcaaacat tttgtaaaat    3840
tacaaaagaa ttgtctgtgg ggggtgtcca actactaata ggtttaaaaa agtgaactta    3900
catgcatatt tcctaatagt tttagatgtt agtcaaataa gagaattact attgcttctg    3960
ataatctgag gcaaagaaaa agcctattgt cagatcagta catctcagat gcacacactg    4020
gcaaggagct cctgttgggt ccaccatact gacttccatg taagaagagc accatacttg    4080
gagtgaaaat atctgtgttc cactcctacg tgacctctct cagcctgcat cttctcttct    4140
gcgagctaag aatgcaggat tccatgaaca tacaaacgga aatgcacttg ataaacccaa    4200
gatgtcacaa catgtcccat ttgtccatgt tcttaaagtt atttggtctg cctattattt    4260
tacttattgc tgttccaagc attttctttta aaatagataa agatgggagt agtgtgtgaa    4320
gtccctggtg tccaaaactg gaaggaacat agtctccatt agccttattt atgaactgct    4380
gttaatttac ccttttgtct cagtggctat cctgcttctg ccaggatcta gctttgtggt    4440
cttaggtagc tgttaggttg atgcaaacat aattgctgtt tttgccatta ctttcagtag    4500
caaaagccac aattactttt gcaccaacct aatcatttta cttctctggg ccccatttc    4560 tctatctgta aaatgaggga gtggatgttc aaagagcaga cttttctggt cagaaatcct    4620
gctgttggac actctagatt tccctgataa atctgaccat atgctatccc tcactcttgt    4680
ctccttgtct ctctgactct tcagtggtat tttatttagc acccactgca tgcagccatt    4740
atgctaggtg gataagaatt tctgccctgt aggcctttac ttattacagt gccatgagta    4800
```

-continued

```
aacaaaagtc atttctagaa gtttgatcat ttaacattgt cagtccaatt aggggaagct    4860
gagtgaaggg catttgggaa ctctatactg tctttgcttc tcttctctaa atctaaaact    4920
atttcaaaat acaattaaaa ttataagtcc taactaaagt tgttttttca gtggttgaaa    4980
cataaggtga aaacatttat ggcttattgc aaaattaaaa atgggaaatg taattattag    5040
aattgacaat acacatcaca tgaccattag aatacagtta ttaatttcct caactctaca    5100
atctcattag acattttttc cttggcatga ttctattcgt tatgcaatTT ctagaatcca    5160
agctgtctga taaatcctgt tttaccatgg atttaattat ttacatttTT taaaccagga    5220
aaatctcttt tgtgagccac ataaaagggg actaatgaaa acacctctga aagaatccac    5280
cacagcaaat atcgtgttgg cagagatcca gcctgacttt ggccctttaa ccacacctac    5340
caagcccaag gaaggctctc agggagagcc gtggacaccg acagccaacc tgaaaatgct    5400
catcagtgct gtgagccctg agatccgcaa cagagatcag aaaagggggt tgtttgacaa    5460
cagaagtgga ttacctgagg ccaaagactg tatacacgta ggttttcaga ggactggttg    5520
gaggctgggg aatttgttgg ggggagggg  gaggttgtag ctattagaga agtgccagca    5580
atttaaagca tcaccacccg aaggctgtta ttaacttcct tcggagcacc agaaaggttt    5640
ggaccccaag aaatatagct ctgggaattc tgaacctttg cgttattttc gtttcaggct    5700
ttcctttcag gtttgccaag cattttgtac tggccccccct aacctttct  cccatccaga   5760 ctttgcagct gttgaagcta agcgtgtgta agttggtgtc agtcatcgag cacagatgcc    5820
cctaataaat ctgtcagact ttattttaga ataagacatt gtttaccttt tcctttgtag    5880
gaacacttat ctggagatga atttgagaaa tcccaaccaa gtcgaaaaga gaaaagttta    5940
ggattattgt gtcataagtt cttagcacga tatcctaatt atcccaaccc tgctgtgaat    6000
aatgacatct gccttgacga agtggcagag gaacttagta agtatgcaaa gaactcactg    6060
aaagaattaa taattaaagt ggcttatatgg acttaactcc ttcagacccc cgctcatcta    6120
gccagtgttt gtaaatgaca caaataagcc ggcatggaaa ttttctatct ctaaagccct    6180
cttctaatat aagaatgaag gtaagtagtt gcaaatttca gcaaatcttg gaggcagaaa    6240
agtcacaatg gaggttgctt ctgactacag ttgtctctga agctttaaag aaaggcaata    6300
ttgtctcatg acttgtttca caagttaca  actgtgaact tttgcttcat tgctctccct    6360
tgctgttctt gaagaatcag gctgataaat ggttatcttc ctagttgacg ctgaggatca    6420
gcttctgtga gtgggaacag gacctgtgca ctccctggacc ttcagcacta ttctgaggac    6480
tagttttctg aatgttttgt gttgggcaca agttattcct cctgcccctt tttactctgt    6540
tcaaagacct gaatctattt ggagctaaaa aggggcccgt ggtgaatttg ggtaccttt     6600 ggagtcatgt gggtatctta atttaaacct gtgaagtgat gtgctgtgca agataataca    6660
ttttaataca aagcaatcac cccgtgaaga aaagttgccc ttctaataca tgtttgtaaa    6720
tatcaacttt atttcacatt ttaagaatat accgtttaga ttcatctact tttcatatat    6780
gcttaatggt agctgggtag gatattcagc aaatatctat taatcttcta ctactatgtg    6840
tcaggcaatg ttgtaggagc ctgggataca tccgtaaaca aaaagggcaa aatctcttct    6900
ctcttagaac ctatattcta gtggggcaat agatactgag taaaggatat aggaagtaag    6960
taaggataat acatgctaga aggtaacatg catagtggaa aaaataaatt gtagatcagg    7020
atcaagggat caggagtgct ggggaggtgc tttgccataa gtggtcagat caggcttcgt    7080
tgagaaggtg acatctgggc aaggacttga aagaagcaag gtagggagct gtaaggacat    7140
```

```
cagggagaag ggttccaggc agaaggaaca gccggtacaa agcaagtgca tatctggcag    7200
gttccaggga cagcaagagg tcggtaggat gcacccttat taaaatagtg ttttattgat    7260
cacttttcca gaaaggctga tctcatcaaa tatttaaatt gaattaagt ttcttgaacg     7320 aagagaattc taacattaca gaatattgaa aacccaattt aaatagatag agtcacagaa    7380
ttactaatat catattgtta atgatagcta gaaagtaagc aaaattagac ccaaaaaggc    7440
atattttatt tttatgtaag ttttttaaaaa ctacatcatg gttttttgtac ttttctgaaa   7500 tctcagcatt ttgtttctat cttatgatca ttacagatgg gcgtgtgtgt acgtgtttgt    7560
attggaagcg gttggaaggt gtgagatgta gagttttaaa gacttggttt gctacttgct    7620
agctcttttg gggtgagcta cttagctggt ctgagcctct gttttctcat cgttttttt     7680 ttttgtttgt ttgtttgttt ttgagacgga gtctcgctct ttcgcccagg ctggagtgct    7740
gtggcgcgat ctaggctcac tgcaagctcc gcctcccggg ttcacaccat tctcctgcct    7800
cagcctcctg agtagctggg actacaggca cccgccacca cacccggcta atttttttgt    7860 attttagta gagactgggt ttcaccatgt tagccaggat ggtctccatc tcctgacctc     7920
gtgatccgcc ctcctcggcc tcccaagtg ctgggattac aggtgtgagc caccgcaccc     7980
ggcctttctc atccttttta aagtgcagat cataatacct acttcacaag tttagggtga    8040
aaacttccta aagctgtgta gcacaactta ggccctcatt aaatgttgcc tttctaattc    8100
atatgatttg tgcccttgga aagcaagcac atgtctttct caccttcaca gtatttgttg    8160
agtatgttca cttacagtta ggaaagtgat attatccaag acctactgac taataaacca    8220
atggaagaaa aagctattca attctaaaca cgttacaaaa atctgtaaca cacaattgca    8280
cattctttgt agatgttgaa cgtcgacgca tttacgatat cgtgaacgtc ctagagagtt    8340
tacatatggt gagccgcctc gccaaaaaca ggtacacttg gcacgggcga cacaatctca    8400
acaaaaccct tggcaccttg aagagcatcg gggaggagaa taagtacgcc gagcagatta    8460
tgatgatcaa aaagaaagaa tatgagcaag agtttgactt tattaagagt tacagtatag    8520
aggatcatat catcaaatca aacactggcc caaatggaca cccagacatg tgttttgtgg    8580
aactccctgg agtggaattt cgggcaggtg agagatggta gtgaaaactc caggcggcat    8640
ggcatttgtc ctctgtctaa ggaaaaggtt ctgtggagaa cacagctcta aagctactgc    8700
tgcctttaat gttcagatgc cacagttgtc agctgtatga tcaggtggta gtattttag    8760 ccttgttact ttagaagtca cttgtcccctt tatgaatttt aattctctaa tcctcatcct   8820
tctctaaagc ttctgtaaac agccgcaaag acaagtcttt aagggtaatg agccagaaat    8880
ttgtgatgct gttttggtg tcaacgcctc agatagtaag cctagaagtt gctgccaaga     8940
ttttaattgg ggaggaccat gtggaagatt tggataaaag caagtttaaa agtaagtgtc    9000
atgactgcca tggatttttg aacctattct taaacaataa aatctcagtc gtaaactcat    9060
ttccaaatta ggaaacatag gtgcataaac agatcttctc taattatgtt tttatatctt    9120
ctccccagaa gccatgataa tattgattta gctaacttgt tatgatacat aagtatcact    9180
actctttttt tttttttttt ttttttagacg gagtctagct cttttgctag gctggagtgc    9240
agtggcgaga tctaggctca ctgcaacatc tgcctcccgg gttccagcaa ttctcctgcc    9300
tcagtctccg gagtagctgg gattacagtt gcgcgccacc acacccggct aatttttata    9360 ttttttagtgg agacggggtt tcaccatgtt ggccaggagg atctcgatct cttgacctcg   9420
tgatccaccc acctcggcct cccaaatttt gggaggcctc ccaaaattac aggcctgagc    9480
cactgcgcct ggccaagtat cactactctt atttgacaca ttgcttcatt tgatattgta    9540
```

```
acattgttct caaaagtaaa cacggccagg cgcggtggct gaagcctgta atctcagcac  9600
tttgggaggc cgaggagggc ggatcatgag gtcaggagat ccagaccaac ctggctaaca  9660
cagtgaaacc ccgtctctac taaaaataca aaaaaattag ccgggcgtgg tggcgtgcac  9720
ctgtagtccc agttactcag gaggctgagg caggagaatg gcgtgaacct gggaggcggc  9780
gcttgcagtg agccgagatc gcgccactgc actccagcct gggggacaga gcaagactct  9840
gtctcaaaaa aaaggaaaca ctagaagaat ctgttctgtg tgagctctaa atgagagtaa  9900
attgtaaagt gggtctgcac cctggtctcc ttccactgat gctgattaca gagggtttat  9960
aaatgactca taaaattgtc cccagaagtg acctgcagca caggtagtct gccattttga  10020
aagaatggtt ttagctagat tacctgctca aaattgggaa gggactgtag attggattcc  10080
taacaaaaga gctatgccct caccattaca ccagactttg caggaagggt gtggaaagaa  10140
gtgctcagcg gatggggagg agcacttggc tcgggagatc gggagatctg caatttcaga  10200
aaacacgtcc tgatactact gaggggttac ttgccttttg tgagtcaccg gatagttttc  10260
atctttgttt cactggttag tcatagcctt gaaaactatt ccaggaactg cagaggtgta  10320
agttactgaa tccccaggga attcagaacc ttctgatatg gctaggaagg agactcgatt  10380
tgtaatttgt actatcaaga tggcagtaaa aaacagactt tttgtaacaa aactctttaa  10440
gatatgtgag gtttgtcaag ttcacagatc tatgttttgc atgttacata gacagtatta  10500
aaaaattaca catgttgatg gagtacagaa ttttccatgc tgccatagta aataaatttt  10560
gttataagct attacaagca gaaaagcaag acatttatca cagatacttt tacttctctg  10620
ctcataaaat tcttctgaat cctcattaga agatacccag gaatggtgac tttattttg   10680
aaacagtctg taacatagtt tcagataggg tgatctcatc aagtcgtttt tcctttgtca  10740
acgtatgcta ttgtcatttc aacattgagt actagcagta attgagtctt ttaaatattt  10800
aaaactttt tatcttaatt aaagttgtat caccagaaga acttaaaagg aggcagatgt  10860
ttctctgtct gacattgatg gttaagacag ctcttagaat atacatgaag tccttctgaa  10920
ggaaaattct ttgatctttt cattattcca ttaagtggta tatatacttt ttttcccagc  10980
aaaaattagg aggttgtatg atatagctaa tgttctgagt agcctggatc ttatcaagaa  11040
agttcatgtt acagaggaaa gaggccgaaa accagctttc aaatgaccg gcccagaaat  11100
cagtccaaat accagtggta tgtatttttt tctttcaccc tctgctttat tatttgtgtg  11160
tgtgttttc taattttaa tttccagtgt gtgttgttcc cctccctgtg tccatgtgtt  11220
ctcattgttc aactcccact tacgagtgag aacatgcagt gtttgatttt ctattcctat  11280
gttagtttgc tgaggatgat ggcttccagc tccatccgtg tcccacagag gacatgatct  11340
catttctttt tatggctgca tagtattcca tggtgtatat gtaccacatt ttctttatcc  11400
tgctttatta ttttgaatta atgcacattg ggagatattt tcccttcccc ttcctactca  11460
ccgccccaca tggaaaagat atatatgatt gaaaagatga ttcaagatga atggcaatat  11520
agaaagtttg gctactggct ccatcagcta accaagatcc ataacaacct cccaccctgt  11580
gttcaagaag tacaatctgt atgtgaaagc attcggaaag ttgaaagcac cacaaagcat  11640
aaaacactat tgctgctatg cggcacagtg accacaacag aacctgtgcc cattgagaat  11700
atgaaatgag ttcactctgg tatcaaagta gatatttcta gccttcatct taactctgcg  11760
atgctgacat tttgcattct accaaagatc cccacccaga atcattgaaa atgcaagaa   11820
cgtgggccat gaagacagag ggaaacttag gttccattcc aagccctgcc actctggctt  11880
```

```
tgcggcctga gacaagctac ttcttcgagg attagttttc tccttggtga aatgggaaga    11940
acaatggcac ctcagtggag ttactgtgat tttggtataa tctcagagag aggtcctttc    12000
gtgcaggaat ttggagtgaa aattccgggg ccatattgac caggttcata tcccaggccc    12060
acatgctccc agttgagaga ccttgagcca gtaggttaat gtctgtgtgg gtcagagctc    12120
tcatctccga cacagggctg catttcttga ggaacagtta cctcatggag ctgtgaggat    12180
cacccatatt tcatcagatc taagacttca ctgattgtaa gatgcacaat tctttctata    12240
tcactaagaa agaaaaatca ctaataacta cactctagca caccactggt tataagatat    12300
agtgcagttt cagaaatgct aatgtaggaa atattgtgtc tcagaatcca tttaataaga    12360
taaacaaggc tttctctgta aagcccttag aacagtgaca ggcacatggt cggtgctctg    12420
taacttgcca cttttattcc taaaattgtt ttatttcata tcccaaaagc caactgagcc    12480
atccaggttt taatacacag acgttttctg tttcaggctc cagcccagtc attcatttta    12540
ctccctctga tttggaggtg agacggtctt caaaagagaa ctgtgccaaa aacctctttt    12600
ccacacgtgg gaaaccaaac tttactcgac acccatctct tatcaaattg gtaaagagta    12660
tagaaagtga tcggagaaag ataaaattctg cgcccagtag ccctatcaag accaacaaag    12720
gtatgttttc aggaatgtca gggatctgct aggaagaatt ccctttttatc tcattttttc    12780 agcttacttg atccttgcaa tagttgtcag agaattattt caatatctat atacccaaac    12840
cctcttgaag cctaactaat gtataaattt aaaaagtcat ttgtggggtt tattgtttaa    12900
tcgctatgca actttgaggg gaggtgcaca cttctgttc ctctgacttc agtgaggttt    12960
catctgtgtg aacatttgtt ctttagcttt gaccggtgct ctcttccttt ctattttacc    13020
agctgagagt tctcagaatt ctgcacccctt cccaagtaaa atggctcagc tcgcagctat    13080
ttgtaaaatg cagttagaag agcaatcaag gtaggttggc aatcctcttt aataacagga    13140
tgaattactt ttacattaca ttgttaggat tacttatttt atgtgagaag aagccctagc    13200
cttgaactgg agagctaatc ttttctgtat ctcatactca ctcattacag aaattatctg    13260
catgttccat aaaagcgtgg cttcaatatg aggcttaaag cggtagaaca gttcagaaaa    13320
aatgtatatc catcatgtcg tgtattaaat cttgtctttc agtgaatcca gacagaaagt    13380
gaaagtacag ctggcaagat ctggaccctg caaaccagta gccccctctgg acccccagt    13440 gaatgctgag atggagctga cagcaccgtc cctcatccag ccctgggaa tggttccct    13500 gatccccagc cccttgtcat cagcagtgcc cctgatccta cctcaggccc cttcaggccc    13560
atcctatgcc atctacctgc agcccactca agcccaccaa agtgtgacgc caccccaagg    13620
cctgagccca acggtgtgca ccacccactc ttctaaagct actggctcaa aagactccac    13680
agatgccacc actgagaagg cagccaatga tacctcaaag gccagtgcct ctaccaggcc    13740
tggaagcttg ctgccagcac cagagaggca aggggcaaag agccgaacca gggagccagc    13800
tggagaaaga ggctcaaaga gggcaagcat gctcgaggac agtggttcca aaaagaaatt    13860
taaagaggac ctaaaaggac ttgaaaatgt ctccgcagta agtacagcct tgaactgcac    13920
aaagctttag gaattcccta gtctattaca ggaagattgg tggcttgtga aatttaccga    13980
agagcattct ctcagaagac aaggaactgt tccttagcat cccataatcc aagtgaggcc    14040
ctcaacagct aatccctgg ctgggatgaa ggcaggaca ttttttaacct ttggaggaag    14100 ggattatttg ctgtcttttt aaagtaccat gggtggttgt ccttaagtcc atttctccat    14160
cacacactgg aatgcaaaca gctgtcatga aagtcttaaa taatttacaa gcagacgtaa    14220
ccccaaatga acgtgtggat gcataggggtt cctgtaactc ctgctttctg agtcattacc    14280
```

```
taatgtttgt tgttgtcat gtaactggca tctgttgcct agaagataaa ttgctccccg    14340 ttttttacttt ctacctaaaa tttaaatcaa aatttctatt tcatgtaaat agaaaaatca   14400
aactgatctt ggcaaattgt agatatagtt catgtattgg tttctagaga ttttgacatg   14460
ctagacaaat ttttttccta agtggagatt agttccggag ggaattaata tttattggat   14520
gcctacccac atatagcaga cataatagat attagtcact tttacataca gtatctcatt   14580
ttcctccctt aggacaatta tatatgagag acattactgt atcatccgat aaataccact   14640
aaatgtgcaa gtaaaagtta atctctcatt ttgcccctgc tcttaataca agctatttta   14700
cttctctctg tcttattttt ccgcatcggt aaagaattta ttccaccagt ttttcctcat   14760
cacctactgg atataaagca ctgtgctctg gatcaaatct aacccagcac ctgcctttgg   14820
tggcaattgc ttttgggtac ttgcctgtgg gcatatgata gttttttgtgg ggttaagtga   14880 atttattcca tgatgataca cataaaaggg tttgatcctt ttaagacgtg ttataagctg   14940
aaaggtatta tctgttacgt tgttattaaa gaggaagctt agagtttgtc aaatcttccc   15000
tgaggatggc ctcatggtaa ccattcaaaa catctattat cttacatagt atccttttgt   15060
atttaatgta tatgccaagt gggaaatcat aaggtttcaa tattctggaa ggtccataac   15120
ttcttttggc caatgggtat gatttaataa tggtctcctg ttgcttacat agttattcag   15180
gattaggatt ttcagtggat agattttcca tatactcctg cttctttttt atatctctgc   15240
aactctaacc atttcttttt tcttttgaga cagggtctta ctctgtcacc cagaatggag   15300
tgcagtggca tgattttagc tcactgcagc ctcgacctcc aaggcttaag tgatcctccc   15360
acctcagtct cccaagtaac ttagactaca ggtgtgctgc catgcccggc taattttta   15420 tttttttgtgg agacggggtt tcaccatgtt gctcagcctg gtctcgaact cctgagctca   15480
agcagtctgc ctgccttggc ttcccaaagt gctgagatca caggcatttg ccgtcatgcc   15540
cagcccactt taaccatttc gttttagtat ggcctgagca aaacaaagac aatgagagag   15600
tcatgtgtta attcattcaa caaatttta ctgagaattt atacttctag gggtggaaag   15660
aagataagta tgcaagtaaa cacaaacata tcaggtagtg aatgatagga atgaagatga   15720
catgatagga ggaagggtg gaagggctac tgtaggctag aagagttcaa gttcaaatat   15780
gtcagattca ttcggcaatt taatagttct aattattta taaaaaggg aattggcata   15840 ggttaaaaga ttctataatg aatatagttt gttggaaatt taaaaattat tattctatta   15900
ttgtgggttt tactgaagac ttgaaagagt taaaccagca gtcagaataa tttgtaccat   15960
gagagaatat aactaaagct aatagagcgc aggtcttcat aaagcaccta aatttgcccc   16020
ttaaaaattc tctcttcctg cagttttcaa ggcacctact agtagagatt ttgagtggga   16080
ccaagtactt aagaaacaaa attaaaagct tgtagtatac tttagctttt gtggattctg   16140
aatttcctgg ttcccaagga aaagacctat taacaactag attaaacttg ttttgacaat   16200
ggagagaaga aaggtctgaa ggaagaaaaa aggaggtccc tagtttataa gagcggtttt   16260
tagcttttgc cagtcccgct catggtaagg ctaaagcaga cttttcatgc agttcaggca   16320
cccgtgtaaa cttttttctgt ttgggaaagt acagtgatct aataggcatg ttgggaggta   16380
catgcaaccc tacccttggg ccttttctag ttgcaatata actttattgc ctaaagcttt   16440
tgctcaatgg catgtgcgtc tctaatatga attaatcagt tctcttattt gtaattttt   16500 taactctggt gtactttgcg tattttaaga ctgcttgtta tcattagagc aagcagtact   16560
agaaagaaat ctttacttat ataatttctg ttttaaatca ggggccagca aacgttcttt   16620
```

```
aaagggccag atagtagaca ttttttgggt tttaaggcca tatgggctct gttgcaccta   16680
gtcaactctg ccattgtagc aggaaagttg ctataggcag tacataaatg aatgagtatg   16740
attgtgttcc aatgaaactt tatttataaa acaggcagg gagtgggaat tggcacatgg    16800
ccaatagttt agccccctttc tctaaatca atgtcattta aagtgtttcc ttagaatact   16860
agtcctcctt aattgcctac tgaaaatata gttgccaaat agtttgggaa atgctacctg   16920
ctgtgtgccc cacttggaga attttaaggc atgccaccat taaaatctct tggaaattct   16980
ctaataaaga caccatttga ctttgtttaa ttcagtattt tccaattata tttgaccaag   17040
aatcaggtaa tgcctgtttg caacccatgg acctcaggtc cctcagaatg ccctttggga   17100
aataccgttc tacataattc aagaacaatc aattactact acatcatacc aaggagtcca   17160
gtagcaagag ttaagttatc agtttaagag tggtgtgctg gatgaatcct tacccctaag   17220
cagggtcagt gccatcatcc aaaggtgtcc taagaccaca ggtggcattt aagaaacatg   17280
ttctgcatta ttcggggcaa gcattgggaa gggtgggagg gtattctcct ctaggagcca   17340
ggtgaccagc ctgcctgcag cccactccgc tggaggcttt ggtccaatga ggcaaccacc   17400
aagggatatt agtcctgaaa gaggcacgtg gccattttc ttcctgtatt tgtgtgtaaa    17460
ataaaccctt cctccttgtt ttctagacct tgttcccatc aggataccta atccctctca   17520
cgcagtgctc atccctgggg gcagagtcca ttttgtctgg taaagaaaac tcaagtgctc   17580
tttccccaaa ccacaggatt tacagctccc caattgcagg tgagtgcaca taaaacacta   17640
accagatgtg ggccggtctc aagttcactt aagccttgtc aacttcttgg ataaatgcct   17700
gtgcttttaa gatatcttcc ccctttcct tccaggtgtt attccagtga catcatctga    17760
actcactgct gttaattttc cctcttttca tgtaacaccg ttgaagctaa tggtctcacc   17820
aacttccgtg gcagccgtac ctgtcgggaa cagcccggct ctcgcttcaa gccaccctgt   17880
tcccatccag aacccaagct cagccattgt aaacttcacc ctgcagcacc tgggactcat   17940
ctcacccaat gtgcagttgt ctgccagccc tgggtctgga atcgttcctg tgtctccaag   18000
aatagagtct gttaatgtcg caccagaaaa tgcaggcact cagcaaggaa gggccaccaa   18060
ctatgactca ccagtcccag gccagagcca gccaaatgga caatcagttg ctgtgacagg   18120
ggcacaacag gtgagaggct ttctacttaa tttaattttt cctggaatta ctaagcccca   18180
agtatctgtg tcataagaga ttggcttttg cttttcctct ttggagaggg aaaggatggg   18240
aaagtcagga gattgaaggc ctatgtttct tccagaaccc aggaagagtg tccaaggcat   18300
ccatattgtt gggttatcat gagattttg tctctcccct aacaaaaata attgagaatg    18360
taaaactcac caaagcttcc ctcgccaatt tcaagatacg ccagtttccc atgtgcaata   18420
cattcatcca gcccaatctt ccaagtctgg taagactatg tacctgtgtg tggttgactt   18480
cttttgtcca ttcttctctt tccaatcagc ctgttcctgt gacacccaaa gggtcacaat   18540
tagtggccga aagtttcttc cgtaccccag gtggacccac caagccaacc agctcatcct   18600
gcatggattt tgagggtgct aataaaacct ccttaggaac tctctttgtc ccacagcgaa   18660
aactggaagt ctcaacagag gatgtccatt aatcaacaga tgttggctta gtttaatttt   18720
ctaaagagtt gtttaataga gaaatgtac acagactgat ttggagaaca cattctctga    18780
aaatactgta aatacgttgg ggatttgttc aatgtgaaat cagatagttg ttttcataca   18840
tatatatata tacacacaca cacacacaca cacacacaca tatatttgta taaagctaag   18900
tttagctttc aatcctacaa aataaaagta aaatgttgaa ctctaagata tattaacttc   18960 taggggggaaa aatccattat tttagctatg cctatactat tatgcaaagt aactgtatta  19020
```

```
aagtttactt ccctctaagc aaatatgctt gacatgccta acacagcatt cccttaaaca    19080
ttttgcacaa agaaaatgct gtgtgatgta taatgttgta tttttaaata ggggtatagc    19140
tatatttttt gtaatttctt taatctgttg ttgcagtgta tcttttgta aagtttgcaa     19200 caatcctcaa tcaagtctat ggaaaaatta tttataaaat gtatttttaa tcataagttg    19260
ttcaaattaa aacttttcta aaatatagtt agcattttca tttcgccggt tagggcactg    19320
ttgggagaaa attaaaattt acctaatcac agaggcaaat tcttagtaaa gagtatccat    19380
gctgggttcc attagatatg caaagtttat agaatgtttc tacattctgt cccccatttt    19440
gacccttgag attgctccac ttttgcagaa gtaaaattgg ctttggagag gttgttgctt    19500
ggccaagaac acctagctaa gtcccatgtg cttcctacca cactccacga gattagaaat    19560
gaaaggtagg cgcctagggg ccctggtgtg accagcatct gtcccacgct tcctgctcta    19620
ctcagaggtg ggtctgtacc agctctctta acatacttct tggatggccc agctccaggg    19680
acaggaaaac ggcagtaagg attctaatgt cctccacacc tggagaaccc ccaggagctc    19740
caagagaagg gacaagttcc agtgtgttaa gtgtgcatct ctttgacccg tttgttatgg    19800
gaagaactgc accttgagaa ttgacaagtg cttttccctgg ttagggtctt aaaggagcat   19860
catagtatct atttcctaca tgtttactat atgtagacag ggttatacgt tttaaatgta    19920
tcatatctgt gagctacaac tgaggctcac agggattaaa gcaacaagtc catggtcaca    19980
ctgctagtgt atgcaagtct cagctcatgt ctattggacc tcattatcca ttgcccattt    20040
acttctagag acatgcctag cagctctagt aggaatcaag cacattgatt cagggtaat     20099
```

US 7,795,416 B2

TELOMERASE EXPRESSION REPRESSOR PROTEINS AND METHODS OF USING THE SAME

CROSS-REFERENCE TO RELATED APPLICATIONS

Pursuant to 35 U.S.C. §119 (e), this application claims priority to the filing date of the U.S. Provisional Patent Application Ser. Nos.: (a) 60/300,115 filed Jun. 21, 2001; and (b) 60/366,069 filed Mar. 19, 2002; the disclosures of which are herein incorporated by reference.

INTRODUCTION

1. Field of the Invention

The field of this invention is the telomerase reverse transcriptase gene, specifically the regulation of the expression thereof.

2. Background of the Invention

Telomeres, which define the ends of chromosomes, consist of short, tandemly repeated DNA sequences loosely conserved in eukaryotes. Human telomeres consist of many kilobases of (TTAGGG)n together with various associated proteins. Small amounts of these terminal sequences or telomeric DNA are lost from the tips of the chromosomes during S phase because of incomplete DNA replication. Many human cells progressively lose terminal sequence with cell division, a loss that correlates with the apparent absence of telomerase in these cells. The resulting telomeric shortening has been demonstrated to limit cellular lifespan.

Telomerase is a ribonucleoprotein that synthesizes telomeric DNA. Human telomerase is made up of two components: (1) an essential structural RNA (TER) (where the human component is referred to in the art as hTER); and (2) a catalytic protein (telomerase reverse transcriptase or TERT) (where the human component is referred to in the art as hTERT). Telomerase works by recognizing the 3' end of DNA, e.g., telomeres, and adding multiple telomeric repeats to its 3' end with the catalytic protein component, e.g., hTERT, which has polymerase activity, and hTER which serves as the template for nucleotide incorporation. Of these two components of the telomerase enzyme, both the catalytic protein component and the RNA template component are activity limiting components.

Because of its role in cellular senescence and immortalization, there is much interest in the development of protocols and compositions for regulating expression of telomerase.

Relevant Literature

U.S. patents of interest include: U.S. Pat. Nos. 6,093,809; 6,054,575; 6,013,468; 6,007,989; 5,958,680; 5,876,979; 5,858,777; 5,837,857; 5,583,016; 4,816,397; 4,816,567; 5,693,780; 5,681,722; 5,658,570; 5,750,105; 5,756,096; 5,464,764; and 5,627,052. Also of interest are WO 99/33998 and WO 99/35243. Articles of interest include: Takakura et al., Cancer Res. (1999) 59:551-7; Cong et al., Hum. Mol. Genet. (1999) 8:137-142; Wu et al., Nat. Genet. (1999) 21:220-224; and Horikawa et al., Abstract #1429, Scientific Proceedings, 91st Annual Meeting of American Association for Cancer Research, San Francisco, Calif. Apr. 1-5, 2000. See also GENBANK accession nos. AF114847 and 128893.

All of the patents and publications cited are incorporated herein by reference in their entirety.

SUMMARY OF THE INVENTION

Telomerase repressor proteins and nucleic acid compositions encoding the same are provided. The subject repressor proteins bind to a repressor site in the TERT minimal promoter, e.g., a Site C site, and thereby inhibit TERT expression. Also provided are methods of modulating, e.g., inhibiting or enhancing, TERT expression. The subject invention finds use in a variety of different applications, including therapeutic and therapeutic agent screening applications.

BRIEF DESCRIPTION OF THE DRAWINGS

FIG. 2 provides the amino acid sequence (SEQ ID NO:09) and the sequence of a nucleic acid sequence (SEQ ID NO:08) that includes a coding sequence for the F13 TERT repressor.

FIG. 3 provides the amino acid sequence (SEQ ID NO:11) of the F13H TERT repressor.

FIG. 4 provides a nucleic acid coding sequence (SEQ ID NO:11) for the F13H TERT repressor.

FIG. 5 provides the genomic nucleotide sequence (SEQ ID NO:12) for the F13H TERT repressor.

FIG. 6 provides an alignment of the amino acid sequence of F13H with F13.

FIG. 7 provides a diagram of the F13H and F13 proteins, where the diagram shows to the E2F binding domains on each protein.

DESCRIPTION OF THE SPECIFIC EMBODIMENTS

Figure 1:
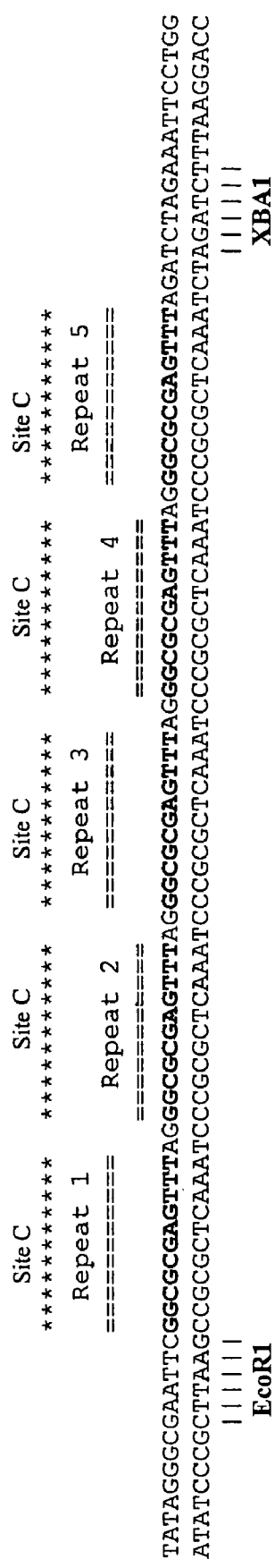
FIG. 1 provides a schematic view of a Site C bait fragment used in the one hybrid assay system described in the experimental section, infra.

Telomerase repressor proteins and nucleic acid compositions encoding the same are provided. The subject repressor proteins bind to a repressor site in the TERT minimal promoter, e.g., a Site C site, and thereby inhibit TERT expression. Also provided are methods of modulating, e.g., inhibiting or enhancing, TERT expression. The subject invention finds use in a variety of different applications, including therapeutic and therapeutic agent screening applications. In further describing the subject invention, the subject polypeptide and nucleic acid compositions are described first, followed by a discussion of various utilities of the subject applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the elements that are described in the publications which might be used in connection with the presently described invention.

Telomerase Repressor Polypeptide Compositions

As summarized above, the subject invention provides telomerase repressor polypeptides, i.e., polypeptides that repress telomerase expression. The term polypeptide composition as used herein refers to both full-length proteins as well as portions or fragments thereof. Also included in this term are variations of the naturally occurring proteins, where such variations are homologous or substantially similar to the naturally occurring protein, as described in greater detail below, be the naturally occurring protein the human protein or a protein from some other species that naturally expresses repressor protein, usually a mammalian species. In the following description of the subject invention, the name for a given repressor protein is used to refer not only to the human form of the protein, but also to homologs thereof expressed in non-human species, e.g., murine, rat, monkey and other mammalian species.

The subject repressor proteins are characterized by having TERT repressor activity. Specifically, the subject proteins bind to a repressor binding site present in the TERT minimal promoter. More specifically, the subject proteins bind to a "Site C" repressor binding site present in the human TERT minimal promoter. The human TERT Site C binding site is located in the region −80 to −50, and particularly −69 to −57 of the human TERT minimal promoter, and the subject repressor proteins bind to this site, where the sequence of this site is: GGCGCGAGTTTCA (SEQ ID NO:01). When binding to this site, or a portion thereof, the subject repressor proteins inhibit expression of TERT, where by inhibit expression is meant that expression of TERT is reduced by at least about 50%, usually at least about 75% and more usually at least about 90% as compared to a control system where TERT expression occurs and that is identical but for the absence of the subject repressor protein. The subject repressor proteins may be glycosylated, or modified in alternative ways.

The F13 proteins range in length from about 600 to 950, usually from about 650 to 800 and more usually from about 650 to 750 amino acid residues, and the projected molecular weight of the subject proteins based solely on the number of amino acid residues in the protein ranges from about 70 to 120, usually from about 85 to 115 and more usually from about 95 to 105 kDa. As the subject F13 proteins may be glycosylated, or modified in alternative ways, the actual molecular weight of these proteins may be substantially higher than the above projected molecular weights, typically ranging from about 2 to 4 times higher than the projected molecular weight. As such, the actual molecular weight typically ranges from about 200 to 400 kDa, usually from about 250 to 350 kDa and more usually from about 275 to 325 kDa, e.g. about 300 kDa.

The subject F13 proteins include two E2F "like" DNA binding domains. The first E2F-"like" binding domain is an approximately 90 residue long amino acid stretch near the N-terminus of the protein starting at amino acid residue 141. This E2F-"like" binding domain has a 41% overall sequence identity with the DNA binding domain of human transcription factor E2F-2 (accession no. AL021154) and this homology extends slightly into the leucine zipper (protein-protein interaction) domain of human E2F-2. The second E2F DNA binding domain identified in F13 is a 100 residue long amino acid stretch (272 to 376 amino acid residues) and has a 27% overall sequence identity with the DNA binding domain of human E2F-2. In many embodiments, the above described E2F-"like" DNA binding domains are desired for binding to site C.

Of particular interest in certain embodiments is the human F13 protein, where the human F13 protein of the subject invention has an amino acid sequence that is substantially the same as, or identical to, the sequence appearing as SEQ ID NO:09, infra.

By "substantially the same as" is meant a protein having a sequence that has at least about 50%, usually at least about 60% and more usually at least about 75%, and in many embodiments at least about 80%, usually at least about 90% and more usually at least about 95%, 96%, 97%, 98% or 99% sequence identity with the sequence of the above provided sequences, as measured by the BLAST compare two sequences program available on the NCBI website using default settings.

In addition to the specific TERT repressor proteins described above, homologs or proteins (or fragments thereof) from other species, i.e., other animal species, are also provided, where such homologs or proteins may be from a variety of different types of species, usually mammals, e.g., rodents, such as mice, rats; domestic animals, e.g. horse, cow, dog, cat; and primates, e.g., monkeys, baboons, humans etc. By homolog is meant a protein having at least about 35%, usually at least about 40% and more usually at least about 60% amino acid sequence identity to the specific human transcription repressor factors as identified above, where sequence identity is determined using the algorithm described supra. One homolog of particular interest is the F13H homolog disclosed herein as SEQ ID NO:11.

The TERT repressor proteins of the subject invention are present in a non-naturally occurring environment, e.g., are separated from their naturally occurring environment. In certain embodiments, the subject proteins are present in a composition that is enriched for the subject proteins as compared to the subject proteins in their naturally occurring environment. As such, purified repressor proteins according to the subject invention are provided, where by purified is meant that the proteins are present in a composition that is substantially free of non repressor proteins of the subject invention, where by substantially free is meant that less than 90%, usually less than 60% and more usually less than 50% of the composition is made up of non-repressor proteins of the subject invention.

In certain embodiments of interest, the repressor proteins are present in a composition that is substantially free of the constituents that are present in its naturally occurring environment. For example, a human repressor protein comprising composition according to the subject invention in this embodiment will be substantially, if not completely, free of those other biological constituents, such as proteins, carbohydrates, lipids, etc., with which it is present in its natural environment. As such, protein compositions of these embodiments will necessarily differ from those that are prepared by purifying the protein from a naturally occurring source, where at least trace amounts of the constituents or other components of the protein's naturally occurring source will still be present in the composition prepared from the naturally occurring source.

The repressor proteins of the subject invention may also be present as isolates, by which is meant that the proteins are substantially free of both non-repressor proteins and other naturally occurring biologic molecules, such as oligosaccharides, polynucleotides and fragments thereof, and the like, where substantially free in this instance means that less than 70%, usually less than 60% and more usually less than 50% (by dry weight) of the composition containing the isolated repressor proteins is a non-repressor protein naturally occurring biological molecule. In certain embodiments, the repressor proteins are present in substantially pure form, where by substantially pure form is meant at least 95%, usually at least 97% and more usually at least 99% pure.

In addition to the naturally occurring proteins, polypeptides that vary from the naturally occurring proteins are also provided. By polypeptide is meant proteins having an amino acid sequence encoded by an open reading frame (ORF) of a repressor protein gene, described below, including the full length protein and fragments thereof, particularly biologically active fragments and/or fragments corresponding to functional domains, and including fusions of the subject polypeptides to other proteins or parts thereof, e.g., immunoglobulin domains, nuclear localization domains (such as a VP22 domain as described in U.S. Pat. No. 6,358,739, the disclosure of which is herein incorporated by reference); and the like. Fragments of interest will typically be at least about 10 aa in length, usually at least about 50 aa in length, and may be as long as 300 aa in length or longer, but will usually not exceed about 1000 aa in length.

Also provided by the subject invention are ligands having TERT Site C binding activity. The term ligand, as used herein, refers to any compound capable of binding to a TERT repressor site, particularly Site C, and as such includes proteins and peptides, oligosaccharides, and the like, as well as binding mimetics thereof, including small molecule binding mimetics thereof. The subject ligands are capable of binding to Site C in a manner analogous to the binding activity of the subject repressor proteins, and will generally comprise the functional TERT promoter binding domain, e.g., Site C binding domain, of a repressor protein according to the subject invention, or the functional equivalent thereof.

Nucleic Acid Compositions

Also provided are nucleic acid compositions that encode TERT expression repressor polypeptides and fragments thereof, etc., as described above. Specifically, nucleic acid compositions encoding the subject polypeptides, as well as fragments or homologs thereof, are provided. By "nucleic acid composition" is meant a composition comprising a sequence of nucleotide bases that encodes a polypeptide according to the subject invention, i.e., a region of genomic DNA capable of being transcribed into mRNA that encodes a repressor polypeptide, the mRNA that encodes and directs the synthesis of a repressor polypeptide, etc. Specific nucleic acids of interest include those identified herein as SEQ ID NO:08; SEQ ID NO:10 and SEQ ID NO:12. Also encompassed in this term are nucleic acids that are homologous, substantially similar or identical to the nucleic acids specifically disclosed herein, e.g., SEQ ID NO:08; SEQ ID NO:10 and SEQ ID NO:12.

Also provided are nucleic acids that are homologous to the provided nucleic acids, at least with respect to the coding regions thereof. The source of homologous nucleic acids to those specifically listed above may be any mammalian species, e.g., primate species, particularly human; rodents, such as rats and mice, canines, felines, bovines, equines, etc; as well as non-mammalian species, e.g., yeast, nematodes, etc. Between mammalian species, e.g., human and mouse, homologs have substantial sequence similarity, e.g., at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17). Unless indicated otherwise, the sequence similarity values reported herein are those determined using the above referenced BLAST program using default settings. The sequences provided herein are essential for recognizing TERT repressor related and homologous polynucleotides in database searches. Of particular interest in certain embodiments are nucleic acids including a sequence substantially similar to the specific nucleic acids identified above, where by substantially similar is meant having sequence identity to this sequence of at least about 90%, usually at least about 95% and more usually at least about 99%.

Also provided are nucleic acids that hybridize to the above described nucleic acids under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5× Denhardt's solution, 10% dextran sulfate, and 20 μg/ml denatured, sheared salmon sperm DNA, followed by washing the filters in 0.1×SSC at about 65° C. Stringent hybridization conditions are hybridization conditions that are at least as stringent as the above representative conditions. Other stringent hybridization conditions are known in the art and may also be employed to identify nucleic acids of this particular embodiment of the invention.

Nucleic acids encoding the proteins and polypeptides of the subject invention may be cDNAs or genomic DNAs, as well as fragments thereof. The nucleic acids may also be mRNAs, e.g., transcribed from genomic DNA, that encode (i.e. are translated into) the subject proteins and polypeptides. Also provided are genes encoding the subject proteins, where the term "gene" means the open reading frame encoding specific proteins and polypeptides, and introns that are present in the open reading frame, as well as adjacent 5' and 3' non-coding nucleotide sequences involved, e.g., untranslated regions, promoter or other regulatory elements, etc., in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements at least include exons. Normally mRNA species have contiguous exons, with the intervening introns, when present, being removed by nuclear RNA splicing, to create a continuous open reading frame encoding a repressor protein according to the subject invention.

A genomic sequence of interest comprises the nucleic acid present between the initiation codon and the stop codon, as defined in the listed sequences, including all of the introns that are normally present in a native chromosome. It may further include specific transcriptional and translational regulatory sequences, such as promoters, enhancers, etc., including about 1 kb, but possibly more, of flanking genomic DNA at either the 5' and 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject proteins and polypeptides, described in greater detail above. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt.

The TERT repressor genes of the subject invention are isolated and obtained in substantial purity, generally as other than an intact chromosome. Usually, the DNA will be obtained substantially free of other nucleic acid sequences that do not include a TERT repressor protein sequence or fragment thereof, generally being at least about 50%, usually at least about 90% pure and are typically "recombinant," i.e. flanked by one or more nucleotides with which it is not normally associated on a naturally occurring chromosome.

In addition to the plurality of uses described in greater detail in following sections, the subject nucleic acid compositions find use in the preparation of all or a portion of the subject polypeptides, as described above.

Also provided are nucleic acid probes, as well as constructs, e.g., vectors, expression systems, etc., as described more fully below, that include a nucleic acid sequence as described above. Probes of the subject invention are generally fragments of the provided nucleic acid. The probes may be a large or small fragment, generally ranging in length from about 10 to 100 nt, usually from about 15 to 50 nt. In using the subject probes, nucleic acids having sequence similarity are detected by hybridization under low stringency conditions, for example, at 50° C. and 6×SSC (0.9 M sodium chloride/ 0.09 M sodium citrate)(or analogous conditions) and remain bound when subjected to washing at higher stringency conditions, e.g., 55° C. in 1×SSC (0.15 M sodium chloride/0.015 M sodium citrate) (or analogous conditions). Sequence identity may be determined by hybridization under stringent conditions, for example, at 50° C. or higher and 0.1×SSC (15 mM sodium chloride/01.5 mM sodium citrate)(or analogous conditions). Nucleic acids having a region of substantial identity to the provided nucleic acid sequences bind to the provided sequences under stringent hybridization conditions. By using probes, particularly labeled probes of DNA sequences, one can isolate homologous or related sequences.

The subject nucleic acids are isolated and obtained in substantial purity, generally as other than an intact chromosome. As such, they are present in other than their naturally occurring environment. Usually, the DNA will be obtained substantially free of other nucleic acid sequences that do not include a repressor sequence or fragment thereof, generally being at least about 50%, usually at least about 90% pure and are typically "recombinant", i.e. flanked by one or more nucleotides with which it is not normally associated on a naturally occurring chromosome.

The subject nucleic acids may be produced using any convenient protocol, including synthetic protocols, e.g., such as those where the nucleic acid is synthesized by a sequential monomeric approach (e.g., via phosphoramidite chemistry); where subparts of the nucleic acid are so synthesized and then assembled or concatamerized into the final nucleic acid, and the like. Where the nucleic acid of interest has a sequence that occurs in nature, the nucleic acid may be retrieved, isolated, amplified etc., from a natural source using conventional molecular biology protocols.

Also provided are constructs comprising the subject nucleic acid compositions, e.g., those that include a repressor protein coding sequence, inserted into a vector, where such constructs may be used for a number of different applications, including propagation, screening, genome alteration, and the like, as described in greater detail below. Constructs made up of viral and non-viral vector sequences may be prepared and used, including plasmids, as desired. The choice of vector will depend on the particular application in which the nucleic acid is to be employed. Certain vectors are useful for amplifying and making large amounts of the desired DNA sequence. Other vectors are suitable for expression in cells in culture, e.g., for use in screening assays. Still other vectors are suitable for transfer and expression in cells in a whole animal or person. The choice of appropriate vector is well within the ability of those of ordinary skill in the art. Many such vectors are available commercially. To prepare the constructs, the partial or full-length nucleic acid is inserted into a vector typically by means of DNA ligase attachment to a cleaved restriction enzyme site in the vector. Alternatively, the desired nucleotide sequence can be inserted by homologous recombination in vivo. Typically, homologous recombination is accomplished by attaching regions of homology to the vector on the flanks of the desired nucleotide sequence. Regions of homology are added by ligation of oligonucleotides, or by polymerase chain reaction using primers that include both the region of homology and a portion of the desired nucleotide sequence, for example.

Also provided are expression cassettes that include a coding sequence. By expression cassette is meant a nucleic acid that includes a sequence encoding a subject peptide or protein operably linked to a promoter sequence, where by operably linked is meant that expression of the coding sequence is under the control of the promoter sequence.

Preparation of Polypeptides According to the Subject Invention

The subject proteins may be obtained using any convenient protocol. As such, they may be obtained from naturally occurring sources or recombinantly produced. Naturally occurring sources of the subject proteins include tissues and portions/ fractions, including cells and fractions thereof, e.g., extracts, homogenates etc., that include cells in which the desired protein is expressed.

The subject proteins may also be obtained from synthetic protocols, e.g., by expressing a recombinant gene encoding the subject protein, such as the polynucleotide compositions described above, in a suitable host under conditions sufficient for post-translational modification to occur in a manner that provides the expressed protein with TERT repression activity, e.g., Site C binding activity. For expression, an expression cassette may be employed. The expression cassette or vector will provide a transcriptional and translational initiation region, which may be inducible or constitutive, where the coding region is operably linked under the transcriptional control of the transcriptional initiation region, and under the translational control of the translational initiation region, and a transcriptional and translational termination region. These control regions may be native to a gene of the subject invention, or may be derived from exogenous sources.

Expression cassettes may be prepared comprising a transcription initiation region, the nucleic acid coding sequence or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the coding sequence. After introduction of the DNA, the cells containing the construct may be selected by means of a selectable marker, the cells expanded and then used for expression.

The subject proteins and polypeptides may be expressed in prokaryotes or eukaryotes in accordance with conventional ways, depending upon the purpose for expression. For large scale production of the protein, a unicellular organism, such as E. coli, B. subtilis, S. cerevisiae, insect cells in combination with baculovirus vectors, or cells of a higher organism such as vertebrates, particularly mammals, e.g. COS 7 cells, may be used as the expression host cells. In some situations, it is desirable to express the gene in eukaryotic cells, where the encoded protein will benefit from native folding and post-translational modifications. Small peptides can also be synthesized in the laboratory. Polypeptides that are subsets of the complete sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci.* (*USA*) (1983) 80:21-25; and Siebenlist et al., *Cell* (1980) 20:269.

Yeast. Expression systems in yeast include those described in Hinnen et al., *Proc. Natl. Acad. Sci.* (*USA*) (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154:737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284-289; Tilburn et al., *Gene* (1983) 26:205-221; Yelton et al., *Proc. Nat. Acad. Sci.* (*USA*) (1984) 81:1470-1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765-776; Miller et al., *Ann. Rev. Microbiol.* (1988) 42:177; Carbonell et al., *Gene* (1988) 73:409; Maeda et al., *Nature* (1985) 315:592-594; Lebacq-Verheyden et al., *Mol. Cell. Biol.* (1988) 8:3129; Smith et al., *Proc. Natl. Acad. Sci.* (*USA*) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47-55, Miller et al., *Generic Engineering* (1986) 8:277-279, and Maeda et al., *Nature* (1985) 315:592-594.

Mammalian Cells. Mammalian expression is accomplished as described in Dijkema et al., *EMBO J.* (1985) 4:761, Gorman et al., *Proc. Nat. Acad. Sci.* (*USA*) (1982) 79:6777, Boshart et al., *Cell* (1985) 41:521 and U.S. Pat. No. 4,399, 216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism.

Once the source of the protein is identified and/or prepared, e.g. a transfected host expressing the protein is prepared, the protein is then purified to produce the desired repressor protein comprising composition. Any convenient protein purification procedures may be employed, where suitable protein purification methodologies are described in Guide to Protein Purification, (Deuthser ed.) (Academic Press, 1990). For example, a lysate may be prepared from the original source, e.g. naturally occurring cells or tissues that express the subject repressor proteins or the expression host expressing the subject repressor proteins, and purified using HPLC, exclusion chromatography, gel electrophoresis, affinity chromatography, and the like.

Once the gene corresponding to a selected polynucleotide is identified, its expression can be regulated in the cell to which the gene is native. For example, an endogenous gene of a cell can be regulated by an exogenous regulatory sequence as disclosed in U.S. Pat. No. 5,641,670; the disclosure of which is herein incorporated by reference.

Antibodies

Also provided are antibodies that bind to the subject proteins and homologs thereof. Suitable antibodies are obtained by immunizing a host animal with peptides comprising all or a portion of the repressor protein. Suitable host animals include rat, sheep, goat, hamster, rabbit, etc. The origin of the protein immunogen may be mouse, rat, monkey etc. The host animal will generally be a different species than the immunogen, e.g. human protein used to immunize rabbit, etc.

The immunogen may comprise the complete protein, or fragments and derivatives thereof. Preferred immunogens comprise all or a part of the subject repressor protein, where these residues contain the post-translation modifications, such as glycosylation, found on the native target protein. Immunogens comprising the extracellular domain are produced in a variety of ways known in the art, e.g. expression of cloned genes using conventional recombinant methods, isolation from HEC, etc.

For preparation of polyclonal antibodies, the first step is immunization of the host animal with the target protein, where the target protein will preferably be in substantially pure form, comprising less than about 1% contaminant. The immunogen may include the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies of the subject invention may be produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using MPTS bound to an insoluble support, protein A sepharose, etc.

The antibody may be produced as a single chain, instead of the normal multimeric structure. Single chain antibodies are described in Jost et al. (1994) J.B.C. 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Methods of Modulating Tert Expression

Also provided by the subject invention are methods of modulating, including enhancing and repressing, TERT expression. As such, methods of both increasing and decreasing TERT expression are provided. In many embodiments, such methods are methods of modulating the binding of the repressor protein to a Site C site in a minimal TERT promoter, including enhancing or inhibiting binding of repressor protein to a TERT minimal promoter Site C site.

Enhancing TERT Expression

As such, methods are provided for enhancing TERT expression. By enhancing TERT expression is meant that the expression level of the TERT coding sequence is increased by at least about 2 fold, usually by at least about 5 fold and sometimes by at least about 25, about 50, or about 100 fold and in particular about 300 fold or higher, as compared to a control, i.e., expression from an expression system that is not subjected to the methods of the present invention. Alternatively, in cases where expression of the TERT gene is so low that it is undetectable, expression of the TERT gene is considered to be enhanced if expression is increased to a level that is easily detectable.

In these methods, repression of TERT expression is inhibited. By inhibited is meant that the repressive activity of the TERT site C repressor binding site/repressor interaction with respect to TERT expression is decreased by a factor sufficient to at least provide for the desired enhanced level of TERT expression, as described above. Inhibition of transcription repression by a repressor may be accomplished in a number of ways, where representative protocols for inhibiting the repression are now provided.

One representative method of inhibiting repression of transcription is to employ double-stranded, i.e., duplex, oligonucleotide decoys for a repressor protein, which bind to the repressor protein thereby preventing repressor protein binding to its target site in the TERT promoter, e.g., the Site C site of the TERT minimal promoter. These duplex oligonucleotide decoys will have at least that portion of the sequence of the TERT Site C site, e.g., as encoded by a nucleic acid having a sequence of SEQ ID NO:01, or a nucleic acid having a sequence substantially similar to identical thereto, as described above. In many embodiments, the length of these duplex oligonucleotide decoys ranges from about 5 to 5000, usually from about 5 to 500 and more usually from about 10 to 50 bases. In using such oligonucleotide decoys, the decoys are placed into the environment of the expression system and a target repressor protein, resulting in de-repression of the transcription and expression of the TERT coding sequence. Oligonucleotide decoys and methods for their use and administration are further described in general terms in Morishita et al., Circ Res (1998) 82 (10):1023-8. These oligonucleotide decoys generally include a TERT site C repressor binding site recognized by the target repressor protein, including the specific regions detailed above, where these particular embodiments are nucleic acid compositions of the subject invention, as defined above.

Instead of the above-described decoys, other agents that disrupt binding of the repressor protein to the target TERT Site C repressor binding site and thereby inhibit repression may be employed. Other agents of interest include, among other types of agents, small molecules that bind to the repressor and inhibit its binding the Site C repressor region. Alternatively, agents that bind to the Site C sequence and inhibit its binding to the repressor are of interest. Alternatively, agents that disrupt protein-protein interactions with cofactors, e.g., cofactor binding, and thereby inhibit repression are of interest. Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below. Small molecule agents of particular interest include pyrrole-imidazole polyamides, analogous to those described in Dickinson et al., Biochemistry 1999 Aug. 17; 38 (33):10801-7. Other agents include "designer" DNA binding proteins that bind Site C (without causing repression) and prevent the repressor protein from binding.

In yet other embodiments, expression of the target repressor protein is inhibited. Inhibition of target repressor protein expression may be accomplished using any convenient means, including administration of an agent that inhibits target repressor protein expression (e.g., antisense agents), inactivation of the encoding gene, e.g., through recombinant techniques, etc.

Antisense molecules can be used to down-regulate expression of the target protein in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3N—ON-5N—S-phosphorothioate, 3N—S-5N—O-phosphorothioate, 3N—CH$_2$-5N—O-phosphonate and 3N—NH-5N—O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2N—OH of the ribose sugar may be altered to form 2N—O-methyl or 2N—O-allyl sugars, which provides resistance to degradation without comprising affinity. Modification of the heterocyclic bases must maintain proper base pairing. Some useful substitutions include deoxyuridine for deoxythymidine; 5-methyl-2N-deoxycytidine and 5-bromo-2N-deoxycytidine for deoxycytidine. 5-propynyl-2N-deoxyuridine and 5-propynyl-2N-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43-56.

In another embodiment, the target repressor protein gene is inactivated so that it no longer expresses the target repressor protein. By inactivated is meant that the gene, e.g., coding sequence and/or regulatory elements thereof, is genetically modified so that it no longer expresses a protein, or at least a functional protein. The alteration or mutation may take a number of different forms, e.g., through deletion of one or more nucleotide residues in the repressor region, through exchange of one or more nucleotide residues in the repressor region, and the like. One means of making such alterations in the coding sequence is by homologous recombination. Methods for generating targeted gene modifications through homologous recombination are known in the art, including those described in: U.S. Pat. Nos. 6,074,853; 5,998,209; 5,998,144; 5,948,653; 5,925,544; 5,830,698; 5,780,296; 5,776,744; 5,721,367; 5,614,396; 5,612,205; the disclosures of which are herein incorporated by reference.

The above-described methods of enhancing TERT expression find use in a number of different applications. In many applications, the subject methods and compositions are employed to enhance TERT expression in a cell that endogenously comprises a TERT gene, e.g., for enhancing expression of hTERT in a normal human cell in which TERT expression is repressed. The target cell of these applications is, in many instances, a normal cell, e.g. a somatic cell. Expression of the TERT gene is considered to be enhanced if, consistent with the above description, in those cells that detectably express TERT, expression is increased by at least about 2 fold, usually at least about 5 fold and often by at least about 25, about 50, about 100 fold or higher, as compared to a control, e.g., an otherwise identical cell not subjected to the subject methods, or becomes detectable from an initially undetectable state, as described above. Alternatively, in those cells that initially do not detectably express TERT, TERT expression is enhanced to at least a detectable level.

A more specific application in which the subject methods find use is to increase the proliferative capacity of a cell. The term "proliferative capacity" as used herein refers to the number of divisions that a cell can undergo, and preferably to the ability of the target cell to continue to divide where the daughter cells of such divisions are not transformed, i.e., they maintain normal response to growth and cell cycle regulation. The subject methods typically result in an increase in proliferative capacity of at least about 1.2-2 fold, usually at least about 5 fold and often at least about 10, 20, 50 fold or even higher, compared to a control. As such, yet another more specific application in which the subject methods find use is in the delay of the occurrence of cellular senescence. By practicing the subject methods, the onset of cellular senescence may be delayed by a factor of at least about 1.2-2 fold, usually at least about 5 fold and often at least about 10, 20, 50 fold or even higher, compared to a control.

Methods of Inhibiting TERT Expression

As mentioned above, also provided are methods for enhancing repressor protein mediated repression of TERT expression, and thereby inhibiting TERT expression. In such methods, the amount and/or activity of the target repressor protein is increased so as to enhance its repression of TERT expression. A variety of different protocols may be employed to achieve this result, including administration of an effective amount of the repressor protein or analog/mimetic thereof, an agent that enhances expression of, or an agent that enhances the activity of, the repressor protein.

As such, the nucleic acid compositions of the subject invention find use in situations where one wishes to enhance a repressor protein activity in a host. The genes, gene fragments, or the encoded proteins or protein fragments are useful in gene therapy to treat disorders in which inhibition of TERT expression is desired, including those applications described in greater detail below. Expression vectors may be used to introduce the gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or protein may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells.

Therapeutic Applications of TERT Expression Modulation

The methods also find use in a variety of therapeutic applications in which it is desired to modulate, e.g., increase or decrease, TERT expression in a target cell or collection of cells, where the collection of cells may be a whole animal or portion thereof, e.g., tissue, organ, etc. As such, the target cell(s) may be a host animal or portion thereof, or may be a therapeutic cell (or cells) which is to be introduced into a multicellular organism, e.g., a cell employed in gene therapy. In such methods, an effective amount of an active agent that modulates TERT expression, e.g., enhances or decreases TERT expression as desired, is administered to the target cell or cells, e.g., by contacting the cells with the agent, by administering the agent to the animal, etc. By effective amount is meant a dosage sufficient to modulate TERT expression in the target cell(s), as desired.

In the subject methods, the active agent(s) may be administered to the targeted cells using any convenient means capable of resulting in the desired enhancement of TERT expression. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. oligonucleotide decoy, it may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells. For nucleic acid therapeutic agent, a number of different delivery vehicles find use, including viral and non-viral vector systems, as are known in the art.

Those of skill in the art will readily appreciate that dose levels can vary as a function of the specific compound, the nature of the delivery vehicle, and the like. Preferred dosages for a given compound are readily determinable by those of skill in the art by a variety of means.

The subject methods find use in the treatment of a variety of different conditions in which the modulation, e.g., enhancement or inhibition, of TERT expression in the host is desired. By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

As indicated above, the subject invention provides methods of treating disease conditions resulting from a lack of TERT expression and methods of treating disease conditions resulting from unwanted TERT expression. Representative disease conditions for each category are now described in greater detail separately.

Treatment of Disease Conditions by Increasing TERT Expression

One representative disease condition that may be treated according to the subject invention is Progeria, or Hutchinson-Gilford syndrome. This condition is a disease of shortened telomeres for which no known cure exists. It afflicts children, who seldom live past their early twenties. In many ways progeria parallels aging itself. However, these children are born with short telomeres. Their telomeres don't shorten at a faster rate; they are just short to begin with. The subject methods can be used in such conditions to further delay natural telomeric shortening and/or increase telomeric length, thereby treating this condition.

Another specific disease condition in which the subject methods find use is in immune senescence. The effectiveness of the immune system decreases with age. Part of this decline is due to fewer T-lymphocytes in the system, a result of lost replicative capacity. Many of the remaining T-lymphocytes experience loss of function as their telomeres shorten and they approach senescence. The subject methods can be employed to inhibit immune senescence due to telomere loss. Because hosts with aging immune systems are at greater risk of developing pneumonia, cellulitis, influenza, and many other infections, the subject methods reduce morbidity and mortality due to infections.

The subject methods also find use in AIDS therapy. HIV, the virus that causes AIDS, invades white blood cells, particularly CD4 lymphocyte cells, and causes them to reproduce high numbers of the HIV virus, ultimately killing cells. In response to the loss of immune cells (typically about a billion per day), the body produces more CD8 cells to be able to suppress infection. This rapid cell division accelerates telomere shortening, ultimately hastening immune senescence of the CD8 cells. Anti-retroviral therapies have successfully restored the immune systems of AIDS patients, but survival depends upon the remaining fraction of the patient's aged T-cells. Once shortened, telomere length has not been naturally restored within cells. The subject methods can be employed to restore this length and/or prevent further shortening. As such the subject methods can spare telomeres and is useful in conjunction with the anti-retroviral treatments currently available for HIV.

Yet another type of disease condition in which the subject methods find use is cardiovascular disease. The subject methods can be employed to extend telomere length and replicative capacity of endothelial cells lining blood vessel walls (DeBono, Heart 80:110-1, 1998). Endothelial cells form the inner lining of blood vessels and divide and replace themselves in response to stress. Stresses include high blood pressure, excess cholesterol, inflammation, and flow stresses at forks in vessels. As endothelial cells age and can no longer divide sufficiently to replace lost cells, areas under the endothelial layer become exposed. Exposure of the underlying vessel wall increases inflammation, the growth of smooth muscle cells, and the deposition of cholesterol. As a result, the vessel narrows and becomes scarred and irregular, which contributes to even more stress on the vessel (Cooper, Cooke and Dzau, J Gerontol Biol Sci 49: 191-6, 1994). Aging endothelial cells also produce altered amounts of trophic factors (hormones that affect the activity of neighboring cells). These too contribute to increased clotting, proliferation of smooth muscle cells, invasion by white blood cells, accumulation of cholesterol, and other changes, many of which lead to plaque formation and clinical cardiovascular disease (Ibid.). By extending endothelial cell telomeres, the subject methods can be employed to combat the stresses contributing to vessel disease. Many heart attacks may be prevented if endothelial cells were enabled to continue to divide normally and better maintain cardiac vessels. The occurrence of strokes caused by the aging of brain blood vessels may also be significantly reduced by employing the subject methods to help endothelial cells in the brain blood vessels to continue to divide and perform their intended function.

The subject methods also find use in skin rejuvenation. The skin is the first line of defense of the immune system and shows the most visible signs of aging (West, Arch Dermatol 130(1):87-95, 1994). As skin ages, it thins, develops wrinkles, discolors, and heals poorly. Skin cells divide quickly in response to stress and trauma; but, over time, there are fewer and fewer actively dividing skin cells. Compounding the loss of replicative capacity in aging skin is a corresponding loss of support tissues. The number of blood vessels in the skin decreases with age, reducing the nutrients that reach the skin. Also, aged immune cells less effectively fight infection. Nerve cells have fewer branches, slowing the response to pain and increasing the chance of trauma. In aged skin, there are also fewer fat cells, increasing susceptibility to cold and temperature changes. Old skin cells respond more slowly and less accurately to external signals. They produce less vitamin D, collagen, and elastin, allowing the extracellular matrix to deteriorate. As skin thins and loses pigment with age, more ultraviolet light penetrates and damages skin. To repair the increasing ultraviolet damage, skin cells need to divide to replace damaged cells, but aged skin cells have shorter telomeres and are less capable of dividing (Fossel, REVERSING HUMAN AGING. William Morrow & Company, New York City, 1996).

By practicing the subject methods, e.g., via administration of an active agent topically, one can extend telomere length, and slow the downward spiral that skin experiences with age. Such a product not only helps protect a person against the impairments of aging skin; it also permits rejuvenated skin cells to restore youthful immune resistance and appearance. The subject methods can be used for both medical and cosmetic skin rejuvenation applications.

Yet another disease condition in which the subject methods find use in the treatment of osteoporosis. Two types of cells interplay in osteoporosis: osteoblasts make bone and osteoclasts destroy it. Normally, the two are in balance and maintain a constant turnover of highly structured bone. In youth, bones are resilient, harder to break, and heal quickly. In old age, bones are brittle, break easily, and heal slowly and often improperly. Bone loss has been postulated to occur because aged osteoblasts, having lost much of their replicative capacity, cannot continue to divide at the rate necessary to maintain balance (Hazzard et al. PRINCIPLES OF GERIATRIC MEDICINE AND GERONTOLOGY, 2d ed. McGraw-Hill, New York City, 1994). The subject methods can be employed to lengthen telomeres of osteoblast and osteoclast stem cells, thereby encouraging bone replacement and proper remodeling and reinforcement. The resultant stronger bone improves the quality of life for the many sufferers of osteoporosis and provides savings from fewer fracture treatments. The subject methods are generally part of a comprehensive treatment regime that also includes calcium, estrogen, and exercise.

Additional disease conditions in which the subject methods find use are described in WO 99/35243, the disclosures of which are herein incorporated by reference.

In addition to the above described methods, the subject methods can also be used to extend the lifetime of a mammal. By extend the lifetime is meant to increase the time during which the animal is alive, where the increase is generally at least 1%, usually at least 5% and more usually at least about 10%, as compared to a control.

As indicated above, instead of a multicellular animal, the target may be a cell or population of cells which are treated according to the subject methods and then introduced into a multicellular organism for therapeutic effect. For example, the subject methods may be employed in bone marrow transplants for the treatment of cancer and skin grafts for burn victims. In these cases, cells are isolated from a human donor and then cultured for transplantation back into human recipients. During the cell culturing, the cells normally age and senesce, decreasing their useful lifespans. Bone marrow cells, for instance, lose approximately 40% of their replicative capacity during culturing. This problem is aggravated when the cells are first genetically engineered (Decary, Mouly et al. Hum Gene Ther 7(11): 1347-50, 1996). In such cases, the therapeutic cells must be expanded from a single engineered cell. By the time there are sufficient cells for transplantation, the cells have undergone the equivalent of 50 years of aging (Decary, Mouly et al. Hum Gene Ther 8(12): 1429-38, 1997). Use of the subject methods spares the replicative capacity of bone marrow cells and skin cells during culturing and expansion and thus significantly improves the survival and effectiveness of bone marrow and skin cell transplants. Any transplantation technology requiring cell culturing can benefit from the subject methods, including ex vivo gene therapy applications in which cells are cultured outside of the animal and then administered to the animal, as described in U.S. Pat. Nos. 6,068,837; 6,027,488; 5,824,655; 5,821,235; 5,770,580; 5,756,283; 5,665,350; the disclosures of which are herein incorporated by reference.

Treatment of Disease Conditions by Decreasing TERT Expression

As summarized above, also provided are methods for enhancing repression of TERT expression, where by enhancement of TERT expression repression is meant a decrease in TERT expression by a factor of at least about 2 fold, usually at least about 5 fold and more usually at least about 10 fold, as compared to a control. Methods for enhancing repressor protein mediated TERT expression repression find use in, among other applications, the treatment of cellular proliferative disease conditions, including neoplastic disease conditions, i.e., cancer. In such applications, an effective amount of an active agent, e.g., a repressor protein, analog or mimetic thereof, a vector encoding a repressor protein or active fragment thereof, an agent that enhances endogenous repressor protein activity, an agent that enhances expression of a repressor protein, etc., is administered to the subject in need thereof. Treatment is used broadly as defined above, e.g., to include at least an amelioration in one or more of the symptoms of the disease, as well as a complete cessation thereof, as well as a reversal and/or complete removal of the disease condition, e.g., cure. Methods of treating disease conditions resulting from unwanted TERT expression, such as cancer and other diseases characterized by the presence of unwanted cellular proliferation, are described in, for example, U.S. Pat. Nos. 5,645,986; 5,656,638; 5,703,116; 5,760,062; 5,767,278; 5,770,613; and 5,863,936; the disclosures of which are herein incorporated by reference.

Screening Assays

Also provided by the subject invention are screening protocols and assays for identifying agents that modulate, e.g., inhibit or enhance, repressor protein repression of TERT transcription. As such, the screening assays are assays that provide for the identification of agents that modulate, e.g., inhibit or enhance, the binding interaction between a repressor protein and Site C.

The screening methods will typically be assays which provide for qualitative/quantitative measurements of TERT promoter controlled expression, e.g., of a coding sequence for a marker or reporter gene, in the presence of a particular candidate therapeutic agent. For example, the assay could be an assay which measures the TERT promoter controlled expression of a reporter gene (i.e. coding sequence, e.g., luciferase, SEAP, etc.) in the presence and absence of a candidate inhibitor agent, e.g. the expression of the reporter gene in the presence or absence of a candidate agent. The screening method may be an in vitro or in vivo format, where both formats are readily developed by those of skill in the art. In other words, such assays can be done in vivo or in vitro in mammalian, non-mammalian, Yeast, bacteria, etc.

In Vitro Models of Repressor Protein Function

In vitro models of repressor protein function are provided. Of particular interest are models of repressor protein TERT binding events in which the TERT binding site is Site C. Such models typically include: a Site C site, a repressor protein polypeptide and a modulatory agent, e.g., competitor or inhibitor, which are present under conditions sufficient to inhibit repressor protein/site C binding. The competitor may be any compound that is, or is suspected to be, a compound capable of specifically binding to the repressor protein, where of particular interest in many embodiments is the use of the subject ligands described above as competitors. Depending on the particular model, one or more of, usually one of, the specified components may be labeled, where by labeled is meant that the components comprise a detectable moiety, e.g. a fluorescent or radioactive tag, or a member of a signal producing system, e.g. biotin for binding to an enzyme-streptavidin conjugate in which the enzyme is capable of converting a substrate to a chromogenic product.

The above in vitro models may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times, e.g. soluble repressor protein and a competitor ligand may be combined first, and the resultant mixture subsequently combined with bound site C sequence. Following the contact step, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the presence of bound repressor protein/Site C complexes will then be detected.

In alternative in vitro models, an expression cassette including a reporter gene under control of a Site C sequence and repressor protein may be present in a cell free environment in which the reporter gene is expressed in the absence of repressor protein binding to the Site C region. By expression cassette or system is meant a nucleic acid that includes a sequence encoding a peptide or protein of interest, i.e., a coding sequence, operably linked to a promoter sequence, where by operably linked is meant that expression of the coding sequence is under the control of the promoter sequence. The expression systems and cassettes of the subject invention include a Site C repressor binding site/region operably linked to the promoter, where the promoter is, in many embodiments, a TERT promoter, such as the hTERT promoter. See e.g., the hTERT promoter sequence described in Cong et al., Hum. Mol. Genet. (1999) 8:137-142. The in vitro model further includes a coding sequence of interest operably linked to the Site C binding site. The expression system is then employed in an appropriate cell free environment that includes the repressor protein to provide expression or non-expression of the protein, as desired.

In Vivo Models of Repressor Protein Function

A variety of different in vivo models of repressor protein function are also provided by the subject invention and may be used in the screening assays of the subject invention. In vivo models of interest include engineered cells that include an expression cassette as described above and a repressor protein, which components are present in a host cell. Also of interest in the subject screening assays are multicellular in vivo models, e.g., the transgenic animal models described below.

Whether the format is in vivo or in vitro, the model being employed is combined with the candidate agent and the effect of the candidate agent on model is observed and related to the TERT expression modulatory activity of the agent. For example, for screening inhibitory agents, the model is combined with the candidate agent in an environment in which, in the absence of the candidate agent, the TERT promoter is repressed, e.g., in the presence of a repressor protein, that interacts with the TERT Site C repressor binding site and causes TERT promoter repression. The conditions may be set up in vitro by combining the various required components in an aqueous medium, or the assay may be carried out in vivo, etc.

Alternatively, the repressor protein could be engineered to replace the repressor domain with an activation domain (or other detectable domain), but still retaining the DNA binding domain. In this manner, assays can be set up in which agents that are candidates for preventing the repressor protein DNA binding domain from binding to the DNA binding site can be screened (as described in the above paragraph) for activation (or other signal) of the reporter gene instead of repression. Likewise, the repressor protein could be engineered to replace the DNA binding domain with another DNA binding domain (e.g. p53), but still retaining the repression domain. In this manner, assays can be set up in which agents that are candidates for preventing the repression domain from binding to cofactors (protein-protein interaction) can be screened using DNA binding domains that have already been well characterized. In this manner, agents that enhance and inhibit protein-protein interactions with cofactors involved in TERT expression repression may be identified.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents identified in the above screening assays that inhibit repression of TERT transcription find use in the methods described above, e.g., in the enhancement of TERT expression. Alternatively, agents identified in the above screening assays that enhance repression find use in applications where inhibition of TERT expression is desired, e.g., in the treatment of disease conditions characterized by the presence of unwanted TERT expression, such as cancer and other diseases characterized by the presence of unwanted cellular proliferation, where such methods are described in, for example, U.S. Pat. Nos. 5,645,986; 5,656,638; 5,703,116; 5,760,062; 5,767,278; 5,770,613; and 5,863,936; the disclosures of which are herein incorporated by reference.

Generation of Antibodies

In one embodiment of the invention, the blocking of the repressor protein mediated TERT repression is used to immortalize cells in culture. Exemplary of cells that may be used for this purpose are non-transformed antibody producing cells, e.g. B cells and plasma cells which may be isolated and identified for their ability to produce a desired antibody using known technology as, for example, taught in U.S. Pat. No. 5,627,052. These cells may either secrete antibodies (antibody-secreting cells) or maintain antibodies on the surface of the cell without secretion into the cellular environment. Such cells have a limited lifespan in culture, and are usefully immortalized by upregulating expression of telomerase using the methods of the present invention.

Because the above described methods are methods of increasing expression of TERT and therefore increasing the proliferative capacity and/or delaying the onset of senescence in a cell, they find applications in the production of a range of reagents, typically cellular or animal reagents. For example, the subject methods may be employed to increase proliferation, delay senescence and/or extend the lifetimes of cultured cells. Cultured cell populations having enhanced TERT expression are produced using any of the protocols as described above, including by contact with an agent that inhibits repressor region transcription repression and/or modification of the repressor region in a manner such that it no longer represses TERT coding sequence transcription, etc.

The subject methods find use in the generation of monoclonal antibodies. An antibody-forming cell may be identified among antibody-forming cells obtained from an animal which has either been immunized with a selected substance, or which has developed an immune response to an antigen as a result of disease. Animals may be immunized with a selected antigen using any of the techniques well known in the art suitable for generating an immune response. Antigens may include any substance to which an antibody may be made, including, among others, proteins, carbohydrates, inorganic or organic molecules, and transition state analogs that resemble intermediates in an enzymatic process. Suitable antigens include, among others, biologically active proteins, hormones, cytokines, and their cell surface receptors, bacterial or parasitic cell membrane or purified components thereof, and vital antigens.

As will be appreciated by one of ordinary skill in the art, antigens which are of low immunogenicity may be accompanied with an adjuvant or hapten in order to increase the immune response (for example, complete or incomplete Freund's adjuvant) or with a carrier such as keyhole limpet hemocyanin (KLH).

Procedures for immunizing animals are well known in the art. Briefly, animals are injected with the selected antigen against which it is desired to raise antibodies. The selected antigen may be accompanied by an adjuvant or hapten, as discussed above, in order to further increase the immune response. Usually the substance is injected into the peritoneal cavity, beneath the skin, or into the muscles or bloodstream. The injection is repeated at varying intervals and the immune response is usually monitored by detecting antibodies in the serum using an appropriate assay that detects the properties of the desired antibody. Large numbers of antibody-forming cells can be found in the spleen and lymph node of the immunized animal. Thus, once an immune response has been generated, the animal is sacrificed, the spleen and lymph nodes are removed, and a single cell suspension is prepared using techniques well known in the art.

Antibody-forming cells may also be obtained from a subject which has generated the cells during the course of a selected disease. For instance, antibody-forming cells from a human with a disease of unknown cause, such as rheumatoid arthritis, may be obtained and used in an effort to identify antibodies which have an effect on the disease process or which may lead to identification of an etiological agent or body component that is involved in the cause of the disease. Similarly, antibody-forming cells may be obtained from subjects with disease due to known etiological agents such as malaria or AIDS. These antibody forming cells may be derived from the blood or lymph nodes, as well as from other diseased or normal tissues. Antibody-forming cells may be prepared from blood collected with an anticoagulant such as heparin or EDTA. The antibody-forming cells may be further separated from erythrocytes and polymorphs using standard procedures such as centrifugation with Ficoll-Hypaque (Pharmacia, Uppsula, Sweden). Antibody-forming cells may also be prepared from solid tissues such as lymph nodes or tumors by dissociation with enzymes such as collagenase and trypsin in the presence of EDTA.

Antibody-forming cells may also be obtained by culture techniques such as in vitro immunization. Briefly, a source of antibody-forming cells, such as a suspension of spleen or lymph node cells, or peripheral blood mononuclear cells are cultured in medium such as RPMI 1640 with 10% fetal bovine serum and a source of the substance against which it is desired to develop antibodies. This medium may be additionally supplemented with amounts of substances known to enhance antibody-forming cell activation and proliferation such as lipopolysaccharide or its derivatives or other bacterial adjuvants or cytokines such as IL-1, IL-2, IL-4, IL-5, IL-6, GM-CSF, and IFN-γ. To enhance immunogenicity, the selected antigen may be coupled to the surface of cells, for example, spleen cells, by conventional techniques such as the use of biotin/avidin as described below.

Antibody-forming cells may also be obtained from very early monoclonal or oligoclonal fusion cultures produced by conventional hybridoma technology. The present invention is advantageous in that it allows rapid selection of antibody-forming cells from unstable, interspecies hybridomas, e.g., formed by fusing antibody-forming cells from animals such as rabbits, humans, cows, pigs, cats, and dogs with a murine myeloma such NS-1.

Antibody-forming cells may be enriched by methods based upon the size or density of the antibody-forming cells relative to other cells. Gradients of varying density of solutions of bovine serum albumin can also be used to separate cells according to density. The fraction that is most enriched for desired antibody-forming cells can be determined in a preliminary procedure using the appropriate indicator system in order to establish the antibody-forming cells.

The identification and culture of antibody producing cells of interest is followed by enhancement of TERT expression is these cells by the subject methods, thereby avoiding the need for the immortalization/fusing step employed in traditional hybridoma manufacture protocols. In such methods, the first step is immunization of the host animal with an immunogen, typically a polypeptide, where the polypeptide will preferably be in substantially pure form, comprising less than about 1% contaminant. The immunogen may comprise the complete protein, fragments or derivatives thereof. To increase the immune response of the host animal, the protein may be combined with an adjuvant, where suitable adjuvants include alum, dextran, sulfate, large polymeric anions, oil & water emulsions, e.g. Freund's adjuvant, Freund's complete adjuvant, and the like. The protein may also be conjugated to synthetic carrier proteins or synthetic antigens. A variety of hosts may be immunized to produce the subject antibodies. Such hosts include rabbits, guinea pigs, rodents (e.g. mice, rats), sheep, goats, and the like. The protein is administered to the host, usually intradermally, with an initial dosage followed by one or more, usually at least two, additional booster dosages. Following immunization, generally, the spleen and/or lymph nodes of an immunized host animal provide a source of plasma cells. The plasma cells are treated according to the subject invention to enhance TERT expression and thereby, increase the proliferative capacity and/or delay senescence to produce "pseudo" immortalized cells. Culture supernatant from individual cells is then screened using standard techniques to identify those producing antibodies with the desired specificity. Suitable animals for production of monoclonal antibodies to a human protein include mouse, rat, hamster, etc. To raise antibodies against the mouse protein, the animal will generally be a hamster, guinea pig, rabbit, etc. The antibody may be purified from the cell supernatants or ascites fluid by conventional techniques, e.g. affinity chromatography using RFLAT-1 protein bound to an insoluble support, protein A sepharose, etc.

In an analogous fashion, the subject methods are employed to enhance TERT expression in non-human animals, e.g., non-human animals employed in laboratory research. Using the subject methods with such animals can provide a number of advantages, including extending the lifetime of difficult and/or expensive to produce transgenic animals. As with the above described cells and cultures thereof, the expression of TERT in the target animals may be enhanced using a number of different protocols, including the administration of an agent that inhibits SC repression and/or targeted disruption of the repressor binding site. The subject methods may be used with a number of different types of animals, where animals of particular interest include mammals, e.g., rodents such as mice and rats, cats, dogs, sheep, rabbits, pigs, cows, horses, and non-human primates, e.g. monkeys, baboons, etc.

Additional Utilities

The subject polypeptide and nucleic acid compositions find use in a variety of additional applications. Applications in which the subject polypeptide and nucleic acid compositions find use include: (a) the identification of homologs; (b) as a source of novel promoter elements; (c) the identification of expression regulatory factors; (d) as probes and primers in hybridization applications, e.g. PCR; (e) the identification of expression patterns in biological specimens; (f) the preparation of cell or animal models for function; (g) the preparation of in vitro models for function; (h) the identification of binding proteins; (i) the identification of binding DNA's (e.g. other promoters); etc.

Identification of Homologs

Homologs are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/ 0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Nucleic acids having a region of substantial identity to the provided sequences, e.g. allelic variants, genetically altered versions of the gene, etc., bind to the provided sequences under stringent hybridization conditions. By using probes, particularly labeled probes of DNA sequences, one can isolate homologous or related genes.

Identification of Novel Promoter Elements

The sequence of the 5' flanking region may be utilized for promoter elements, including enhancer binding sites, that provide for regulation in tissues where the repressor protein is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Identification of Expression Regulatory Factors

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995), *Mol. Med.* 1:194-205; Mortlock et al. (1996), *Genome Res.* 6:327-33; and Joulin and Richard-Foy (1995), *Eur. J. Biochem.* 232:620-626.

The regulatory sequences may be used to identify cis acting sequences required for transcriptional or translational regulation of gene expression, especially in different tissues or stages of development, and to identify cis acting sequences and trans-acting factors that regulate or mediate gene expression. Such transcription or translational control regions may be operably linked to a repressor protein gene in order to promote expression of wild type or altered or other proteins of interest in cultured cells, or in embryonic, fetal or adult tissues, and for gene therapy.

Probes and Primers

Small DNA fragments are useful as primers for PCR, hybridization screening probes, etc. Larger DNA fragments, i.e. greater than 100 nt are useful for production of the encoded polypeptide, as described in the previous section. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

Identification of Expression Patterns in Biological Specimens

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of gene expression in the sample.

The Preparation of Mutants

The sequence of a gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993), *Biotechniques* 14:22; Barany (1985), *Gene* 37:111-23; Colicelli et al. (1985), *Mol. Gen. Genet*, 199:537-9; and Prentki et al. (1984), *Gene* 29:303-13. Methods for site specific mutagenesis can be found in Sambrook et al., *Molecular Cloning: A Laboratory Manual*, CSH Press 1989, pp. 15.3-15.108; Weiner et al. (1993), *Gene* 126:35-41; Sayers et al. (1992), *Biotechniques* 13:592-6; Jones and Winistorfer (1992), *Biotechniques* 12:528-30; Barton et al. (1990), *Nucleic Acids Res* 18:7349-55; Marotti and Tomich (1989), *Gene Anal. Tech.* 6:67-70; and Zhu (1989), *Anal Biochem* 177:120-4. Such mutated genes may be used to study structure-function relationships, or to alter properties of the protein that affect its function or regulation.

Production of In Vivo Models of Repressor Protein Function

The subject nucleic acids can be used to generate transgenic, non-human animals or site specific gene modifications in cell lines. Transgenic animals may be made through homologous recombination, where the normal locus is altered. Alternatively, a nucleic acid construct is randomly integrated into the genome. Vectors for stable integration include plasmids, retroviruses and other animal viruses, YACs, and the like.

The modified cells or animals are useful in the study of repressor function and regulation. For example, a series of small deletions and/or substitutions may be made in the host's native gene to determine the role of different exons in the regulation of telomerase expression, e.g. repression of TERT promoter. Specific constructs of interest include anti-sense, which will block expression, expression of dominant negative mutations, and over-expression of repressor protein genes. Where a sequence is introduced, the introduced sequence may be either a complete or partial sequence of a gene native to the host, or may be a complete or partial sequence that is exogenous to the host animal, e.g., a human sequence. A detectable marker, such as lac Z, may be introduced into the locus, where upregulation of expression will result in an easily detected change in phenotype.

One may also provide for expression of the gene or variants thereof in cells or tissues where it is not normally expressed (e.g., Mammalian, non-Mammalian, Yeast, Bacterial, etc. cells), at levels not normally present in such cells or tissues, or at abnormal times of development. DNA constructs for homologous recombination will comprise at least a portion of the gene native to the species of the host animal, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527-537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on repressor protein activity.

Production of In Vitro Models of Repressor Protein Function

Also provided by the subject invention are in vitro models of repressor protein function, e.g. the role of the repressor protein as a TERT repressor. Of particular interest is the modulation of repressor protein TERT binding events in which the TERT binding site is site C. In in vitro methods of inhibiting TERT repressor binding events, such methods typically include a competitor or inhibitor under conditions sufficient to inhibit Site C binding to occur. The competitor may be any compound that is, or is suspected to be, a compound capable of specifically binding to a repressor protein, where of particular interest in many embodiments is the use of the subject ligands described above as competitors. Depending on the particular method, one or more of, usually one of, the specified components may be labeled, where by labeled is meant that the components comprise a detectable moiety, e.g. a fluorescent or radioactive tag, or a member of a signal producing system, e.g. biotin for binding to an enzyme-streptavidin conjugate in which the enzyme is capable of converting a substrate to a chromogenic product.

The above in vitro methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times, e.g. soluble repressor protein and a competitor ligand may be combined first, and the resultant mixture subsequently combined with bound Site C sequence. Following the contact step, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the presence of bound Site C complexes will then be detected.

The above-described in vitro methods find use in screening assays designed to identify the presence or absence of repressor protein in cancerous cells. The above described in vitro methods also find use in screening assays designed to identify compounds that inhibit the binding of repressor protein to the TERT promoter.

Diagnostic Applications

Also provided are methods of diagnosing disease states associated with repressor protein activity or the absence thereof, e.g., based on observed levels of repressor protein or the expression level of the gene in a biological sample of interest. Samples, as used herein, include biological fluids such as blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

A number of methods are available for determining the expression level of a gene or protein in a particular sample. Diagnosis may be performed by a number of methods to determine the absence or presence or altered amounts of normal or abnormal repressor protein in a patient sample. For example, detection may utilize staining of cells or histological sections with labeled antibodies, performed in accordance with conventional methods. Cells are permeabilized to stain intracellular molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Alternatively, one may focus on the expression of the repressor protein. Biochemical studies may be performed to determine whether a sequence polymorphism in an coding region or control regions is associated with disease. Disease associated polymorphisms may include deletion or truncation of the gene, mutations that alter expression level, that affect the activity of the protein, etc.

Changes in the promoter or enhancer sequence that may affect expression levels of repressor protein can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express repressor protein may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp. 14.2-14.33. Alternatively, various methods are known in the art that utilize oligonucleotide ligation as a means of detecting polymorphisms, for examples see Riley et al. (1990), *Nucl. Acids Res.* 18:2887-2890; and Delahunty et al. (1996), *Am. J. Hum. Genet.* 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations may be based on the functional or antigenic characteristics of the protein. Protein truncation assays are useful in detecting deletions that may affect the biological activity of the protein. Various immunoassays designed to detect polymorphisms in proteins may be used in screening. Where many diverse genetic mutations lead to a particular disease phenotype, functional protein assays have proven to be effective screening tools. The activity, e.g. TERT repressor functionality, of the encoded protein may be determined by comparison with the wild-type protein.

Diagnostic methods of the subject invention in which the level of expression is of interest will typically involve comparison of the nucleic acid abundance of a sample of interest with that of a control value to determine any relative differences, where the difference may be measured qualitatively and/or quantitatively, which differences are then related to the presence or absence of an abnormal expression pattern. A variety of different methods for determining the nucleic acid abundance in a sample are known to those of skill in the art, where particular methods of interest include those described in: Pietu et al., Genome Res. (June 1996) 6: 492-503; Zhao et al., Gene (Apr. 24, 1995) 156: 207-213; Soares, Curr. Opin. Biotechnol. (October 1997) 8: 542-546; Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

The following examples are offered by way of illustration and not by way of limitation.

EXPERIMENTAL

I. Deletion Experiments 118 deletions of the minimal telomerase promoter (as defined by Takahura et al., Cancer Res. (1999) 59:551-7) were constructed to find regions within the telomerase promoter that contain potential repressor sites. These deletions ranged in size from 10 to 300 bases. Each deletion version of the minimal promoter was tested for its ability to express SEAP in MRC5 and HELA cells. Several of the deletions, all mapping about 50-100 bases upstream of the telomerase translation initiation codon (ATG), showed ~10 fold increased expression. The highest expression in MRC5 was obtained with the deletion called 11K. This 30 base deletion includes bases −48 to −77 relative to the translation initiation codon ATG. However, a similar deletion, called 12K, that includes bases −48 to −57 results in 500 fold less expression. On the other hand, when 11K and 12K were compared in HELA, they both gave equivalent amounts of expression. The repressor site in this region of the TERT minimal promoter therefore is contained, or overlaps with, the 20 bases present in 12K and absent in 11K (i.e. −58 to −77).

To identify more specifically the bases that make up this repressor site, additional deletions were made. Each deletion is 10 bases long with 7 to 8 base overlaps between consecutive deletions. The deletions were made in the minimal telomerase promoter in pSS120. Each deletion mutant was independently made three times and all deletions were transiently transfected into MRC5 (telomerase negative normal cells) and HELA (telomerase positive immortal cells).

A portion of the 5' untranslated region is shown below, from −77 to 1, the start of translation (SEQ ID No:2). The Site C repressor site extends from −69 to −58, as shown.

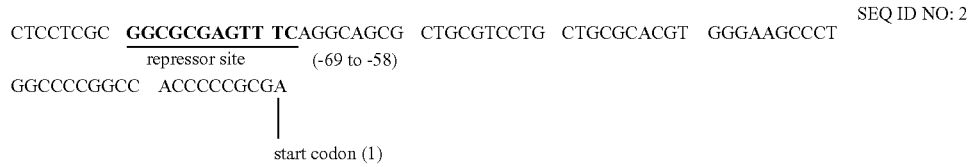

The repressor site is provided separately below as SEQ ID NO. 1.

```
        GGCGCGAGTTTC          SEQ ID NO: 1
```

The expression levels were measured using the Secreted Alkaline Phosphatase Assay (SEAP) system commercially available from Clontech Laboratories, Inc. (Palo Alto, Calif.). The results are shown below.

| Deletion | MRC5 | HELA |
|---|---|---|
| NONE (control) | 0.1931 | 78.3076 |
| −104 to −95 | 0.19 | 78.30 |
| −102 to −93 | 4.92 | 73.97 |
| −99 to −90 | 1.19 | 86.95 |
| −97 to −88 | 1.69 | 97.94 |
| −94 to −85 | 8.06 | 89.6 |
| −92 to −83 | 7.89 | 89.86 |
| −89 to −80 | 12.00 | 93.91 |
| −87 to −78 | 7.26 | 59.74 |
| −84 to −75 | 7.77 | 85.48 |
| −82 to −73 | 4.83 | 99.4 |
| −79 to −70 | 3.79 | 73.34 |
| −77 to −68 | 17.15 | 82.26 |
| −74 to −65 | 34.44 | 78.99 |
| −72 to −63 | 33.22 | 123.8 |
| −69 to −60 | 33.15 | 133.56 |
| −67 to −58 | 56.98 | 97.74 |

-continued

| Deletion | MRC5 | HELA |
|---|---|---|
| −64 to −55 | 21.82 | 127.32 |
| −62 to −53 | 4.60 | 108 |
| −59 to −50 | 19.58 | 103.1 |

The column of deletions indicates the bases that were deleted in the repressor site, which is indicated relative to the AUG start codon. The columns for MRC5 and HELA show the level of expression observed for each deletion, reported as a percentage of the SV40 early promoter, which was used to normalize the two cell lines.

The data demonstrate that the deletion from "−67 to −58" gave a reading of 56.9852, as compared to a reading of 0.193109 in the control cells with no deletion in the promoter, giving an increase of 295 fold higher expression. This same deletion gave only 97.746 in HELA cells, compared to the undeleted control value of 78.3076, resulting in a 1.25 fold higher expression. This finding indicates that a repressor function operates in MRC5 cells to repress expression of the wild type telomerase promoter. When the expression level of deletion "−67 to −58" in MRC5 is compared to the wild type promoter in HELA it is observed that the deletion resulted in almost as much expression as the levels observed in HELA that are sufficient to maintain telomere length. That is, the expression of the deletion in MRC5 was 59.9852/78.3076=77% of the wild type in HELA. This finding indicates that depressing the repressor in MRC5 allows for sufficient amounts of telomerase expression to maintain the length of the telomeres in the cells during cell division, and to stop cellular aging in these cells.

II. Identification of Site C Binding Protein in U937 Cells

U937 cells are telomerase positive. However, treatment with the drug TPA causes them to become telomerase negative. Gel shift assays were performed using the Site C oligo and nuclear extracts from either non-treated or TPA treated U937 cells. The extract from the TPA treated U937 cells was observed to contain much more of the protein that binds Site C than the extract from the untreated cells. This finding is consistent with the mechanism that TPA treated U937 cells express more of the repressor protein that turns off the telomerase promoter and, resulting in these cells being telomerase negative.

III. One-Hybrid Screening Assay

The following experiments utilized the one-hybrid-assay system (purchased from Clontech Laboratories, Inc., Palo Alto, Calif.) to identify repressor factors that bind to the Site C sequence of the TERT promoter.

For the one hybrid assays utilized in the present invention, constructs were prepared with multiple tandem copies of the Site C bait element and then inserted upstream of a reporter gene in an appropriate vector (GAL4 AD vector). The reporter construct was subsequently integrated into the yeast genome to create a new yeast reporter strain. The yeast strain was transformed with an activation domain (AD) fusion library to screen for proteins containing DNA-binding domains (DNA-BD) that interact with the bait DNA sequence. Binding of an AD/DNA-BD hybrid protein to the bait sequence results in activation of the reporter gene transcription.

To screen a library for a cDNA encoding a binding protein that interacts with the bait sequence (Site C binding site), the modified yeast reporter strain was transformed with an activation domain (AD) fusion library, and then the transformants were plated on selective medium. If an AD fusion protein interacted with the bait DNA sequence, the HIS3 reporter gene was expressed, allowing colony growth on minimal medium lacking histidine. A HIS3, lacZ double reporter strain was used, allowing a β-galactosidase assay to be performed to confirm AD protein interaction with the bait element to eliminate false positives. Compatible cDNA libraries for the one hybrid assay system were purchased from Clontech Laboratories Inc. (Palo Alto, Calif.).

The Site C bait was designed to minimize the possibility of known yeast transcription factors binding to the bait element. For this reason, only a partial sequence of Site C was used as the bait element. Five tandem repeats of Site C were used to further increase the mimicking of the positive p53 bait controls.

The following partial sequence of Site C was used as bait, GGCGCGAGTTT (SEQ ID NO:3). The bases AG were inserted between each site C repeat. These changes in the bait sequence were made to minimize the similarity of this sequence to the consensus sequences of known yeast transcription factors. This modified bait sequence was tested in a transient transfection expression assay using human lung fibroblast cells (MRC5) to show that the Site C repressor factor(s) still bound to this shortened Site C. This shortened Site C was observed to cause significant repression in MRC5, but not as much as the complete Site C (SEQ ID NO: 1).

The Bait was made as a double-stranded oligonucleotide and was cloned into the EcoR1-XHO1 sites of pHisi, pHisi-1, and p53Blue. FIG. 1 shows a Site C bait fragment used in the one hybrid assays which contains five tandem repeats of an 11 base telomerase promoter fragment that includes 11 out of 12 bases of Site C.

Three different libraries were screened using the Site C bait sequence. The libraries were: human lung, human liver and human placenta (all purchased from Clontech Laboratories Inc., Palo Alto, Calif.). Each library was transformed into yeast reporter strains (containing the Site C bait sequences) and plated onto SD/-His/-Leu agar plates supplemented with 30 mM 3-amino-1,2,4-triazole media, as described by the vendor. The libraries were each plated at a density of ~60,000 colonies per 150×15 mm plate. The lung library was plated on 50 plates ($3×10^6$ total colonies) and the liver and placenta libraries were each plated on 300 plates ($1.8×10^7$ total colonies each).

Approximately 150 large colonies were observed to grow on the plates after 5-6 days incubation at 30° C. Thirty of these colonies were observed on the plates containing the lung library while the plates containing the liver and placenta libraries each produced 60 large colonies. All large colonies were picked and tested for β-galactosidase activity. Three colonies from the lung library, 13 colonies from the placenta library, and 25 colonies from the liver library tested positive for β-galactosidase activity.

These 41 colonies were grown in culture and plasmid DNA was isolated from each one. The plasmid DNAs were then transformed into E. coli DH5alpha, and the bacterial colonies were miniscreened with EcoR1 and XHO1. The miniscreens showed that the plasmids were not random isolates. Several of the plasmids had similar DNA restriction fragment patterns and were grouped accordingly into families. Sixteen families of plasmids were observed. The presence of "families" shows that the one-hybrid screen selected for specific cDNAs in the libraries.

IV. Backscreening of Positive Clones

Further verification that the clones bind to site C and not to the junctures was determined by backscreening experiments. Each family was tested for its ability to bind Site C as opposed to the junctures between Site Cs.

To test each family for their ability to bind Site C, as opposed to the junctures between Site C's, additional bait sequences were constructed in which the junctures between the Site C's were changed in sequence and in length.

The junctures of the bait sequences present in SEQ ID NO:04, and 05 are indicated in bold type.

```
Original Bait                                              SEQ ID NO: 04
(SEQ ID NO: 03 sequence repeated with AG junctions).
AATTCGGCGCGAGTTTAG GGCGCGAGTTTAG GGCGCGAGTTTAGGGCGCGAGTTTAG GGCGCGAGTTTAG T Bait #2                                                    SEQ ID NO: 05
AATTCGGCGCGAGTTTCCTGGCGCGAGTTTCCTGGCGCGAGTTTCCTGGCGCGAGTTTCCTGGCGCGAGTTTCCTT
       ***********   ***********   ***********   ***********   ***********
          Site C        Site C        Site C        Site C        Site C
```

Note: The first C in the junctures of SEQ ID NO:05 is actually part of the Site C sequence, but it is shown here in bold to indicate that it is a base that was not included in SEQ ID NO:04.

Plasmids from each family, plus a control plasmid expressing p53, were transformed into the following Yeast strains: (a) the original host strain that was used to screen the libraries and identify these plasmids; (b) a control host strain containing a bait sequence for p53 (control does not contain the Site C bait); and (c) the new host strain containing Bait #2 (SEQ ID NO:05). Clones were assayed in the original host strain to test if any of the families were artifacts. Family 13 scored the highest in the backscreening experiments. Any Families that bound to the junctures in the Original bait should not bind to Bait #2, since the junctures are different. However, any Families that bound directly to Site C should be able to bind Bait #2 since the entire Site C is still intact. When all the Families were tested in One-hybrid assays using Bait #2, Family 13 gave the best signal.

The DNA sequences identified from plasmids pSSI864, and pSSI865 (both from the placenta library) are presented as both SEQ ID NO:06 and 07. SEQ ID NO:06 is a 5' sequence of the Family 13 TERT repressor protein, while SEQ ID NO: 07 is a 3' internal sequence of the subject invention.

```
                                                           SEQ ID NO: 06
ATTTGTTGATCGATCAAGGATGGCCCCGAAGACTCCAATAAAAAATGAAC

CAATTGATTTATCGAAGCAAAAAAATTTACTCCAGAAAGAAATCCCATT

ACTCCAGTTAAGCTTGTTGACAGACAGCAAGCGGAACCATGGACACCCAC

AGCTAACCTGAAGATGCTCATTAGTGCTGCCAGCCCAGATATAAGGGACC

GGGAGAAGAAAAGGGACTATTCCGACCCATTGAAAACAAGGACGATGCA

TTTACAGATTCTCTACAGCTTGATGTTGTTGGGGACAGTGCTGTGGACGA

ATTTGAAAAGCAAAGGCCAAGCAGAAAACAGAAAAGTTTAGGACTCCTGT

GCCAGAAGTTTCTAGCTCGCTATCCAAGTTATCCCTTGTCAACTGAGAAA

ACTACCATCTCCCTAGATGAAGTTGCTGTCAGTCTTGGTGTGGAAAGGAG

ACGCATCTATGACATTGTAAATGTGCTGGAGTCGCTGCATCTGGTCAGCC

GGGTGGCTAAGAATCAGTATGGCTGGCATGG
```

```
                                                           SEQ ID NO: 07
GAATTCATAATTCCTGAGGGGTGTTAAGAAGCAGTCCCATTGGTGAGGAT

ATTATGACTTGGTGACCATTCTTAGGAGTAGAAAACCAAGGACAATTGCT

TCTGTATTCAGTATCCACTTCTTAATGTGGCTTTATATGTAAAAATAATA

ATGCAGTGGTTGTTTCTGTCAGGAAAATAAATCTTACAGAACAACTGGTG

GAATTGAAGCTGCTGCGCTAGACTTGGATATTTTGGGTAGTGAAGAAGCA
```

```
ATGGCAATCTTGAGTCTATTATTGTATAATTTAGTAAAAGAAAAAAATAA

TCGTTGGTGGTCCTACTAAGAGAATGCAGCTTTTTTGAGTTGTCACAGAG

GCTGTGTGTGCCCTACACTGACCAGGGTTTGTAAAACCCTTTCATTCTGG

TACAAGAGTCGGGGGTATAACTTTTATACTTGAATCTACCTACCAAGTTT

ACATTTCTCAATTCCTTTTTGTAAGGTGCTATTTCTGTATTTAAATAACT

TTCTTTTAACCGTAAAGCTGCTTTCTGCTTATCTTATTGCACTGCTAGTT

GTATGTAGGTATTAATTTTATTGCTGCTTACTG
```

IV. Alignment with Genbank Database ESTs

A search of the NCBI databases database identified SEQ ID NO. 6 and 7 as a novel gene. The sequences identified (SEQ ID NO:06 and 07) in plasmids pSSI864 and pSSI865 were detected in the human placenta cDNA library and encode partial sequences of this novel TERT site C repressor. No matches to SEQ ID NO:06 or NO:07 were identified in the NCBI nr database. However, when searching the NCBI est database 45 unidentified EST's were found to have homology to Family 13 (F13) sequences, SEQ ID NO:06 or NO:07, and when searching the NCBI Human Genome Database F13 was found to map to a region of Chromosome 12 (at or near Chromosome 12q15), that had previously not been characterized (beyond being sequenced). This region has the ACCESSION number of NT_009551 and has the DEFINITION of *Homo sapiens* chromosome 12 working draft sequence segment.

By identifying overlapping EST's sequences, the following F13 gene sequence was compiled (SEQ ID NO:08), which sequence was subsequently verified by sequencing:

```
   1 CTACGATCCAGGCTGGAGTTGCGCTCGGCCGGTCTGAGCGCTCGCGCTGCCCGGACGCCG   SEQ ID NO: 08
  61 CGGGGTCCCCGCCAGCCCAGGGCACTCGGCGCGGGGATCTGCGCGCCTCGCTCTCCCTTC
 121 CCGATGCCGCCGCCCGGCTGCTGATCGCCGCACCACCTTCCCTCATCGGCTTGGGTCCGT
 181 GGAGGTCCCTGCAGAGGCAGGAAGCCTCCTTAGGAAAGCAGGGATGGAGGTAAATTGTTT
 241 AACACTAAAAGACCTGATCAGCCCCAGGCAGCCCAGACTAGATTTTGCAGTTGAAGATGG
 301 GGAAAATGCACAAAAGGAAAATATATTTGTTGATCGATCAAGGATGGCCCCGAAGACTCC
 361 AATAAAAAATGAACCAATTGATTTATCGAAGCAAAAAAATTTACTCCAGAAAGAAATCC
 421 CATTACTCGAGTTAAGCTTGTTGACAGACAGCAAGCGGAACCATGGACACCCACAGCTAA
 481 CCTGAAGATGCTCATTAGTGCTGCCAGCCCAGATATAAGGGACCGGGAGAAGAAAAAGGG
 541 ACTATTCCGACCCATTGAAAACAAGGACGATGCATTTACGATTCTCTACAGCTTGATGT
 601 TGTTGGGGACAGTGCTGTGGACGAATTTGAAAAGCAAAGGCCAAGCAGAAAACAGAAAAG
 661 TTTAGGACTCCTGTGCCAGAAGTTTCTAGCTCGCTATCCAAGTTATCCCTTGTCAACTGA
 721 GAAAACTACCATCTCCCTAGATGAAGTTGCTGTCAGTCTTGGTGTGGAAAGGAGACGCAT
 781 CTATGACATTGTAAATGTGCTGGAGTCGCTGCATCTGGTCAGCCGGGTGGCTAAGAATCA
 841 GTATGGCTGGCATGGACGGCACAGCCTGCCAAAAACCCTGAGGAACCTCCAGAGACTAGG
 901 AGAGGAGCAGAAATATGAAGAGCAAATGGCCTACCTCCAACAGAAAGAGCTGGACCTGAT
 961 AGATTATAAATTTGGAGAACGTAAAAAAGATGGTGATCCAGATTCCCAGGAACAACAGTT
1021 ACTGGATTTCTCTGAACCCGACTGTCCCTCTTCATCTGCAAACAGTAGAAAAGACAAGTC
1081 TCTGAGAATTATGAGCCAGAAGTTTGTCATGCTGTTCCTCGTCTCCAAAACCAAGATTGT
1141 CACTCTGGATGTGGCTGCCAAAATACTGATAGAAGAAAGCCAAGATGCCCCAGACCATAG
1201 TAAATTTAAAACAAAGGTACGACGCCTCTATGACATAGCCAATGTTCTGACCAGCTTGGC
1261 TCTGATAAAGAAAGTGCATGTAACAGAAGAGCGAGGTCGTAAACCAGCCTTCAAGTGGAT
1321 CGGGCCTGTGACTTCAGCTCAAGTGATGAAGAACTGGTGGATGTTTCTGCATCTGTCTT
1381 ACCAGAATTGAAAAGAGAAACATATGGCCAGATTCAAGTCTGTGCAAAACAGAAGCTGGC
1441 TCGCCATGGTTCTTTTAACACAGTTCAGGCTTCTGAGAGGATCCAGAGGAAAGTGAACTC
1501 AGAACCGAGCAGCCCGTACAGAGAAGAACAAGGATCAGGTGGCTACTCTTTAGAAATTGG
1561 AAGCCTGGCAGCTGTCTATAGACAGAAAATAGAAGACAATTCACAGGGAAAAGCCTTTGC
1621 CAGTAAGAGAGTGGTGCCTCCATCAAGCAGCTTGGACCCTGTTGCTCCTTTCCCTGTCCT
1681 CTCTGTTGACCCAGAATATTGTGTTAATCCTTTAGCCCACCCAGTATTTTCTGTTGCTCA
1741 GACGGACCTGCAGGCATTCTCCATGCAGAACGGTCTGAATGGACAAGTGGATGTCTCACT
1801 TGCTTCTGCAGCCTCTGCTGTGGAGAGCCTGAAGCCAGCACTCCTTGCTGGCCAGCCTCT
1861 AGTGTATGTGCCCTCTGCCTCACTGTTCATGCTGTATGGAAGTCTGCAGGAGGGACCAGC
1921 GTCAGGGTCAGGGTCAGAGAGGGATGACAGAAGCTCAGAAGCCCCAGCCACAGTAGAGCT
1981 GTCATCTGCACCCTCAGCTCAGAAGCGCCTCTGTGAGGAGAGGAAACCTCAGGAGGAGGA
2041 TGAGCCAGCCACTAAAAGGCAAAGTAGGGAATATGAAGACGGCCCGCTGTCGCTTGTCAT
2101 GCCCAAGAAACCCTCAGATTCCACAGACCTTGCCTCTCCCAAGACTATGGGTAACAGGGC
2161 ATCTATACCCCTCAAAGACATTCATGTGAATGGCCAACTCCCTGCTGCAGAAGAGATTTC
2221 AGGAAAGGCAACAGCAAACTCTCTTGTTTCTTCTGAGTGGGGAAATCCTTCAAGAAATAC
2281 AGATGTTGAAAAGCCTTCAAAAGAAAATGAAAGCACCAAAGAGCCTTCTTTGCTACAATA
2341 TCTTTGTGTGCAGTCTCCTGCAGGATTAAATGGTTTCAATGTACTTTTATCTGGCAGTCA
```

-continued

```
2401 AACCCCCCCTACTGTGGGCCCGTCCTCAGGTCAGCTGCCGTCTTTCAGTGTCCCTTGCAT
2461 GGTCTTACCATCTCCACCTCTGGGCCCTTTTCCTGTTCTCTATTCTCCTGCAATGCCGGG
2521 CCCGGTTTCTTCCACTCTTGGTGCTCTCCCAAACACAGGACCTGTGAATTTCAGCTTGCC
2581 TGGCCTTGGATCAATAGCCCAGCTTCTCGTCGGCCCCACAGCTGTGGTTAATCCAAAGTC
2641 GTCCACACTCCCTTCTGCAGACCCTCAGCTTCAGAGTCAGCCCTCACTAAACCTAAGTCC
2701 AGTGATGTCAAGGTCACACAGTGTCGTCCAACAACCTGAGTCCCCCGTTTACGTGGGACA
2761 TCCAGTCTCAGTAGTAAAATTACAACAGTCACCAGTTCCAGTGACCCCCAAGAGCATCCA
2821 ACGCACACATCGTGAGACGTTTTTCAAGACACCCGGCAGCCTTGGAGACCCTGTCCTGAA
2881 GAGAAGAGAAAGGAACCAGTCACGAAACACCAGCTCGGCCCAGAGGAGACTAGAAATCCC
2941 CAGCGGCGGCGCTGACTAACCTGCCGCTTTGCCAGGTGGGGGTGGGATCAAACGCCCTGA
3001 GAGTCCCGGATGTCCGAGGCGGGATGCAAACCATCCCGTCCTGAGCACGGGTCCTTCCTC
3061 TCTCTTTCATCCACACTTCTGTTAACTTCCCACCACCATCAATCATCTGATTTCCTGAAA
3121 GTAATTAATTGTGCATTTAATACCAGTTAGAGTTCCGACTCTGCATGGTGTCACAGTGAA
3181 AGCGCCGACTGACTTATGGTTTTGATTCAAGAATCGTCTTATTGCTGGAAGTAGATCTGA
3241 ATAGGCTACCGGAGCCTTGTTTTTCTAAAGGGGGCGCTGTCTAGCACTTAACTAGGGTA
3301 AGCATTCTTAACATGTATTTCCACTTGCCCTGAGTAAATCTGTGGTGAGAGAAGCTTCCT
3361 TTCTGCAGTTTAAAAAAGCTACTGCTTCCTTAGGCTTCATCAGGAAGCCACCTTCAGTTG
3421 TGAATCCTATGGTGTTATTTATTTTGTTCCTGAAATGGGATTTAGTGCAAAAAGTTTACA
3481 ACTACAGTCTTTAACACATTTTTTTCAGGGTATGACGACTTGAATGTTTATACTTTTATT
3541 CTATAATTTGCCCTGCACTTATTTTACAACCTAGTAATAATGTGGATAAATGTATCTACA
3601 TGACACATGTCAAGACCAAAATAACTGTGAATGACACACCTTGCTGTAAATGAACTGTGC
3661 TAACCCTGACTGTGGGCTTGAGAACAAAGATGAACTCTAGAACTCTAGCAGCCTAACTGC
3721 TGCTTCTCAAATAACTGTGTGAACAGTGAGATATTACTGTTTGTTTCTAAAAATCCTACT
3781 GTGCCCAGTTTCCTTCACTACATGCCCTGCATTTTTTATTTAAATATTTAGCTGTAGCGC
3841 CATCAGATATGGATGCCTTCTAACAATTGCTGTTTGTAAAATAAATCAGGATGGTAGAAA
3901 GTGATTATATGGAAAATTGGAACCTGGATGAGACCTTTTCGTTGAATTCTGAAGAGTAAT
3961 GATGTGAAAATTGATACAGGGCAAGAGATGATTCTTTTGTTTTCTTCTACTTCATGTCC
4021 AGAAGAGTAAGAGGGAAAATGGACATATGTTTCATATCCAAGGGTATTCAAACTGTAGTT
4081 AGTTGGTACCTCTGAAAAATGAGAATGGTGAGCGCACGGGTTGGTTGTTCTAGCATGAAT
4141 ACAATTCTGGAAACTGTTATGCAATTTCCCTTTTTAACCCACATTACTTTAGGGGTGCA
4201 TTAAGTCGCCAAACTATACTAGTTCTTTGTATTCCTAGACTTGCTGATATTTACCTCTCT
4261 CTTGTCTCTTCAGAGTAAATGGTTCCCTTCTTTCCTTCCTACTTTCCTTCATTCTCTCTT
4321 CCTTCCCTCCTTCCTACTTCTTTTCTTCCTTCCTCTTCCTCTCTTAAAACTATCTTAGAT
4381 GTAGAATCCTGGTGTAGGGTTTTATTTTATTTTTATTTTTTGACCCAATAAAATGTTATA
4441 TGAAAGAATGAAAATATTAATTTAAGAGACTCTGGGAGTCTGAATAAAGTAGCTTTATAT
4501 TAACTAGAGGATAATATTAGCCTTATTACCCCCACAAGATTTTTAAAACTTGAGGTAGG
4561 TAGCTACATTAAATAAATTTGCTACTTATATAAAAATTTTTATCAACACTAAACTTTTAA
4621 AGTTTACAAGTTTTTTTTTCTTTTTTACAGTCTTCTATAGAGTTAGGTTAAAAATGTGG
4681 TTCTAACCATCAACAATTGCATGGTTAAATGACCCTGAACTAAAACTGATGGGTTCCCTA
4741 TCAAAACAAATAAAAATATACCTTTTTCAGGTTTCAATCTGTGCAGGGTATATGCATGTT
```

```
-continued
4801 AATTCTACCATGCTTAAGAACTTCCACAAAATATTTCATGGAGAGGTCTGCATTTAGACG

4861 GAAACAGAAATTGCTTTTCCCCTCACTGTTCCTGAATGCTGTATACTTGTTTTAACATTT

4921 TTGCTATCTTTTTTTATTATTCTGATCATGATATGACCATTTAACCTCAGAATTCATAAT

4981 TCCTGAGGGGTGTTAAGAAGCAGTCCCATTGGTGAGGATATTATGACTTGGTGACCATTC

5041 TTAGGAGTAGAAAACCAAGGACAATTGCTTCTGTATTCAGTATCCACTTCTTAATGTGGC

5101 TTTATATGTAAAAATAATAATGCAGTGGTTGTTTCTGTCAGGAAAATAAATCTTACAGAA

5161 CAACTGGTGGAATTGAAGCTGCTGCGCTAGACTTGGATATTTTGGGTAGTGAAGAAGCAA

5221 TGGCAATCTTGAGTCTATTATTGTATAATTTAGTAAAAGAAAAAAATAATCGTTGGTGGT

5281 CCTACTAAGAGAATGCAGCTTTTTGAGTTGTCACAGAGGCTGTGTGTGCCCTACAGTGA

5341 CCAGGGTTTGTAAAACCCTTTCATTCTGGTACAAGAGTCGGGGGTATAACTTTTATACTT

5401 GAATCTACCTACCAAGTTTACATTTCTCAATTCCTTTTTGTAAGGTGCTATTTCTGTATT

5461 TAAATAACTTTCTTTTAACGTAAAGCTGCTTTCTGCTTATCTTATTGCACTGCTAGTTGT

5521 ATGTAGGTATTAATTTTATTGCTGCTTACTGCTTTTGTTTTCTTATTATTTAGCTCTGCT

5581 CTTTTTCCTAATGGCTATATTATCTATAGCTATTTACTTGTAACTGTACTACATGTAAAC

5641 TGATTTTTTGTTCTGATTTTTTTTCTAATATTTTTAGGAAAATATTAAGCTTTATAAAAT

5701 AGCAATAAAAAATAATTCATTTAA
```

Alignment of SEQ ID NO:08 with the sequence of ACCESSION number of NT_009551 showed that the F13 gene contains approximately 13 exons in a span of 45,500 bases. Alignment with the ESTs in the genbank database showed that alternate splicing may occur, resulting in exon 12 being spliced out and/or the intron following exon 5 being left in the encoding sequence. FIG. 2 shows the exons of the F13 gene and also the corresponding amino acid sequence (SEQ ID NO:09).

An open reading frame exists in SEQ ID NO:08 and the corresponding amino acid sequence, SEQ ID NO:09 is given below. This open reading frame was shown to be in frame with the Yeast Gal4 activation domain of the plasmids pSSI864 and pSSI865 in which Family 13 was originally identified in the One-hybrid screen. A stop codon exists at bases 20-22 that is in frame with the coding sequence and an ATG start codon is located at bases 209-211.

```
                                              SEQ ID NO: 09
MEVNCLTLKDLISPRQPRLDFAVEDGENAQKENIFVDRSRMAPKTPIKNE

PIDLSKQKKFTPERNPITPVKLVDRQQAEPWTPTANLKMLISAASPDIRD

REKKKGLFRPIENKDDAFTDSLQLDVVGDSAVDEFEKQRPSRKQKSLGLL

CQKFLARYPSYPLSTEKTTISLDEVAVSLGVERRRIYDIVNVLESLHLVS

RVAKNQYGWHGRHSLPKTLRNLQRLGEEQKYEEQMAYLQQKELDLIDYKF

GERKKDGDPDSQEQQLLDFSEPDCPSSSANSRKDKSLRIMSQKFVMLFLV

SKTKIVTLDVAAKILIEESQDAPDHSKFKTKVRRLYDIANVLTSLALIKK

VHVTEERGRKPAFKWIGPVDFSSSDEELVDVSASVLPELKRETYGQIQVC

AKQKLARHGSFNTVQASERIQRKVNSEPSSPYREEQGSGGYSLEIGSLAA

VYRQKIEDNSQGKAFASKRVVPPSSSLDPVAPFPVLSVDPEYCVNPLAHP

VFSVAQTDLQAFSMQNGLNGQVDVSLASAASAVESLKPALLAGQPLVYVP

-continued
SASLFMLYGSLQEGPASGSGSERDDRSSEAPATVELSSAPSAQKRLCEER

KPQEEDEPATKRQSREYEDGPLSLVMPKKPSDSTDLASPKTMGNRASIPL

KDIHVNGQLPAAEEISGKATANSLVSSEWGNPSRNTDVEKPSKENESTKE

PSLLQYLCVQSPAVTSSSDPQEHPTHTS
```

These data indicate that F13 (and proteins/polypeptides substantially similar thereto as defined above) is a transcription factor that represses telomerase expression by binding to Site C. As such, the TERT repressor proteins of interest have an encoding nucleic acid sequence that is substantially the same as, or identical to, that sequence which encodes for F13. A given sequence is considered to be substantially similar to the F13 sequence if it shares high sequence similarity with the above described specific sequence, e.g. at least 75% sequence identity, usually at least 90%, more usually at least 95% sequence identify with the above specific sequence.

V. F13 Protein Consensus Sequence Homology

Blastx analysis of the F13 protein sequence against the NCBI protein database identified two regions near the C-terminus that have homology to the DNA binding domain of E2F.

The first E2F-"like" binding domain is an approximately 90 residue long amino acid stretch near the C-terminus of the protein starting at amino acid residue 141. The blast analysis of this sequence indicated 41% identity, 54% positives and 8% Gaps when compared with the DNA binding domain of human transcription factor E2F-2 (accession no. AL021154). The homology between the two proteins was found to extend into the leucine zipper (protein-protein interaction) domain of human E2F-2 that is adjacent to the DNA binding domain. The above sequence homology was the strongest match to a human protein found in the genbank database. All of the F13 protein blast searches were carried out under default parameters. [the default parameters are: Expect=10; Word Size=3; Matrix=BLOSUM62; Gap Costs: Existence=11 and Extension=1].

The results are:

```
>gi|4758226|ref|NP_004082.1| E2F transcription factor 2 [Homo sapiens]
 gi|11423037|ref|XP_001540.1| E2F transcription factor 2 [Homo sapiens]
 gi|2494228|sp|Q14209|E2F2_HUMAN TRANSCRIPTION FACTOR E2F2 (E2F-2)
 gi|1082847|pir||A54595 transcription factor E2F-2 - human
 gi|410207|gb|AAA16890.1| (L22846) E2F-2 [Homo sapiens]
 gi|3219577|emb|CAA15949.1| (AL021154) dJ15O05.1 (transcription factor E2F-2)
[Homo sapiens]
          Length = 437

Score = 53.7 bits (128), Expect = 1e-05
Identities = 39/93 (41%), Positives = 52/93 (54%), Gaps = 8/93 (8%)

Query: 141 SRKQKSLGLLCQKFLARYPSYPLS-TEKTTISLDEVAVSLGVERRRIYDIVNVLESLHLV    199
           +R   SLGLL +KF+      Y LS +E   + L+  A  L V++RRIYDI NVLE + L+
Sbjct: 128 TRYDTSLGLLTKKFI-----YLLSESEDGVLDLNWAAEVLDVQKRRIYDITNVLEGIQLI    182

Query: 200 SRVAKNQYGWHGRHSLPKTLR--NLQRLGEEQK                              230
            + AKN   W GR        R    Q+LG+E K
Sbjct: 183 RKKAKNNIQWVGRGMFEDPTRPGKQQQLGQELK                              215

Score = 37.5 bits (86), Expect = 0.86
Identities = 26/80 (32%), Positives = 42/80 (52%), Gaps = 14/80 (17%)

Query: 272 PDCPSSSA-NSRKDKSLRIMSQKFVMLFLVSKTKIVTLDVAAKILIEESQDAPDHSKFKT    330
           P   P S    +R D SL ++++KF+ L    S+  ++ L+ AA++L
Sbjct: 118 PKTPKSPGEKTRYDTSLGLLTKKFIYLLSESEDGVLDLNWAAEVL-------------DV    164

Query: 331 KVRRLYDIANVLTSLALIKK                                           350
            + RR+YDI NVL  + LI+K
Sbjct: 165 QKRRIYDITNVLEGIQLIRK                                           184
```

The second E2F DNA binding domain identified in F13 is a 80 residue long amino acid stretch (272 to 350 amino acid residues) and was found to have 232% overall sequence identity (52% positives (42/80) and 17% Gaps (14/80)) with the DNA binding domain of human E2F-2. The two E2F-"like" DNA binding domains of F13 are likely regions of the protein that regulate the TERT promoter by binding to site C.

A Protein tblastn analysis of the NCBI Human Genome Database also identified a region of the human genome, on chromosome 11, that contains a coding sequence that shows strong protein homology to F13. This coding sequence from Chromosome 11 also contains a E2F-like DNA binding domain. The default parameters for this search were:
    Expect=0.01
And the results are:

```
>ref|NT_009107.3|Hs11_9264 Homo sapiens chromosome 11 working draft sequence
segment
          Length = 2509807

Score =
93.6 bits (231), Expect = 5e-17
 Identities = 43/64 (67%), Positives = 54/64 (84%)
 Frame = +2

Query:    181 VERRRIYDIVNVLESLHLVSRVAKNQYGWHGRHSLPKTLRNLQRLGEEQKYEEQMAYLQQ    240
              VERRRIYDIVNVLESLH+VSR+AKN+Y WHGRH+L KTL  L+ +GEE KY EQ+  +++
Sbjct: 291149 VERRRIYDIVNVLESLHMVSRLAKNRYTWHGRHNLNKTLGTLKSIGEENKYAEQIMMIKK    291328

Query:    241 KELD                                                          244
              KE +
Sbjct: 291329 KEYE                                                          291340

Score =
75.5 bits (184), Expect = 1e-11
 Identities = 35/41 (85%), Positives = 37/41 (89%)
 Frame = -1

Query:    328 FKTKVRRLYDIANVLTSLALIKKVHVTEERGRKPAFKWIGP                     368
              F  K+RRLYDIANVL+SL LIKKVHVTEERGRKPAFKW GP
Sbjct: 207364 FPAKIRRLYDIANVLSSLDLIKKVHVTEERGRKPAFKWTGP                     207242

Score =
71.6 bits (174), Expect = 2e-10
 Identities = 40/66 (60%), Positives = 50/66 (75%), Gaps = 1/66 (1%)
 Frame = +2

Query:    277 SSANSRKDKSLRIMSQKFVMLFLVSKTKIVTLDVAAKILI-EESQDAPDHSKFKTKVRRL    335
              +S NSRKDKSLR+MSQKFVMLFLVS  +IV+L+VAAKILI E+    D SKFK+K
```

```
-continued
Sbjct:  291683  ASVNSRKDKSLRVMSQKFVMLFLVSTPQIVSLEVAAKILIGEDHVEDLDKSKFKSKCHDC  291862

Query:     336  YDIANV                                                        341
                +    N+
Sbjct:  291863  HGFLNL                                                     291880

Score = 70.9
bits (172), Expect = 3e-10
 Identities = 38/80 (47%), Positives = 51/80 (63%), Gaps = 2/80 (2%)
 Frame = +1

Query:      31  KENIFVD-RSRMAPKTPIKNEPIDLSKQKKFTPERNPIT-PVKLVDRQQAEPWTPTANLK       88
                +EN+F +   R    KTP+K           +  P+   P+T P K  + Q EPWTPTANLK
Sbjct:  288070  QENLFCEPHKRGLMKTPLKESTTANIVLAEIQPDFGPLTTPTKPKEGSQGEPWTPTANLK  288249

Query:      89  MLISAASPDIRDREKKKGLF                                          108
                MLISA SP+IR+R++K+GLF
Sbjct:  288250  MLISAVSPEIRNRDQKRGLF                                       288309

Score =
66.6 bits (161), Expect = 6e-09
 Identities = 32/47 (68%), Positives = 35/47 (74%)
 Frame = +3

Query:     133  DEFEKQRPSRKQKSLGLLCQKFLARYPSYPLSTEKTTISLDEVAVSL                  179
                DEFEK +PSRK+KSLGLLC KFLARYP+YP         I LDEVA  L
Sbjct:  288750  DEFEKSQPSRKEKSLGLLCHKFLARYPNYPNPAVNNDICLDEVAEEL           288890
```

The full length amino acid sequence of this F13 homolog, referred to herein as F13H, is provided below as SEQ ID NO:11 in FIG. 3; the nucleotide coding sequence for this homolog is provided as SEQ ID NO:10 in FIG. 4 and the genomic coding sequence is provided as SEQ ID NO:12 in FIG. 5.

VI. Additional Characterization of F13

Further experiments were performed to confirm that the F13 protein binds to the Site C site of the Telomerase minimal promoter. In a first experiment, a mutated Site C site in which base −65 (relative to the ATG of telomerase) was converted from a C to an A was assayed for its ability to bind to the F13 repressor protein. It was found that the F13 repressor protein could not bind to the mutated Site C site. In a second experiment, three mutant F13 proteins were prepared: (a) a knockout of the E2F-A domain; (b) a knockout of the E2F-B domain; and (c) a knockout of both E2F domains. All three of these F13 mutants were found to be unable to bind to Site C. In a third experiment, F13 was shown to bind to the 21 base full-length site C where either multiple copies of Site C, or a single copy of Site C was used as a yeast bait. The above additional assays demonstrate that F13 binds to Site C.

It is evident from the above results and discussion that the subject invention provides important new nucleic acid compositions that find use in a variety of applications, including the establishment of expression systems that exploit the regulatory mechanism of the TERT gene and the establishment of screening assays for agents that enhance TERT expression. In addition, the subject invention provides methods of enhancing TERT expression in a cellular or animal host, which methods find use in a variety of applications, including the production of scientific research reagents and therapeutic treatment applications. Accordingly, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for modulating a binding event between a human TERT minimal promoter Site C binding site and an F13 Site C repressor protein, said method comprising:
contacting said human TERT minimal promoter Site C binding site and/or said F13 Site C repressor protein with a modulatory agent under conditions sufficient for binding between said human TERT minimal promoter Site C and said F13 Site C repressor protein to be modulated, wherein said F13 Site C repressor protein comprises SEQ ID NO:09.

2. The method according to claim 1, wherein said method is a method of inhibiting binding between said human TERT minimal promoter Site C binding site and said F13 Site C repressor protein.

3. The method according to claim 1, wherein said method is a method of enhancing binding said human TERT minimal promoter Site C binding site and said F13 Site C repressor protein.

4. The method according to claim 1, wherein said binding event is an in vitro binding event.

5. The method according to claim 1, wherein said binding event is an in vivo binding event.

6. A method of modulating expression of TERT from a TERT expression system that includes a human TERT minimal promoter Site C binding site, said method comprising:
modulating TERT expression by contacting said system with a modulatory agent under conditions sufficient for binding between said human TERT minimal promoter Site C binding site and an F13 Site C repressor protein to be modulated, wherein said F13 Site C repressor protein comprises SEQ ID NO:09.

7. The method according to claim 6, wherein said method is a method of inhibiting binding between said human TERT minimal promoter Site C binding site and said F13 Site C repressor protein.

8. The method according to claim 6, wherein said method is a method of enhancing binding between said human TERT minimal promoter Site C binding site and said F13 Site C repressor protein.

9. The method according to claim 6, wherein said binding event is an in vitro binding event.

10. The method according to claim 6, wherein said binding event is an in vivo binding event.

* * * * *